(12) United States Patent
Muraca

(10) Patent No.: US 7,763,438 B2
(45) Date of Patent: Jul. 27, 2010

(54) GENE AND PROTEIN EXPRESSION PROFILES ASSOCIATED WITH THE THERAPEUTIC EFFICACY OF IRINOTECAN

(75) Inventor: Patrick J. Muraca, Pittsfield, MA (US)

(73) Assignee: Nuclea Biomarkers, LLC, Pittsfield, MA (US)

( * ) Notice: Subject to any disclaimer, the term of this patent is extended or adjusted under 35 U.S.C. 154(b) by 0 days.

(21) Appl. No.: 12/284,387

(22) Filed: Sep. 22, 2008

(65) Prior Publication Data

US 2009/0047684 A1    Feb. 19, 2009

Related U.S. Application Data

(62) Division of application No. 11/903,470, filed on Sep. 21, 2007, now abandoned.

(60) Provisional application No. 60/906,438, filed on Mar. 12, 2007, provisional application No. 60/846,298, filed on Sep. 21, 2006.

(51) Int. Cl.
*G01N 33/574* (2006.01)

(52) U.S. Cl. ..................................... 435/7.23; 530/350

(58) Field of Classification Search ................ 435/7.23; 530/350

See application file for complete search history.

(56) References Cited

OTHER PUBLICATIONS

Cham et al (JBC, 278(19):17044-17052, 2003).*
Skolnick et al (Trends in Biotechnology, 18:34-39, 2000).*
Singh et al (AJCO, 21(5), Oct. 1998, pp. 466-469) attached as pp. 1-6.*

* cited by examiner

*Primary Examiner*—Stephen L Rawlings
*Assistant Examiner*—Brad Duffy
(74) *Attorney, Agent, or Firm*—Paula C. Evans

(57) ABSTRACT

The present invention includes gene and protein expression profiles indicative of whether a cancer patient is likely to respond to treatment with irinotecan. By identifying such responsiveness, a treatment provider may determine in advance those patients who would benefit from such treatment, as well as identify alternative therapies for non-responders. The present invention further provide methods of using the gene and/or protein expression profiles and assays for identifying the presence of a gene and/or protein expression profile in a patient sample.

4 Claims, 1 Drawing Sheet

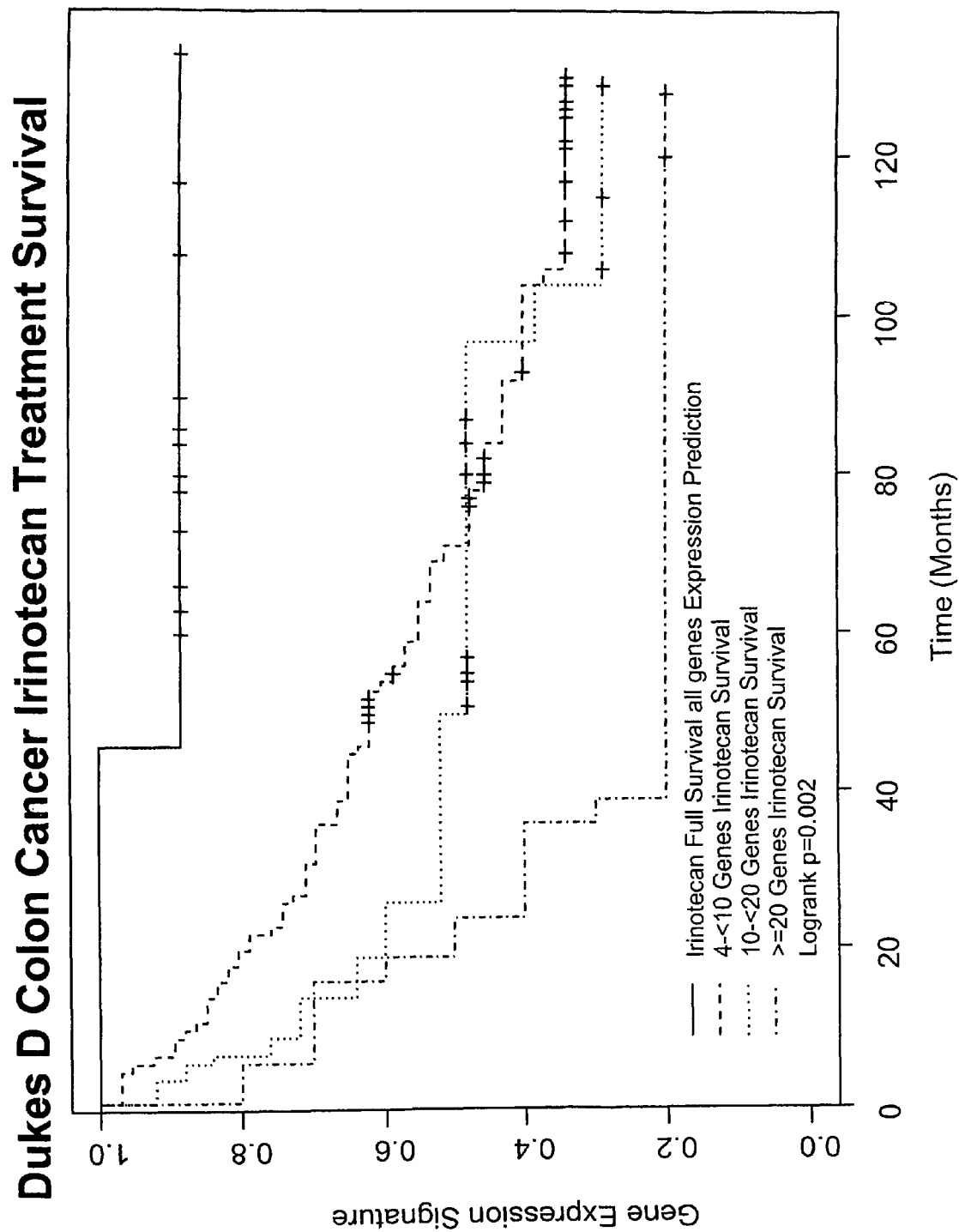

GENE AND PROTEIN EXPRESSION PROFILES ASSOCIATED WITH THE THERAPEUTIC EFFICACY OF IRINOTECAN

RELATED APPLICATIONS

This application is a Divisional patent application of Ser. No. 11/903,470 filed on 21 Sep. 2007, which claims priority under 35 U.S.C. §119(e) to U.S. provisional Application Ser. No. 60/846,298 filed Sep. 21, 2006 and Application Ser. No. 60/906,438 filed Mar. 12, 2007, the entirety of which are incorporated herein by reference.

BACKGROUND OF THE INVENTION

Patients diagnosed with cancer are faced with costly and often painful treatment options. These treatments may be ineffective in a subpopulation of patients, and as a result, these patients endure these treatments without little or no therapeutic benefit. Some patients may react adversely to certain agents causing additional suffering and possibly death.

Ineffective treatment also is problematic because time is a key variable when treating cancer. A treatment provider has a far greater chance of containing and managing the disease if the cancer is diagnosed at an early stage and treated with a therapeutically effective agent. An agent may provide great therapeutic benefits if administered at an early stage of the disease; however, with the passage of time, the same agent may cease to be effective.

Colorectal cancer is an example of a condition where early diagnosis is key for effective treatment. Colorectal cancer is cancer that develops in the colon or the rectum. The walls of the colon and rectum have several layers of tissue. Colorectal cancer often starts in the innermost layer and can grow through some or all of the other layers; the stage (extent of spread) of a colorectal cancer depends to a great degree on how deeply it has grown into these layers.

Chemotherapy is often used for treating colorectal cancer. Irinotecan hydrochloride (CAMPTOSAR®) is a chemotherapeutic agent indicated for first-line therapy of colorectal cancers. As with many chemotherapeutic agents, administration of irinotecan hydrochloride ("irinotecan") often causes deleterious side effects for the patient, and some patients do not respond well to the treatment. Some patients thus undergo treatment with irinotecan and suffer the painful side effects only to later realize that the agent has not been therapeutically beneficial to their condition. In addition to the unnecessary suffering, critical time is lost in determining an alternative treatment.

SUMMARY OF THE INVENTION

The present invention provides gene and protein expression profiles and methods of using them to identify those patients who are likely to respond to treatment with irinotecan (these patients are referred to as "responders"), as well as those patients who are not likely to benefit from such treatment (these patients are referred to as "non-responders"). The present invention allows a treatment provider to identify those patients who are responders to irinotecan treatment, and those who are not non-responders to such treatment, prior to administration of the agent.

In one aspect, the present invention comprises gene expression profiles, also referred to as "gene signatures," that are indicative of a cancer patient's tendency to respond to treatment with irinotecan. The gene expression profile (GEP) comprises at least one, and preferably a plurality, of genes selected from the group consisting of ERBB2, GRB7, Erk1 kinase, JNK1 kinase, BCL2, phospho-GSK-3beta, MMP11, CTSL2, CCNB1, BIRC5, MK167, STK6, MRP14, phospho-Akt, CD68, BAG1 and GSTM1. The gene signature may further include reference or control genes. The currently preferred reference genes are ACTB, GAPD, GUSB, RPLP0 and TFRC. According to the invention, some or all of theses genes are differentially expressed (e.g., up-regulated or down-regulated) in patients who are responders to irinotecan therapy. Specifically, ERBB2, GRB7, JNK1 kinase, BCL2, MK167, phospho-Akt, CD68 and BAG1 are up-regulated (over-expressed) and Erk1 kinase, phospho-GSK-3beta, MMP11, CTSL2, CCNB1, BIRC5, STK6, MRP14 and GSTM1 are down-regulated (under-expressed) in patients who are responders to irinotecan. Reference genes ACTB, GAPD, GUSB, RPLP0 and TFRC are up-regulated (over-expressed).

The present invention further comprises protein expression profiles that are indicative of a cancer patient's tendency to respond to treatment with irinotecan. The protein expression profiles comprise those proteins encoded by the genes of the GEP that also are differentially expressed in colon cancers that are responsive to irinotecan therapy. The present protein expression profile (PEP) comprises at least one, and preferably a plurality, of proteins encoded by the genes selected from the group consisting of ERBB2, GRB7, Erk1 kinase, JNK1 kinase, BCL2, phospho-GSK-3beta, MMP11, CTSL2, CCNB1, BIRC5, MK167, STK6, MRP14, phospho-Akt, CD68, BAG1 and GSTM1. The protein expression profile may further include proteins encoded by reference genes. The currently preferred reference genes are ACTB, GAPD, GUSB, RPLP0 and TFRC. According to the invention, some or all of theses proteins are differentially expressed (e.g., up-regulated or down-regulated) in patients who are responders to irinotecan therapy. Specifically, proteins encoded by the following genes are up-regulated (over-expressed): ERBB2, GRB7, JNK1 kinase, BCL2, MK167, phospho-Akt, CD68 and BAG1; and proteins encoded by the following genes are down-regulated (under expressed): Erk1 kinase, phospho-GSK-3beta, MMP11, CTSL2, CCNB1, BIRC5, STK6, MRP14 and GSTM1, in patients who are responders to irinotecan. Reference proteins ACTB, GAPD, GUSB, RPLP0 and TFRC are up-regulated (over-expressed).

The gene and protein expression profiles of the present invention (referred to hereinafter as GPEPs) comprise a group of genes and proteins that are differentially expressed (e.g., up-regulated or down-regulated) in patients who are responders to irinotecan therapy relative to expression of the same genes in patients who are non-responders to this therapy. Patients having tumors that are non-responsive to irinotecan often experience recurrence of their disease or disease-related death. The GPEPs of the present invention thus can be used to predict not only responsiveness of a colon cancer to irinotecan therapy, but also the likelihood of recurrence of the cancer and/or disease-related death.

The present invention further comprises a method of determining if a patient is a responder or non-responder to treatment with irinotecan. The method comprises obtaining a tumor sample from the patient, determining the gene and/or protein expression profile of the sample, and determining from the gene or protein expression profile whether at least one, preferably at least 4, more preferably at least 10, and most preferably at least 16 of the genes selected from the group consisting of ERBB2, GRB7, Erk 1 kinase, JNK1 kinase, BCL2, phospho-GSK-3beta, MMP11, CTSL2, CCNB1, BIRC5, MK167, STK6, MRP14, phospho-Akt, CD68, BAG1 and GSTM1, or at least one protein selected from the proteins encoded by these genes, is differentially expressed in the sample. From this information, the treatment provider can ascertain whether the patient is likely to benefit from irinotecan therapy. The present method also can be used to predict late recurrence and disease related death associated with the therapy.

The present invention further comprises assays for determining the gene and/or protein expression profile in a patient's sample, and instructions for using the assay. The assay may be based on detection of nucleic acids (e.g., using nucleic acid probes specific for the nucleic acids of interest) or proteins or peptides (e.g., using antibodies specific for the proteins/peptides of interest). In a currently preferred embodiment, the assay comprises an immunohistochemistry (IHC) test in which tissue samples, preferably arrayed in a tissue microarray (TMA), and are contacted with antibodies specific for the proteins/peptides identified in the GPEP as being indicative of a patient's responsiveness to irinotecan.

BRIEF DESCRIPTION OF THE DRAWINGS

FIG. 1 is a graph showing the survival rates for patients treated with irinotecan HCl correlated with the present gene expression profile predicting responsiveness to irinotecan therapy.

DETAILED DESCRIPTION

The present invention provides gene and protein expression profiles and their use for predicting a patient's responsiveness to a cancer treatment. More specifically, the present GPEPs are indicative of whether a patient is a responder or a non-responder to treatment with irinotecan. Those patients identified as responders using the present GPEP are likely to benefit from irinotecan therapy, whereas those patients identified as non-responders may avoid unnecessary treatment with irinotecan and consider other treatment options in a timely manner. The present GPEPs also can be used to predict the likelihood of recurrence of colon cancer and disease related death associated with irinotecan therapy in some patients.

Irinotecan is a chemotherapeutic agent which belongs to the group of medicines called antineoplastics. It is indicated as first-line therapy for treating cancers of the colon or rectum. Irinotecan interferes with the growth of cancer cells, which are eventually destroyed. Because the growth of normal cells may also be affected by the medicine, other effects also may occur. These other effects may include: increased sweating and production of saliva, diarrhea, nausea (feeling sick) and vomiting, loss of appetite, lowered resistance to infection, bruising or bleeding, anemia, hair loss, tiredness and a general feeling of weakness. The present invention enables the treatment provider to determine in advance those patients likely to benefit from irinotecan treatment, and to consider alternative treatment options for non-responders. It is understood that treatment with irinotecan includes administering irinotecan alone and in combination with other therapeutic agents or adjuvants. The current indications for CAMPTOSAR® include administering irinotecan HCl in combination with 5-fluorouracil (5-FU) and leucovorin (LV) as first-line therapy for metastatic colorectal cancer, and alone as a second-line therapy for patients whose disease has returned or progressed following initial 5-FU therapy.

The genes comprising the present GEP include: ERBB2, GRB7, Erk1 kinase, JNK1 kinase, BCL2, phospho-GSK-3beta, MMP11, CTSL2, CCNB1, BIRC5, MK167, STK6, MRP14, phospho-Akt, CD68, BAG1 and GSTM1. In a preferred embodiment, the present gene expression profile further includes the following reference genes: ACTB, GAPD, GUSB, RPLP0 and TFRC. The NCBI Accession Number of a variant of each of these genes is set forth in Table 1; other variants exist which can be readily ascertained by reference to an appropriate database such as NCBI Entrez, and these variants are encompassed by the present invention. These genes are either up- or down-regulated in patients that are responsive to irinotecan therapy, and not in patients that experience late recurrence of their disease or disease related death associated with the therapy. Accordingly, it is possible to determine in advance if a patient is likely to benefit from irinotecan therapy by obtaining a gene expression profile from the patient's tissue, and determining whether one or more of the genes in the present GEP is up- or down-regulated. Table 1 identifies the genes and indicates whether these genes are up- or down-regulated in patients that are responders to irinotecan therapy.

TABLE 1

| | GENE NAME | ALT GENE NAME | UP- or DOWN-REGULATION | NCBI ACCESSION NO. | SEQ ID NO. |
|---|---|---|---|---|---|
| HER2 Amplicon | ERBB2 | HER2 | Up | NM_004448 | 1 |
| | GRB7 | | Up | NM_005310 | 2 |
| ER Expression Cluster | Erk1 kinase | | Down | X60188 | 3 |
| | JNK1 kinase | | Up | NM_002750 | 4 |
| | BCL2 | | Up | NM_000633 | 5 |
| | GSK-3-beta | | Down | NM_002093 | 6 |
| Invasion Group | MMP11 | STMY3; stromolysin 3 | Down | NM_005940 | 7 |
| | CTSL2 | cathepsin L2 | Down | NM_001333 | 8 |
| Proliferation Cluster | CCNB1 | cyclin B1 | Down | NM_031966 | 9 |
| | BIRC5 | SURV; survivin | Down | NM_001168 | 10 |
| | MKI67 | Ki-67 antigen | Up | NM_002417 | 11 |
| | STK6 | STK15; BTAK | Down | NM_003600 | 12 |
| | Akt (Ser473) | | Up | NM_005163 | 13 |
| Other Genes | CD68 | | Up | NM_001251 | 14 |
| | BAG1 | | Up | NM_004323 | 15 |
| | GSTM1 | glutathione-s-transferase M1 | Down | NM_146421 | 16 |
| | MRP14 | S100 calcium binding protein A9 | Down | NM_002965 | 17 |
| Reference Genes | ACTB | β-Actin | Up | NM_001101 | 18 |
| | GAPD | GAPDH | Up | NM_002046 | 19 |
| | GUSB | GUS | Up | NM_000181 | 20 |

TABLE 1-continued

| GENE NAME | ALT GENE NAME | UP- or DOWN-REGULATION | NCBI ACCESSION NO. | SEQ ID NO. |
|---|---|---|---|---|
| RPLP0 | | Up | NM_001002 | 21 |
| TFRC | | Up | NM_003234 | 22 |

In a preferred aspect of the present invention, the gene profile of the present invention comprises at least four, preferably between four and ten, more preferably at least ten, and most preferably at least sixteen, of the genes in the present GEP, up- or down-regulated as applicable, together with one or more reference genes.

The gene expression profiles of the invention can be used to predict the responsiveness of a colon cancer patient to irinotecan therapy. In one aspect, the present method comprises (a) obtaining a gene expression profile from a biological sample of a patient afflicted with colon cancer; (b) determining from the gene expression profile whether one or more of the following genes are up-regulated (over-expressed): ERBB2, GRB7, JNK1 kinase, BCL2, MK167, phospho-Akt, CD68 and BAG1; and/or whether at least one of the following genes are down-regulated (under-expressed): Erk1 kinase, phospho-GSK-3beta, MMP11, CTSL2, CCNB1, BIRC5, STK6, MRP14 and GSTM1. Preferably, expression of at least two reference genes also is measured. The predictive value of the gene profile for determining response to irinotecan increases with the number of these genes that are found to be up- or down-regulated in accordance with the invention. Preferably, at least about four, more preferably at least about ten and most preferably at least about sixteen of the genes in the present GPEP are differentially expressed.

The present invention further comprises protein expression profiles that are indicative of a cancer patient's tendency to respond to treatment with irinotecan. The protein expression profile comprises at least one, preferably a plurality, of proteins encoded by the genes selected from the group consisting of ERBB2, GRB7, Erk1 kinase, JNK1 kinase, BCL2, phospho-GSK-3beta, MMP11, CTSL2, CCNB1, BIRC5, MK167, STK6, MRP14, phospho-Akt, CD68, BAG1 and GSTM1. According to the invention, some or all of theses proteins are differentially expressed (e.g., up-regulated or down-regulated) in patients who are responders to irinotecan therapy. Specifically, the proteins encoded by the following genes are up-regulated (over-expressed): ERBB2, GRB7, JNK1 kinase, BCL2, MK167, phospho-Akt, CD68 and BAG1 and the proteins encoded by the following genes are down-regulated (under expressed): Erk1 kinase, phospho-GSK-3beta, MMP11, CTSL2, CCNB1, BIRC5, STK6, MRP14 and GSTM1, in patients who are responders to irinotecan. The following reference genes may be included: ACTB, GAPD, GUSB, RPLP0 and TFRC.

Table 2 lists the genes in the present GPEP and a variant of a protein encoded thereby. Table 2 also indicates whether expression of the protein is up- or down-regulated in patients responsive to irinotecan therapy. Table 2 includes the NCBI Accession No. of a variant of each protein; other variants of these proteins exist, which can be readily ascertained by reference to an appropriate database such as NCBI Entrez. Alternate names for the proteins listed in Table 2 also can be determined from the NCBI site.

TABLE 2

| GENE NAME | PROTEIN NAME(S) | UP- OR DOWN-REGULATION of PROTEIN | NCBI Accession No. of Protein | SEQ ID NO. of Protein |
|---|---|---|---|---|
| ERBB2 | ErbB-2; HER-2 | Up | NP_004439 | 23 |
| GRB7 | GRB7; growth factor receptor-bound protein 7 | Up | NP_005301 | 24 |
| Erk1 kinase | Erk1 kinase; mitogen activated protein kinase 3 | Down | P 27361 | 25 |
| JNK1 kinase | JNK1 Kinase | Up | NP_002741 | 26 |
| BCL2 | Bcl-2; B-cell lymphoma protein 2 | Up | NP_000624 | 27 |
| GSK-3-beta | Phospho-GSK-3 beta; glycogen synthase kinase 3 beta | Down | NP_002084 | 28 |
| MMP11 | STMY3; stromolysin 3; matrix metalloproteinase 11 | Down | NP_005931 | 29 |
| CTSL2 | cathepsin L2 | Down | NP_001324 | 30 |
| CCNB1 | cyclin B1 | Down | NP_114172 | 31 |
| BIRC5 | BIRC5; survivin | Down | NP_001159 | 32 |
| MKI67 | Ki-67 antigen | Up | NP_002408 | 33 |
| STK6 | STK15; BTAK; aurora-A | Down | NP_003591 | 34 |
| Akt | Phospho-akt; v-akt murine thyoma viral oncogene; RAC protein kinase alpha | Up | NP_005154 | 35 |
| CD68 | CD68 antigen; macrosialin | Up | NP_001242 | 36 |
| BAG1 | Bcl-2 associated athanogene | Up | NP_004314 | 37 |
| GSTM1 | glutathione-s-transferase M1 | Down | NP_666533 | 38 |

TABLE 2-continued

| GENE NAME | PROTEIN NAME(S) | UP- OR DOWN-REGULATION of PROTEIN | NCBI Accession No. of Protein | SEQ ID NO. of Protein |
|---|---|---|---|---|
| ACTB | β-Actin | Up | NP_001092 | 39 |
| GAPD | GAPD | Up | NP_002037 | 40 |
| GUSB | GUS; gluuronidase beta | Up | NP_000172 | 41 |
| RPLP0 | Ribosomal protein P0 | Up | NP_000993 | 42 |
| TFRC | Transferrin receptor | Up | NP_003225 | 43 |
| MRP14 | S100 calcium binding protein A9 | Down | NP_002956 | 44 |

DEFINITIONS

For convenience, the meaning of certain terms and phrases employed in the specification, examples, and appended claims are provided below. The definitions are not meant to be limiting in nature and serve to provide a clearer understanding of certain aspects of the present invention.

The term "genome" is intended to include the entire DNA complement of an organism, including the nuclear DNA component, chromosomal or extrachromosomal DNA, as well as the cytoplasmic domain (e.g., mitochondrial DNA).

The term "gene" refers to a nucleic acid sequence that comprises control and coding sequences necessary for producing a polypeptide or precursor. The polypeptide may be encoded by a full length coding sequence or by any portion of the coding sequence. The gene may be derived in whole or in part from any source known to the art, including a plant, a fungus, an animal, a bacterial genome or episome, eukaryotic, nuclear or plasmid DNA, cDNA, viral DNA, or chemically synthesized DNA. A gene may contain one or more modifications in either the coding or the untranslated regions that could affect the biological activity or the chemical structure of the expression product, the rate of expression, or the manner of expression control. Such modifications include, but are not limited to, mutations, insertions, deletions, and substitutions of one or more nucleotides. The gene may constitute an uninterrupted coding sequence or it may include one or more introns, bound by the appropriate splice junctions. The Term "gene" as used herein includes variants of the genes identified in Table 1.

The term "gene expression" refers to the process by which a nucleic acid sequence undergoes successful transcription and translation such that detectable levels of the nucleotide sequence are expressed.

The terms "gene expression profile" or "gene signature" refer to a group of genes expressed by a particular cell or tissue type wherein presence of the genes taken together or the differential expression of such genes, is indicative/predictive of a certain condition.

The term "nucleic acid" as used herein, refers to a molecule comprised of one or more nucleotides, i.e., ribonucleotides, deoxyribonucleotides, or both. The term includes monomers and polymers of ribonucleotides and deoxyribonucleotides, with the ribonucleotides and/or deoxyribonucleotides being bound together, in the case of the polymers, via 5' to 3' linkages. The ribonucleotide and deoxyribonucleotide polymers may be single or double-stranded. However, linkages may include any of the linkages known in the art including, for example, nucleic acids comprising 5' to 3' linkages. The nucleotides may be naturally occurring or may be synthetically produced analogs that are capable of forming base-pair relationships with naturally occurring base pairs. Examples of non-naturally occurring bases that are capable of forming base-pairing relationships include, but are not limited to, aza and deaza pyrimidine analogs, aza and deaza purine analogs, and other heterocyclic base analogs, wherein one or more of the carbon and nitrogen atoms of the pyrimidine rings have been substituted by heteroatoms, e.g., oxygen, sulfur, selenium, phosphorus, and the like. Furthermore, the term "nucleic acid sequences" contemplates the complementary sequence and specifically includes any nucleic acid sequence that is substantially homologous to the both the nucleic acid sequence and its complement.

The terms "array" and "microarray" refer to the type of genes or proteins represented on an array by oligonucleotides or protein-capture agents, and where the type of genes or proteins represented on the array is dependent on the intended purpose of the array (e.g., to monitor expression of human genes or proteins). The oligonucleotides or protein-capture agents on a given array may correspond to the same type, category, or group of genes or proteins. Genes or proteins may be considered to be of the same type if they share some common characteristics such as species of origin (e.g., human, mouse, rat); disease state (e.g., cancer); functions (e.g., protein kinases;, tumor suppressors); same biological process (e.g., apoptosis, signal transduction, cell cycle regulation, proliferation, differentiation). For example, one array type may be a "cancer array" in which each of the array oligonucleotides or protein-capture agents correspond to a gene or protein associated with a cancer. An "epithelial array" may be an array of oligonucleotides or protein-capture agents corresponding to unique epithelial genes or proteins. Similarly, a "cell cycle array" may be an array type in which the oligonucleotides or protein-capture agents correspond to unique genes or proteins associated with the cell cycle.

The term "cell type" refers to a cell from a given source (e.g., a tissue, organ) or a cell in a given state of differentiation, or a cell associated with a given pathology or genetic makeup.

The term "activation" as used herein refers to any alteration of a signaling pathway or biological response including, for example, increases above basal levels, restoration to basal levels from an inhibited state, and stimulation of the pathway above basal levels.

The term "differential expression" refers to both quantitative as well as qualitative differences in the temporal and tissue expression patterns of a gene or a protein in diseased tissues or cells versus normal adjacent tissue. For example, a differentially expressed gene may have its expression activated or completely inactivated in normal versus disease conditions, or may be up-regulated (over-expressed) or down-regulated (under-expressed) in a disease condition versus a normal condition. Such a qualitatively regulated gene may exhibit an expression pattern within a given tissue or cell type that is detectable in either control or disease conditions, but is not detectable in both. Stated another way, a gene or protein is differentially expressed when expression of the gene or protein occurs at a higher or lower level in the diseased tissues or cells of a patient relative to the level of its expression in the normal (disease-free) tissues or cells of the patient and/or control tissues or cells.

The term "detectable" refers to an RNA expression pattern which is detectable via the standard techniques of polymerase chain reaction (PCR), reverse transcriptase-(RT) PCR, differential display, and Northern analyses, which are well known to those of skill in the art.

Similarly, protein expression patterns may be "detected" via standard techniques such as Western blots.

The term "complementary" refers to the topological compatibility or matching together of the interacting surfaces of a probe molecule and its target. The target and its probe can be described as complementary, and furthermore, the contact surface characteristics are complementary to each other. Hybridization or base pairing between nucleotides or nucleic acids, such as, for example, between the two strands of a double-stranded DNA molecule or between an oligonucleotide probe and a target are complementary.

The term "biological sample" refers to a sample obtained from an organism (e.g., a human patient) or from components (e.g., cells) of an organism. The sample may be of any biological tissue or fluid. The sample may be a "clinical sample" which is a sample derived from a patient. Such samples include, but are not limited to, sputum, blood, blood cells (e.g., white cells), amniotic fluid, plasma, semen, bone marrow, and tissue or fine needle biopsy samples, urine, peritoneal fluid, and pleural fluid, or cells therefrom. Biological samples may also include sections of tissues such as frozen sections taken for histological purposes. A biological sample may also be referred to as a "patient sample."

A "protein" means a polymer of amino acid residues linked together by peptide bonds. The term, as used herein, refers to proteins, polypeptides, and peptides of any size, structure, or function. Typically, however, a protein will be at least six amino acids long. If the protein is a short peptide, it will be at least about 10 amino acid residues long. A protein may be naturally occurring, recombinant, or synthetic, or any combination of these. A protein may also comprise a fragment of a naturally occurring protein or peptide. A protein may be a single molecule or may be a multi-molecular complex. The term protein may also apply to amino acid polymers in which one or more amino acid residues is an artificial chemical analogue of a corresponding naturally occurring amino acid.

A "fragment of a protein," as used herein, refers to a protein that is a portion of another protein. For example, fragments of proteins may comprise polypeptides obtained by digesting full-length protein isolated from cultured cells. In one embodiment, a protein fragment comprises at least about six amino acids. In another embodiment, the fragment comprises at least about ten amino acids. In yet another embodiment, the protein fragment comprises at least about sixteen amino acids.

As used herein, an "expression product" is a biomolecule, such as a protein, which is produced when a gene in an organism is expressed. An expression product may comprise post-translational modifications.

The term "protein expression" refers to the process by which a nucleic acid sequence undergoes successful transcription and translation such that detectable levels of the amino acid sequence or protein are expressed.

The terms "protein expression profile" or "protein expression signature" refer to a group of proteins expressed by a particular cell or tissue type (e.g., neuron, coronary artery endothelium, or disease tissue), wherein presence of the proteins taken together or the differential expression of such proteins, is indicative/predictive of a certain condition.

The term "antibody" means an immunoglobulin, whether natural or partially or wholly synthetically produced. All derivatives thereof that maintain specific binding ability are also included in the term. The term also covers any protein having a binding domain that is homologous or largely homologous to an immunoglobulin binding domain. An antibody may be monoclonal or polyclonal. The antibody may be a member of any immunoglobulin class, including any of the human classes: IgG, IgM, IgA, IgD, and IgE.

The term "antibody fragment" refers to any derivative of an antibody that is less than full-length. In one aspect, the antibody fragment retains at least a significant portion of the full-length antibody's specific binding ability, specifically, as a binding partner. Examples of antibody fragments include, but are not limited to, Fab, Fab', F(ab')$_2$, scFv, Fv, dsFv diabody, and Fd fragments. The antibody fragment may be produced by any means. For example, the antibody fragment may be enzymatically or chemically produced by fragmentation of an intact antibody or it may be recombinantly produced from a gene encoding the partial antibody sequence. Alternatively, the antibody fragment may be wholly or partially synthetically produced. The antibody fragment may comprise a single chain antibody fragment. In another embodiment, the fragment may comprise multiple chains that are linked together, for example, by disulfide linkages. The fragment may also comprise a multimolecular complex. A functional antibody fragment may typically comprise at least about 50 amino acids and more typically will comprise at least about 200 amino acids.

Determination of Gene Expression Profiles

The method used to identify and validate the present gene expression profiles indicative of whether a colon cancer patient will respond to treatment with irinotecan is described below. Other methods for identifying gene and/or protein expression profiles are known; any of these alternative methods also could be used. See, e.g., Chen et al., *NEJM*, 356 (1):11-20 (2007); Lu et al., *PLOS Med.*, 3 (12):e467 (2006); Golub et al., *Science*, 286:531-537 (1999).

The present method utilizes parallel testing in which, in one track, those genes which are over-/under-expressed as compared to normal (non-cancerous) tissue samples are identified, and, in a second track, those genes comprising chromosomal insertions or deletions as compared to normal samples are identified, from the same samples. These two tracks of analysis produce two sets of data. The data are analyzed using an algorithm which identifies the genes of the gene expression profile (i.e., those genes that are differentially expressed in cancer tissue). Positive and negative controls may be employed to normalize the results, including eliminating those genes and proteins that also are differentially expressed in normal tissues from the same patients, and confirming that the gene expression profile is unique to the cancer of interest.

In the present instance, as an initial step, biological samples were acquired from patients afflicted with colorectal cancer. Approximately five-hundred (500) tissue samples obtained from colorectal cancer patients were used, including tumor tissue and adjacent normal (undiseased) colon tissue. The tissue samples were obtained from patients suffering from various stages of colon cancer, and included those obtained from patients who have been treated with irinotecan. All of the patients were responders to irinotecan therapy. Clinical information associated with each sample, including treatment with irinotecan and the outcome of the treatment, was recorded in a database. Clinical information also includes information such as age, sex, medical history, treatment history, symptoms, family history, recurrence (yes/no), etc. Control samples, including samples of normal (non-cancerous) tissue also were acquired from the same patients. Samples of normal undiseased colon tissue from a set of healthy individuals were used as positive controls, and colon tumor samples from patients who were non-responders to irinotecan therapy were used as negative controls.

Gene expression profiles (GEPs) then were generated from the biological samples based on total RNA according to well-established methods. Briefly, a typical method involves isolating total RNA from the biological sample, amplifying the RNA, synthesizing cDNA, labeling the cDNA with a detectable label, hybridizing the cDNA with a genomic array, such as the Affymetrix U133 GeneChip®, and determining binding of the labeled cDNA with the genomic array by measuring the intensity of the signal from the detectable label bound to the array. See, e.g., the methods described in Lu, et al., Chen, et al. and Golub, et al., supra, and the references cited therein, which are incorporated herein by reference. The resulting expression data are input into a database.

MRNAs in the tissue samples can be analyzed using commercially available or customized probes or oligonucleotide arrays, such as cDNA or oligonucleotide arrays. The use of these arrays allows for the measurement of steady-state mRNA levels of thousands of genes simultaneously, thereby presenting a powerful tool for identifying effects such as the onset, arrest or modulation of uncontrolled cell proliferation. Hybridization and/or binding of the probes on the arrays to the nucleic acids of interest from the cells can be determined by detecting and/or measuring the location and intensity of the signal received from the labeled probe or used to detect a DNA/RNA sequence from the sample that hybridizes to a nucleic acid sequence at a known location on the microarray. The intensity of the signal is proportional to the quantity of cDNA or mRNA present in the sample tissue. Numerous arrays and techniques are available and useful. Methods for determining gene and/or protein expression in sample tissues are described, for example, in U.S. Pat. Nos. 6,271,002; 6,218,122; 6,218,114; and 6,004,755; and in Wang et al., *J. Clin. Oncol.*, 22 (9):1564-1671 (2004); Golub et al, (supra); and Schena et al., *Science*, 270:467-470 (1995); all of which are incorporated herein by reference.

The gene analysis aspect utilized in the present method investigates gene expression as well as insertion/deletion data. As a first step, RNA was isolated from the tissue samples and labeled. Parallel processes were run on the sample to develop two sets of data: (1) over-/under-expression of genes based on mRNA levels; and (2) chromosomal insertion/deletion data. These two sets of data were then correlated by means of an algorithm. Over-/under-expression of the genes in each cancer tissue sample were compared to gene expression in the normal (non-cancerous) samples, and a subset of genes that were differentially expressed in the cancer tissue was identified. Preferably, levels of up- and down-regulation are distinguished based on fold changes of the intensity measurements of hybridized microarray probes. A difference of about 2.0 fold or greater is preferred for making such distinctions, or a p-value of less than about 0.05. That is, before a gene is said to be differentially expressed in diseased versus normal cells, the diseased cell is found to yield at least about 2 times greater or less intensity of expression than the normal cells. Generally, the greater the fold difference (or the lower the p-value), the more preferred is the gene for use as a diagnostic or prognostic tool. Genes selected for the gene signatures of the present invention have expression levels that result in the generation of a signal that is distinguishable from those of the normal or non-modulated genes by an amount that exceeds background using clinical laboratory instrumentation.

Statistical values can be used to confidently distinguish modulated from non-modulated genes and noise. Statistical tests can identify the genes most significantly differentially expressed between diverse groups of samples. The Student's t-test is an example of a robust statistical test that can be used to find significant differences between two groups. The lower the p-value, the more compelling the evidence that the gene is showing a difference between the different groups. Nevertheless, since microarrays allow measurement of more than one gene at a time, tens of thousands of statistical tests may be asked at one time. Because of this, it is unlikely to observe small p-values just by chance, and adjustments using a Sidak correction or similar step as well as a randomization/permutation experiment can be made. A p-value less than about 0.05 by the t-test is evidence that the expression level of the gene is significantly different. More compelling evidence is a p-value less then about 0.05 after the Sidak correction is factored in. For a large number of samples in each group, a p-value less than about 0.05 after the randomization/permutation test is the most compelling evidence of a significant difference.

Another parameter that can be used to select genes that generate a signal that is greater than that of the non-modulated gene or noise is the measurement of absolute signal difference. Preferably, the signal generated by the differentially expressed genes differs by at least about 20% from those of the normal or non-modulated gene (on an absolute basis). It is even more preferred that such genes produce expression patterns that are at least about 30% different than those of normal or non-modulated genes.

This differential expression analysis can be performed using commercially available arrays, for example, Affymetrix U133 GeneChip® arrays (Affymetrix, Inc.). These arrays have probe sets for the whole human genome immobilized on the chip, and can be used to determine up- and down-regulation of genes in test samples. Other substrates having affixed thereon human genomic DNA or probes capable of detecting expression products, such as those available from Affymetrix, Agilent Technologies, Inc. or Illumina, Inc., also may be used. Currently preferred gene microarrays for use in the present invention include Affymetrix U133 GeneChip® arrays and Agilent Technologies genomic cDNA microarrays. Instruments and reagents for performing gene expression analysis are commercially available. See, e.g., Affymetrix GeneChip® System. The expression data obtained from the analysis then is input into the database.

In the second arm of the present method, chromosomal insertion/deletion data for the genes of each sample as compared to samples of normal tissue was obtained. The insertion/deletion analysis was generated using an array-based comparative genomic hybridization ("CGH"). Array CGH measures copy-number variations at multiple loci simultaneously, providing an important tool for studying cancer and developmental disorders and for developing diagnostic and therapeutic targets. Microchips for performing array CGH are commercially available, e.g., from Agilent Technologies. The Agilent chip is a chromosomal array which shows the location of genes on the chromosomes and provides additional data for the gene signature. The insertion/deletion data from this testing is input into the database.

The analyses are carried out on the same samples from the same patients to generate parallel data. The same chips and sample preparation are used to reduce variability.

The expression of certain genes known as "reference genes" "control genes" or "housekeeping genes" also is determined, preferably at the same time, as a means of ensuring the veracity of the expression profile. Reference genes are genes that are consistently expressed in many tissue types, including cancerous and normal tissues, and thus are useful to normalize gene expression profiles. See, e.g., Silvia et al., *BMC Cancer*, 6:200 (2006); Lee et al., *Genome Research*, 12 (2):292-297 (2002); Zhang et al., *BMC Mol. Biol.*, 6:4 (2005). Determining the expression of reference genes in parallel with the genes in the unique gene expression profile provides further assurance that the techniques used for determination of the gene expression profile are working properly. The expression data relating to the reference genes also is input into the database. In a currently preferred embodiment, the following genes are used as reference genes: ACTB, GAPD, GUSB, RPLP0 and/or TRFC.

Data Correlation

The differential expression data and the insertion/deletion data in the database are correlated with the clinical outcomes information associated with each tissue sample also in the database by means of an algorithm to determine a gene expression profile for determining therapeutic efficacy of irinotecan, as well as late recurrence of disease and/or disease-related death associated with irinotecan therapy. Various algorithms are available which are useful for correlating the data and identifying the predictive gene signatures. For example, algorithms such as those identified in Xu et al., A Smooth Response Surface Algorithm For Constructing A Gene Regulatory Network, *Physiol. Genomics* 11:11-20 (2002), the entirety of which is incorporated herein by reference, may be used for the practice of the embodiments disclosed herein.

Another method for identifying gene expression profiles is through the use of optimization algorithms such as the mean variance algorithm widely used in establishing stock portfolios. One such method is described in detail in the patent application U.S. Patent Application Publication No. 2003/0194734. Essentially, the method calls for the establishment of a set of inputs expression as measured by intensity) that will optimize the return (signal that is generated) one receives for using it while minimizing the variability of the return. The algorithm described in Irizarry et al., *Nucleic Acids Res.*, 31:e15 (2003)also may be used. The currently preferred algorithm is the JMP Genomics algorithm available from JMP Software.

The process of selecting gene expression profiles also may include the application of heuristic rules. Such rules are formulated based on biology and an understanding of the technology used to produce clinical results, and are applied to output from the optimization method. For example, the mean variance method of gene signature identification can be applied to microarray data for a number of genes differentially expressed in subjects with colorectal cancer. Output from the method would be an optimized set of genes that could include some genes that are expressed in peripheral blood as well as in diseased tissue. If samples used in the testing method are obtained from peripheral blood and certain genes differentially expressed in instances of cancer could also be differentially expressed in peripheral blood, then a heuristic rule can be applied in which a portfolio is selected from the efficient frontier excluding those that are differentially expressed in peripheral blood. Of course, the rule can be applied prior to the formation of the efficient frontier by, for example, applying the rule during data pre-selection.

Other heuristic rules can be applied that are not necessarily related to the biology in question. For example, one can apply a rule that only a certain percentage of the portfolio can be represented by a particular gene or group of genes. Commercially available software such as the Wagner software readily accommodates these types of heuristics (Wagner Associates Mean-Variance Optimization Application). This can be useful, for example, when factors other than accuracy and precision have an impact on the desirability of including one or more genes.

As an example, the algorithm may be used for comparing gene expression profiles for various genes (or portfolios) to ascribe prognoses. The gene expression profiles of each of the genes comprising the portfolio are fixed in a medium such as a computer readable medium. This can take a number of forms. For example, a table can be established into which the range of signals (e.g., intensity measurements) indicative of disease is input. Actual patient data can then be compared to the values in the table to determine whether the patient samples are normal or diseased. In a more sophisticated embodiment, patterns of the expression signals (e.g., fluorescent intensity) are recorded digitally or graphically. The gene expression patterns from the gene portfolios used in conjunction with patient samples are then compared to the expression patterns. Pattern comparison software can then be used to determine whether the patient samples have a pattern indicative of recurrence of the disease. Of course, these comparisons can also be used to determine whether the patient is not likely to experience disease recurrence. The expression profiles of the samples are then compared to the portfolio of a control cell. If the sample expression patterns are consistent with the expression pattern for recurrence of a colorectal cancer then (in the absence of countervailing medical considerations) the patient is treated as one would treat a relapse patient. If the sample expression patterns are consistent with the expression pattern from the normal/control cell then the patient is diagnosed negative for colorectal cancer.

A method for analyzing the gene signatures of a patient to determine prognosis of cancer is through the use of a Cox hazard analysis program. The analysis may be conducted using S-Plus software (commercially available from Insightful Corporation). Using such methods, a gene expression profile is compared to that of a profile that confidently represents relapse (i.e., expression levels for the combination of genes in the profile is indicative of relapse). The Cox hazard model with the established threshold is used to compare the similarity of the two profiles (known relapse versus patient) and then determines whether the patient profile exceeds the threshold. If it does, then the patient is classified as one who will relapse and is accorded treatment such as adjuvant therapy. If the patient profile does not exceed the threshold then they are classified as a non-relapsing patient. Other analytical tools can also be used to answer the same question such as, linear discriminate analysis, logistic regression and neural network approaches. See, e.g., software available from JMP statistical software.

Numerous other well-known methods of pattern recognition are available. The following references provide some examples:

Weighted Voting: Golub, T R., Slonim, D K., Tamaya, P., Huard, C., Gaasenbeek, M., Mesirov, J P., Coller, H., Loh, L., Downing, J R., Caligiuri, M A., Bloomfield, C D., Lander, E S. Molecular classification of cancer: class discovery and class prediction by gene expression monitoring. Science 286: 531-537, 1999.

Support Vector Machines: Su, A I., Welsh, J B., Sapinoso, L M., Kern, S G., Dimitrov, P., Lapp, H., Schultz, P G., Powell, S M., Moskaluk, C A., Frierson, H F. Jr., Hampton, G M. Molecular classification of human carcinomas by use of gene expression signatures. Cancer Research 61:7388-93, 2001. Ramaswamy, S., Tamayo, P., Rifkin, R., Mukherjee, S., Yeang, C H., Angelo, M., Ladd, C., Reich, M., Latulippe, E., Mesirov, J P., Poggio, T., Gerald, W., Loda, M., Lander, E S., Gould, T R. Multiclass cancer diagnosis using tumor gene expression signatures Proceedings of the National Academy of Sciences of the USA 98:15149-15154, 2001.

K-nearest Neighbors: Ramaswamy, S., Tamayo, P., Rifkin, R., Mukherjee, S., Yeang, C H., Angelo, M., Ladd, C., Reich, M., Latulippe, E., Mesirov, J P., Poggio, T., Gerald, W., Loda, M., Lander, E S., Gould, T R. Multiclass cancer diagnosis using tumor gene expression signatures Proceedings of the National Academy of Sciences of the USA 98:15149-15154, 2001.

Correlation Coefficients: van't Veer L J, Dai H, van de Vijver M J, He Y D, Hart A A, Mao M, Peterse H L, van der Kooy K, Marton M J, Witteveen A T, Schreiber G J, Kerkhoven R M, Roberts C, Linsley P S, Bernards R, Friend S H. Gene expression profiling predicts clinical outcome of breast cancer, Nature. 2002 Jan. 31; 415 (6871):530-6.

The gene expression analysis identifies a gene expression profile (GEP) unique to the cancer samples, that is, those genes which are differentially expressed by the cancer cells. This GEP then is validated, for example, using real-time quantitative polymerase chain reaction (RT-qPCR), which may be carried out using commercially available instruments and reagents, such as those available from Applied Biosystems.

In the present instance, the results of the gene expression analysis showed that in colon cancer patients who were responsive to treatment with irinotecan, the following genes were up-regulated: ERBB2, GRB7, JNK1 kinase, BCL2, MK167, phospho-Akt, CD-68 and BAG1, and the following genes were down-regulated: Erk1 kinase, pospho-GSK-3beta, MMP11, CTSL2, CCNB1, BIRC5, STK6, MRP14 and GSTM1, compared with expression of these genes in the normal colon tissue samples from these patients, and from the negative control patients, i.e., the tissue samples from patients that had experienced a recurrence of their cancer after treatment with irinotecan. Reference genes ACTB, GAPD, GUSB, RPLP0 and TFRC all were up-regulated.

Determination of Protein Expression Profiles

Not all genes expressed by a cell are translated into proteins, therefore, once a GEP has been identified, it is desirable to ascertain whether proteins corresponding to some or all of the differentially expressed genes in the GEP also are differentially expressed by the same cells or tissue. Therefore, protein expression profiles (PEPs) are generated from the same cancer and control tissues used to identify the GEPs. PEPs also are used to validate the GEP in other colon cancer patients.

The preferred method for generating PEPs according to the present invention is by immunohistochemistry (IHC) analysis. In this method antibodies specific for the proteins in the PEP are used to interrogate tissue samples from colon cancer patients. Other methods for identifying PEPs are known, e.g. in situ hybridization (ISH) using protein-specific nucleic acid probes. See, e.g., Hofer et al., Clin. Can. Res., 11 (16):5722 (2005); Volm et al., Clin. Exp. Metas., 19 (5):385 (2002). Any of these alternative methods also could be used.

In the present instance, samples of colon tumor tissue and normal colon tissue were obtained from patients afflicted with colon cancer who had undergone successful treatment with irinotecan; these are the same samples used for identifying the GEP. The tissue samples were arrayed on tissue microarrays (TMAs) to enable simultaneous analysis. TMAs consist of substrates, such as glass slides, on which up to about 1000 separate tissue samples are assembled in array fashion to allow simultaneous histological analysis. The tissue samples may comprise tissue obtained from preserved biopsy samples, e.g., paraffin-embedded or frozen tissues. Techniques for making tissue microarrays are well-known in the art. See, e.g., Simon et al., BioTechniques, 36 (1):98-105 (2004); Kallioniemi et al, WO 99/44062; Kononen et al., Nat. Med., 4:844-847 (1998). In the present instance, a hollow needle was used to remove tissue cores as small as 0.6 mm in diameter from regions of interest in paraffin embedded tissues. The "regions of interest" are those that have been identified by a pathologist as containing the desired diseased or normal tissue. These tissue cores then were inserted in a recipient paraffin block in a precisely spaced array pattern. Sections from this block were cut using a microtome, mounted on a microscope slide and then analyzed by standard histological analysis. Each microarray block can be cut into approximately 100 to approximately 500 sections, which can be subjected to independent tests.

The TMAs were prepared using two tissue samples from each patient: one of colon tumor tissue and one of normal colon tissue. Control arrays also were prepared; in a currently preferred embodiment, the following control TMAs were used: an array containing normal colon tissue samples from healthy, cancer-free individuals; an array of "positive controls" containing tumor tissues from cancer patients afflicted with cancers other than colon cancer, e.g., breast cancer, lung cancer, prostate cancer, etc; and an array of "negative controls" containing tumor samples from colon cancer patients that had experienced recurrences of the cancer after treatment with irinotecan—that is, patients who were "non-responders" to the therapy.

Proteins in the tissue samples may be analyzed by interrogating the TMAs using protein-specific agents, such as antibodies or nucleic acid probes, such as aptamers. Antibodies are preferred for this purpose due to their specificity and availability. The antibodies may be monoclonal or polyclonal antibodies, antibody fragments, and/or various types of synthetic antibodies, including chimeric antibodies, or fragments thereof. Antibodies are commercially available from a number of sources (e.g., Abcam, Cell Signaling Technology, Santa Cruz Biotechnology (www.santacruz.com)), or may be generated using techniques well-known to those skilled in the art. The antibodies typically are equipped with detectable labels, such as enzymes, chromogens or quantum dots that permit the antibodies to be detected. The antibodies may be conjugated or tagged directly with a detectable label, or indirectly with one member of a binding pair, of which the other member contains a detectable label. Detection systems for use with are described, for example, in the website of Ventana Medical Systems, Inc. Quantum dots are particularly useful as detectable labels. The use of quantum dots is described, for example, in the following references: Jaiswal et al., Nat. Biotechnol., 21:47-51 (2003); Chan et al., Curr. Opin. Biotechnol., 13:40-46 (2002); Chan et al., Science, 281:435-446 (1998).

The use of antibodies to identify proteins of interest in the cells of a tissue, referred to as immunohistochemistry (IHC), is well established. See, e.g., Simon et al., BioTechniques, 36(1):98 (2004); Haedicke et al., BioTechniques, 35 (1):164 (2003), which are hereby incorporated by reference. The IHC assay can be automated using commercially available instruments, such as the Benchmark instruments available from Ventana Medical Systems, Inc.

In the present instance, the TMAs were contacted with antibodies specific for the proteins encoded by the genes identified in the gene expression study as being up- or down-regulated in colon cancer patients who were responders to therapy with irinotecan in order to determine expression of these proteins in each type of tissue. The results of the IHC assay showed that in colon cancer patients who were responsive to treatment with irinotecan, the following proteins were up-regulated: ERBB2, GRB7, JNK1 kinase, BCL2, MK167, phospho-Akt, CD-68 and BAG1, and the following proteins were down-regulated: Erk1 kinase, pospho-GSK-3beta, MMP11, CTSL2, CCNB1, BIRC5, STK6, MRP14 and GSTM1, compared with expression of these proteins in the normal colon tissue samples from these patients, and in the negative control samples, i.e., colon tumor samples from patients that had experienced a recurrence of their cancer after treatment with irinotecan (non-responders). Additionally, IHC analysis showed that a majority of these proteins were not up- or down-regulated in the positive control tissue samples. The reference proteins ACTB, GAPD, GUSB, RPLP0 and TFRC all were up-regulated.

Assays

The present invention further comprises methods and assays for determining whether a colon cancer patient is likely to respond to treatment with irinotecan, and/or to predict whether the cancer is likely to recur, or disease-related death. According to one aspect, a formatted IHC assay can be used for determining if a colon cancer tumor exhibits the present GPEP. The assays may be formulated into kits that include all or some of the materials needed to conduct the analysis, including reagents (antibodies, detectable labels, etc.) and instructions.

The assay method of the invention comprises contacting a tumor sample from a colon cancer patient with a group of antibodies specific for some or all of the genes or proteins in the present GPEP, and determining the occurrence of up- or down-regulation of these genes or proteins in the sample. The use of TMAs allows numerous samples, including control samples, to be assayed simultaneously.

In a preferred embodiment, the method comprises contacting a tumor sample from a colon cancer patient and control samples with a group of antibodies specific for some or all of the proteins in the present GPEP, and determining the occurrence of up- or down-regulation of these proteins. Up-regulation of some or all of the following proteins: ERBB2, GRB7, JNK1 kinase, BCL2, MK167, phospho-Akt, CD68 and BAG1; and down-regulation of some or all of the following proteins: Erk1 kinase, phospho-GSK-3beta, MMP11, CTSL2, CCNB1, BIRC5, STK6, MRP14 and GSTM1, is indicative of the patient's responsiveness to irinotecan. Preferably, at least about four, preferably between about four and ten, and most preferably between about ten and sixteen (or more) antibodies are used in the present method.

The method preferably also includes detecting and/or quantitating control or "reference proteins". Detecting and/or quantitating the reference proteins in the samples normalizes the results and thus provides further assurance that the assay is working properly. In a currently preferred embodiment, antibodies specific for one or more of the following reference proteins are included: ACTB, GAPD, GUSB, RPLP0 and/or TRFC.

The present invention further comprises a kit containing reagents for conducting an IHC analysis of tissue samples or cells from colon cancer patients, including antibodies specific for at least four of the proteins in the GPEP and for any reference proteins. The antibodies are preferably tagged with means for detecting the binding of the antibodies to the proteins of interest, e.g., detectable labels. Preferred detectable labels include fluorescent compounds or quantum dots, however other types of detectable labels may be used. Detectable labels for antibodies are commercially available, e.g. from Ventana Medical Systems, Inc.

Immunohistochemical methods for detecting and quantitating protein expression in tissue samples are well known. Any method that permits the determination of expression of several different proteins can be used. See. e.g., Signoretti et al., "Her-2-neu Expression and Progression Toward Androgen Independence in Human Prostate Cancer," *J. Natl. Cancer Instit.*, 92 (23):1918-25 (2000); Gu et al., "Prostate stem cell antigen (PSCA) expression increases with high gleason score, advanced stage and bone metastasis in prostate cancer," *Oncogene*, 19:1288-96(2000). Such methods can be efficiently carried out using automated instruments designed for immunohistochemical (IHC) analysis. Instruments for rapidly performing such assays are commercially available, e.g., from Ventana Molecular Discovery Systems or Lab Vision Corporation. Methods according to the present invention using such instruments are carried out according to the manufacturer's instructions.

Protein-specific antibodies for use in such methods or assays are readily available or can be prepared using well-established techniques. Antibodies specific for the proteins in the GPEP disclosed herein can be obtained, for example, from Cell Signaling Technology, Inc., Santa Cruz Biotechnology, Inc. or Abcam.

The present invention is illustrated further by the following non-limiting Examples.

EXAMPLES

A series of prognostic factors were tested in order to validate the efficacy of the gene/protein expression profile (GPEP) of the present invention for predicting the therapeutic response of irinotecan therapy. The expression levels of these factors, consisting of the twenty-two (22) proteins in the present GPEP listed in Table 2 (which includes seventeen differentially expressed proteins and five reference proteins), was determined by an immunohistochemical methodology in biopsy tissue samples obtained from late-stage colon cancer patients whose treatment with irinotecan had been successful, as well as samples from patients whose treatment was unsuccessful, e.g., who had experienced late recurrence (LRec) or disease-related death (DRD) associated with the therapy. For purposes of selecting the patients for the study, irinotecan therapy was determined to have failed if a recurrence was present within three years of diagnosis.

According to the current prescribing information for CAMPTOSAR®, irinotecan currently is indicated for first line therapy of colon cancer in combination with 5-fluorouracil (5-FU) and leucovorin, or following initial 5-FU therapy in late stage colon cancer patients. The patients in the study had been treated using the combination therapy according to the prescribing information for CAMPTOSAR®.

Gene/Protein Expression Profile (GPEP):

In this study, formalin fixed paraffin embedded primary colon cancer specimens from 280 patients (median age 63 years) followed for a minimum of 120 months were evaluated for primary tumor size, histologic grade and Duke's status. These patients included only those who had been responsive to irinotecan therapy. No patients received adjuvant treatment prior to the first episode of disease recurrence. Using the techniques described above, a GPEP was generated, consisting of the following seventeen genes and encoded proteins: ERBB2, GRB7, JNK1 kinase, BCL2, MK167, phospho-Akt, CD68, BAG1, Erk1 kinase, phospho-GSK-3beta, MMP11, CTSL2, CCNB1, BIRC5, STK6, MRP14 and GSTM1, and five reference genes and proteins: ACTB, GAPD, GUSB, RPLP0 and TRFC.

Tissue microarrays were prepared using the colon adenocarcinomas and normal (non-cancerous) colon tissue from patients described above having late stage cancers who were treated with irinotecan. TMAs also were prepared containing positive and negative control samples. The TMAs used in this study are described in Table A:

TABLE A

| Tissue Micro Arrays | |
|---|---|
| Normal Screening Array | This array contained samples of normal (non-cancerous) colon tissue from 200 patients (2 samples per patient). |
| Colon Treatment Irinotecan | This array contained 280 patient samples obtained from the patients afflicted with late-stage colon adenocarcinoma who had been treated with CAMPTOSAR ® together with normal colon tissue samples from each patient. |
| Cancer Screening Survey Array (Positive control array) | This array contained 200 tumor samples for cancers other than colon cancer, including breast cancer, pancreatic cancer, prostate cancer, ovarian cancer, salivary gland cancer, lung cancer and brain tumor. |
| Colon Cancer Progression (Negative control array - TE30 array) | This array contained samples of colon cancer tissue from thirty patients who had progressed to the next stage of cancer or experienced a recurrence of cancer after treatment with CAMPTOSAR ®. |

The TMAs were constructed according to the following procedure:

Construction: An instrument was used for creating holes in a recipient paraffin block that are then filled with tissue core acquired from a selected donor block. These tissue cores were punched with a thin walled, sharpened borer. An X-Y precision guide allowed for the orderly placement of these tissue samples in an array format.

Presentation: TMA sections were cut at 4 microns and mounted on positively charged glass microslides. Individual elements are 0.6 mm in diameter, spaced 0.2 mm apart.

Elements: In addition to TMAs containing the colon cancer samples, screening and control arrays were prepared containing the tissue samples described in Table A.

Specificity: The TMAs were designed for use with specialty staining and immunohistochemical methods for gene expression screening purposes by using monoclonal and polyclonal antibodies over a wide range of characterized tissue types.

Accompanying each array was an array locator map and spreadsheet containing patient diagnostic, histologic and demographic data for each element.

Immunohistochemical (IHC) staining techniques were used for the visualization of tissue (cell) proteins present in the tissue samples on the TMAs. These techniques were based on the immunoreactivity of antibodies and the chemical properties of enzyme or enzyme complexes, which react with colorless substrate-chromogens to produce a colored end product. Initial immunoenzymatic stains utilized the direct method, which conjugated directly to an antibody with known antigenic specificity (primary antibody).

A modified labeled avidin-biotin technique was employed in which a biotinylated secondary antibody formed a complex with peroxidase-conjugated strepavidin molecules. Endogenous peroxidase activity was quenched by the addition of 3% hydrogen peroxide. The specimens then were incubate with the primary antibodies followed by sequential incubations with the biotinylated secondary link antibody (containing anti-rabbit or anti-mouse immunoglobulins) and peroidase labeled strepavidin. The primary antibody, secondary antibody, and avidin enzyme complex is then visualized utilizing a substrate-chromogen that produces a brown pigment at the antigen site that is visible by light microscopy. The antibodies utilized in this study were antibodies specific for the proteins in the present protein expression profile, i.e., ERBB2, GRB7, JNK1 kinase, BCL2, MK167, phospho-Akt, CD68, BAG1, Erk1 kinase, phospho-GSK-3beta, MMP11, CTSL2, CCNB1, BIRC5, STK6, MRP14 and GSTM1, and reference proteins ACTB, GAPD, GUSB, RPLP0 and TRFC. All antibodies were obtained from Cell Signaling Technology, Inc., and Abcam.

Automated IHC Staining Procedure:
 1. Heat-induced epitope retrieval (HIER) using 10 mM Citrate buffer solution. pH 6.0, was performed as follows:
    a. Deparaffinized and rehydrated sections were placed in a slide staining rack.
    b. The rack was placed in a microwaveable pressure cooker, 750 ml of 10 mM Citrate buffer pH 6.0 was added to cover the slides.
    c. The covered pressure cooker was placed in the microwave on high power for 15 minutes.
    d. The pressure cooker was removed from the microwave and cooled until the pressure indicator drops and the cover could be safely removed.
    e. The slides were allowed to cool to room temperature (RT), and IHC staining was carried out.
 2. Slides were treated with 3% $H_2O_2$ for 10 min. at RT to quench endogenous peroxidase activity.
 3. Slides were gently rinsed with phosphate buffered saline (PBS).
 4. The primary antibodies were applied at the predetermined dilution (according to Cell Signaling Technology's specifications) for 30 min. at RT. Normal mouse or rabbit serum 1:750 dilution was applied to negative control slides.
 5. Slides were gently rinsed with phosphate buffer saline (PBS).
 6. Secondary biotinylated link antibodies (secondary antibodies: biotinylated anti-chicken and anti-mouse immunoglobulins in phosphate buffered saline (PBS), containing carrier protein and 1.5 mM sodium azide) were applied for 30 min. at RT.
 7. Slides were rinsed with phosphate buffered saline (PBS).
 8. The slides were treated with streptavidin-HRP (streptavidin conjugated to horseradish peroxidase in PBS containing carrier protein and anti-microbial agents from Ventana.) for 30 min. at room temperature.
 9. Slides were rinsed with phosphate buffered saline (PBS).
 10. The slides were treated with substrate/chromogen (substrate-imidazole-HCl buffer pH 7.5 containing $H_2O_2$ and anti-microbial agents; DAB-3,3'-diaminobenzidine in chromogen solution from Ventana) for 10 min. at room temperature.
 11. Slides were rinsed with distilled water.
 12. Counterstain in Hematoxylin was applied for 1 min.
 13. Slides were washed in running water for 2 min.
 14. The slides were then dehydrated, cleared and the coverglass was mount.

All primary antibodies were titrated to dilutions according to the manufacturer's specifications. Staining of the TE30 test array slides (described below) was performed both with and without epitope retrieval (HIER). The slides were screened by a pathologist to determine the optimal working dilution. Pretreatment with HIER, provided strong specific staining with little to no background. The above-described IHC procedure was carried out using a Benchmark instrument from Ventana Medical Systems, Inc.

Scoring Criteria:

Staining was scored by a pathologist on a 0-3+ scale, with 0=no staining, and trace being less than 1+ but greater than 0. The scoring procedures are described in Signoretti, et al., *J. Nat. Cancer Inst.*, vol. 92 (23):1918 (December 2000) and Gu, et al., *Oncogene*, vol. 19, p. 1288 (2000). Grades of 1+ to 3+ represent increased intensity of staining with 3+ being strong, dark brown staining. Scoring criteria was also based on total percentage of staining 0=0%, 1=less than 25%, 2=25-50% and 3=greater than 50%. The percent positivity and the intensity of staining for both Nuclear and Cytoplasmic as well as sub-cellular components were analyzed. Both the intensity and percentage positive scores were multiplied to produce one number 0-9. 3+ staining was determined from known expression of the antigen from the positive controls.

Positive tissue controls were defined via standard Western Blot analysis. This experiment was performed to confirm the level of protein expression in each of the control tissues. Negative controls also were defined by the same methodology. The positive controls consisted of breast, prostate, bung, salivary gland, pancreas and ovarian adenocarcinomas and brain tumor tissue samples unrelated to the colon cancer patients who were the subjects of the study. Colon cancer tissue samples from patients who were non-responsive to irinotecan therapy (i.e., who experienced recurrence of the disease or death from the disease after treatment) were used as negative controls.

Positive expression also was evaluated using a xenograft array. SCID mice were injected with tumor cells derived from patients who were responsive to treatment with irinotecan, and the tumors were allowed to grow in the mice. Once the tumors were established, the mice were injected with 200 mg/kg of irinotecan, and the mice were monitored to observe responsiveness to the drug. As a result of treatment with irinotecan, the tumors formed in the SCID mice were reduced or eliminated. Prior to treatment with the drug, samples of the tumors were extracted from the mice and used to make a TMA. IHC assay of the TMA containing the mouse xenograft tumor tissue showed that the xenograft tumors have the same GPEP as that identified in the human patients who were responsive to irinotecan therapy.

All runs were grouped by antibody and tissue arrays which ensured that the runs were normalized, meaning that all of the tissue arrays were stained under the same conditions with the same antibody on the same run. The reproducibility was compared and validated.

Results:

Univariate analysis of GPEP profiles of the patient samples described above independently and accurately predicted response to irinotecan therapy ($p<0.0001$); late recurrence (LRec, $p<0.0005$); and disease-related death (DRD, $p<0.0001$). When stratified into GPEP negative, borderline positive and highly positive groups, patients with highly positive tumors had a relative risk (adjusted relative hazard) of irinotecan therapy response of 8.3 (range 2.1-32.4); LRec of 4.3 (range 1.7-11.0) and DRD of 11.0 (range 3.0-40.7). Tumor size and histologic grade did not predict irinotecan therapy response, LRec or DRD.

The results from this study demonstrate that in late stage colon cancer patients, GPEP positivity by immunohistochemistry accurately predicted irinotecan therapy response, late disease recurrence and disease related death independent of tumor size, grade and Duke's status. The test accurately detected ninety-two percent (92%) of non-responders to irinotecan therapy (less than 1.5% error rate or mis-classification). For determining irinotecan responsiveness, the test sensitivity rate was determined to be about ninety-six percent (96%), and the test specificity rate to be about ninety-eight percent (98%). "GPEP positivity" means that in the tumor samples from patients who were responders to irinotecan therapy, the following proteins were up-regulated: ERBB2, GRB7, JNK1 kinase, BCL2, MK167, phospho-Akt, CD-68 and BAG1, and the following genes and encoded proteins were down-regulated: Erk1 kinase, phospho-GSK-3beta, MMP11, CTSL2, CCNB1, BIRC5, STK6, MRP14 and GSTM1, compared with expression of these genes and proteins in normal colon tissue from these patients and the normal colon tissue and non-colon cancer tissues from other patients. Reference proteins ACTB, GAPD, GUSB, RPLP0 and TFRC were up-regulated in all tissues.

The results from this study are illustrated in FIG. 1. FIG. 1 is a graph showing the survival rates of colorectal cancer patients treated with irinotecan plotted against the presence of a GPEP of the invention. As shown in FIG. 1, patients with tumors having a gene expression profile in which at least sixteen of the genes in the present GPEP were differentially expressed and had the longest survival rates after treatment with irinotecan. Patients whose gene expression profile showed that ten or more of the genes in the GPEP had the next longest survival rates. The survival rates of patients whose gene expression profiles indicated that four or fewer of these genes were differentially expressed had the lowest survival rates after irinotecan therapy.

The twenty genes noted in the legend to FIG. 1 include five reference proteins.

Validation Studies

Studies using additional colon cancer biopsy tissues (from patients other than those used in the study described above) were performed to further validate the utility of the GPEP of the present invention in predicting a patient's responsiveness to irinotecan therapy. In one such study, formalin fixed paraffin embedded primary colon cancer specimens from 220 patients followed for a minimum of 120 months were evaluated for primary tumor size, histologic grade, Duke's status and expression of the proteins in the present GPEP. None of these patients received adjuvant treatment prior to the first episode of disease recurrence. The study was carried out using the same IHC methodology as described in the preceding Example, and using the same negative and positive control arrays.

Univariate analysis of GPEP profiles of the patient samples described above accurately predicted response to irinotecan therapy ($p<0.0001$); late recurrence (LRec, $p<0.0005$); and disease-related death (DRD, $p<0.0001$). When stratified into GPEP negative, borderline positive and highly positive groups, patients with highly positive tumors had a relative risk (adjusted relative hazard) of irinotecan therapy response of 6.7 (range 2.1-22.4); LRec of 3.3 (range 1.7-9.0) and DRD of 7.0 (range 3.0-30.0).

The results from this study further validates that in late stage colon cancer patients, GPEP positivity accurately predicted irinotecan therapy response, late disease recurrence and disease related death independent of tumor size, grade and Duke's status. For determining irinotecan responsiveness, the test sensitivity rate was determined to be about ninety-six percent (96%), and the test specificity rate to be about ninety-eight percent (98%).

What is claimed is:

1. A method of determining if a patient diagnosed with colon cancer is a responder to treatment with irinotecan comprising:
   a. obtaining colon cancer tissue or cells from the patient diagnosed with colon cancer
   b. determining the level of expression in the tissue or cells of: ERBB2 comprising the amino acid sequence of SEQ ID NO. 23, GRB7 comprising the amino acid sequence of SEQ ID NO. 24, JNK1 kinase comprising the amino acid sequence of SEQ ID NO. 26, BCL2 comprising the amino acid sequence of SEQ ID NO. 27, MK167 comprising the amino acid sequence of SEQ ID NO. 33, phospho-Akt comprising the amino acid sequence of SEQ ID NO. 35, CD68 comprising the amino acid sequence of SEQ ID NO. 36, BAG1 comprising the amino acid sequence of SEQ ID NO. 37, Erk1 kinase comprising the amino acid sequence of SEQ ID NO. 25, phospho-GSK-3-beta comprising the amino acid sequence of SEQ ID NO. 28, MMP11 comprising the amino acid sequence of SEQ ID NO. 29, CTSL2 comprising the amino acid sequence of SEQ ID NO. 30, CCNB1 comprising the amino acid sequence of SEQ ID NO. 31, BIRC5 comprising the amino acid sequence of SEQ ID NO. 32, STK6 comprising the amino acid sequence of SEQ ID NO. 34, MRP14 comprising the amino acid sequence of SEQ ID NO. 44 and GSTM1 comprising the amino acid sequence of SEQ ID NO. 38; and
   c. determining that the patient is a responder to treatment with irinotecan if the level of said ERBB2, said GRB7, said JNK1 kinase, said BCL2, said MK167, said phospho-Akt, said CD68 and said BAG1 is elevated in the tissue or cells as compared to the corresponding level of said ERBB2, said GRB7, said JNK1 kinase, said BCL2, said MK167, said phospho-Akt, said CD68 and said BAG1 in normal colon tissue or cells and the level of said Erk1 kinase, said phospho-GSK-3-beta, said MMP11, said CTSL2, said CCNB1, said BIRC5, said STK6, said MRP14 and said GSTM1 is lower in the tissue or cells as compared to the corresponding level of expression of said Erk1 kinase, said phospho-GSK-3-beta, said MMP11, said CTSL2, said CCNB1, said BIRC5, said STK6, said MRP14 and said GSTM1 in normal colon tissue or cells.

2. The method of claim 1 further comprising determining the level of expression of at least one reference protein in said colon cancer tissue or cells and in said normal colon tissue or cells, wherein the reference protein is ACTB comprising the amino acid sequence of SEQ ID NO. 39.

3. The method of claim 2 comprising determining the level of expression of at least one additional reference protein in said colon cancer tissue or cells and in said normal colon tissue or cells selected from the group consisting of: GAPD comprising the amino acid sequence of SEQ ID NO:40, GUSB comprising the amino acid sequence of SEQ ID NO:41, RPLP0 comprising the amino acid sequence of SEQ ID NO:42 and TFRC comprising the amino acid sequence of SEQ ID NO:43.

4. The method of claim 1 wherein step (b) is performed using immunohistochemistry.

* * * * *

```
                        SEQUENCE LISTING

<160> NUMBER OF SEQ ID NOS: 44

<210> SEQ ID NO 1
<211> LENGTH: 8704
<212> TYPE: DNA
<213> ORGANISM: Homo sapiens

<400> SEQUENCE: 1
ggaggaggtg gaggaggagg gctgcttgag gaagtataag aatgaagttg tgaagctgag      60
attcccctcc attgggaccg gagaaaccag gggagccccc cgggcagccg cgcgcccctt     120
cccacggggc cctttactgc gccgcgcgcc cggccccac ccctcgcagc accccgcgcc      180
ccgcgccctc ccagccgggt ccagccgag ccatggggcc ggagccgcag tgagcaccat      240
ggagctggcg gccttgtgcc gctggggct cctcctcgcc ctcttgcccc ccggagccgc      300
gagcacccaa gtgtgcaccg gcacagacat gaagctgcgg ctccctgcca gtcccgagac     360
ccacctggac atgctccgcc acctctacca gggctgccag gtggtgcagg gaaacctgga     420
actcacctac ctgcccacca atgccagcct gtccttcctg caggatatcc aggaggtgca     480
gggctacgtg ctcatcgctc acaaccaagt gaggcaggtc ccactgcaga ggctgcggat     540
tgtgcgaggc acccagctct ttgaggacaa ctatgccctg gccgtgctag acaatggaga     600
cccgctgaac aataccaccc ctgtcacagg ggcctcccca ggaggcctgc gggagctgca     660
gcttcgaagc ctcacagaga tcttgaaagg aggggtcttg atccagcgga accccagct     720 ctgctaccag gacacgattt tgtggaagga catcttccac aagaacaacc agctggctct     780
cacactgata gacaccaacc gctctcgggc ctgccacccc tgttctccga tgtgtaaggg     840
ctcccgctgc tggggagaga gttctgagga ttgtcagagc ctgacgcgca ctgtctgtgc     900
cggtggctgt gcccgctgca agggccact gcccactgac tgctgccatg agcagtgtgc     960
tgccggctgc acgggcccca gcactctga ctgcctggcc tgcctccact caaccacag    1020 tggcatctgt gagctgcact gcccagccct ggtcacctac aacacagaca cgtttgagtc    1080
catgcccaat cccgagggcc ggtatacatt cggcgccagc tgtgtgactg cctgtccta    1140 caactacctt tctacggacg tgggatcctg caccctcgtc tgcccctgc acaaccaaga    1200 ggtgacagca gaggatggaa cacagcggtg tgagaagtgc agcaagccct gtgcccgagt    1260
gtgctatggt ctgggcatgg agcacttgcg agaggtgagg gcagttacca gtgccaatat    1320
ccaggagttt gctggctgca agaagatctt tgggagcctg gcatttctgc cggagagctt    1380
tgatggggac ccagcctcca acactgcccc gctccagcca gagcagctcc aagtgtttga    1440
gactctggaa gagatcacag gttacctata catctcagca tggccggaca gcctgcctga    1500
cctcagcgtc ttccagaacc tgcaagtaat ccggggacga attctgcaca atggcgccta    1560
ctcgctgacc ctgcaagggc tgggcatcag ctggctgggg ctgcgctcac tgagggaact    1620
gggcagtgga ctgccctca tccaccataa cacccacctc tgcttcgtgc acacggtgcc    1680
ctgggaccag ctctttcgga acccgcacca agctctgctc cacactgcca accggccaga    1740
ggacgagtgt gtgggcgagg gcctggcctg ccaccagctg tgcgcccgag ggcactgctg    1800
gggtccaggg cccacccagt gtgtcaactg cagccagttc cttcggggcc aggagtgcgt    1860
ggaggaatgc cgagtactgc aggggctccc cagggagtat gtgaatgcca ggcactgttt    1920
```

```
gccgtgccac cctgagtgtc agccccagaa tggctcagtg acctgttttg gaccggaggc    1980
tgaccagtgt gtggcctgtg cccactataa ggaccctccc ttctgcgtgg cccgctgccc    2040
cagcggtgtg aaacctgacc tctcctacat gcccatctgg aagtttccag atgaggaggg    2100
cgcatgccag ccttgcccca tcaactgcac ccactcctgt gtggacctgg atgacaaggg    2160
ctgccccgcc gagcagagag ccagccctct gacgtccatc atctctgcgg tggttggcat    2220
tctgctggtc gtggtcttgg ggtggtcttt gggatcctc atcaagcgac ggcagcagaa     2280
gatccggaag tacacgatgc ggagactgct gcaggaaacg gagctggtgg agccgctgac    2340
acctagcgga gcgatgccca accaggcgca gatgcggatc ctgaaagaga cggagctgag    2400
gaaggtgaag gtgcttggat ctggcgcttt tggcacagtc tacaagggca tctggatccc    2460
tgatggggag aatgtgaaaa ttccagtggc catcaaagtg ttgagggaaa acacatcccc    2520
caaagccaac aaagaaatct tagacgaagc atacgtgatg gctggtgtgg gctccccata    2580
tgtctcccgc cttctgggca tctgcctgac atccacggtg cagctggtga cacagcttat    2640
gccctatggc tgcctcttag accatgtccg ggaaaaccgc ggacgcctgg gctcccagga    2700
cctgctgaac tggtgtatgc agattgccaa ggggatgagc tacctggagg atgtgcggct    2760
cgtacacagg gacttggccg ctcggaacgt gctggtcaag agtcccaacc atgtcaaaat    2820
tacagacttc gggctggctc ggctgctgga cattgacgag acagagtacc atgcagatgg    2880
gggcaaggtg cccatcaagt ggatggcgct ggagtccatt ctccgccggc ggttcacccc    2940
ccagagtgat gtgtggagtt atggtgtgac tgtgtgggag ctgatgactt ttggggccaa    3000
accttacgat gggatcccag cccgggagat ccctgacctg ctggaaaagg gggagcggct    3060
gccccagccc cccatctgca ccattgatgt ctacatgatc atggtcaaat gttggatgat    3120
tgactctgaa tgtcggccaa gattccggga gttggtgtct gaattctccc gcatggccag    3180
ggaccccag cgctttgtgg tcatccagaa tgaggacttg gcccagcca gtcccttgga     3240
cagcaccttc taccgctcac tgctggagga cgatgacatg ggggacctgg tggatgctga    3300
ggagtatctg gtaccccagc agggcttctt ctgtccagac cctgccccgg cgctggggg    3360
catggtccac cacaggcacc gcagctcatc taccaggagt ggcggtgggg acctgacact    3420
agggctggag ccctctgaag aggaggcccc caggtctcca ctggcaccct ccgaagggc     3480
tggctccgat gtatttgatg gtgacctggg aatgggggca gccaagggc tgcaaagcct     3540
ccccacacat gaccccagcc ctctacagcg gtacagtgag gacccacag tacccctgcc     3600
ctctgagact gatggctacg ttgcccccct gacctgcagc cccagcctg aatatgtgaa     3660
ccagccagat gttcggcccc agcccccttc gccccgagag ggccctctgc ctgctgcccg    3720
acctgctggt gccactctgg aaaggcccaa gactctctcc ccagggaaga tgggtcgt     3780
caaagacgtt tttgccttg ggggtgccgt ggagaaccc gagtacttga caccccaggg     3840
aggagctgcc cctcagcccc acctcctcc tgccttcagc ccagccttcg acaacctcta    3900
ttactgggac caggacccac cagagcgggg ggctccaccc agcaccttca agggacacc    3960
tacggcagag aacccagagt acctgggtct ggacgtgcca gtgtgaacca gaaggccaag    4020
tccgcagaag ccctgatgtg tcctcaggga gcagggaagg cctgacttct gctggcatca    4080
ggaggaggtg gaggaggagg gctgcttgag gaagtataag aatgaagttg tgaagctgag    4140
attcccctcc attgggaccg gagaaaccag gggagccccc cggcagccg cgcgcccctt     4200
cccacggggc cctttactgc gccgcgcgcc cggccccac ccctcgcagc accccgcgcc     4260
```

```
ccgcgccctc ccagccgggt ccagccggag ccatggggcc ggagccgcag tgagcaccat   4320
ggagctggcg gccttgtgcc gctgggggct cctcctcgcc ctcttgcccc ccggagccgc   4380
gagcacccaa gtgtgcaccg gcacagacat gaagctgcgg ctccctgcca gtcccgagac   4440
ccacctggac atgctccgcc acctctacca gggctgccag gtggtgcagg gaaacctgga   4500
actcacctac ctgcccacca atgccagcct gtccttcctg caggatatcc aggaggtgca   4560
gggctacgtg ctcatcgctc acaaccaagt gaggcaggtc ccactgcaga ggctgcggat   4620
tgtgcgaggc acccagctct ttgaggacaa ctatgccctg gccgtgctag acaatggaga   4680
cccgctgaac aataccaccc ctgtcacagg ggcctcccca ggaggcctgc gggagctgca   4740
gcttcgaagc ctcacagaga tcttgaaagg aggggtcttg atccagcgga accccccagct   4800 ctgctaccag gacacgattt tgtggaagga catcttccac aagaacaacc agctggctct   4860
cacactgata gacaccaacc gctctcgggc ctgccacccc tgttctccga tgtgtaaggg   4920
ctcccgctgc tggggagaga gttctgagga ttgtcagagc ctgacgcgca ctgtctgtgc   4980
cggtggctgt gcccgctgca aggggccact gcccactgac tgctgccatg agcagtgtgc   5040
tgccggctgc acgggcccca agcactctga ctgcctggcc tgcctccact caaccacag   5100 tggcatctgt gagctgcact gcccagccct ggtcacctac aacacagaca cgtttgagtc   5160
catgcccaat cccgagggcc ggtatacatt cggcgccagc tgtgtgactg cctgtccta   5220 caactacctt tctacggacg tgggatcctg caccctcgtc tgccccctgc acaaccaaga   5280
ggtgacagca gaggatggaa cacagcggtg tgagaagtgc agcaagccct gtcccgagt   5340 gtgctatggt ctgggcatgg agcacttgcg agaggtgagg gcagttacca gtgccaatat   5400
ccaggagttt gctggctgca agaagatctt tgggagcctg gcatttctgc cggagagctt   5460 tgatgggac ccagcctcca acactgcccc gctccagcca gagcagctcc aagtgtttga   5520
gactctggaa gagatcacag gttacctata catctcagca tggccggaca gcctgcctga   5580
cctcagcgtc ttccagaacc tgcaagtaat ccggggacga attctgcaca atggcgccta   5640
ctcgctgacc ctgcaagggc tgggcatcag ctggctgggg ctgcgctcac tgagggaact   5700
gggcagtgga ctggccctca tccaccataa cacccacctc tgcttcgtgc acacggtgcc   5760
ctgggaccag ctctttcgga acccgcacca agctctgctc cacactgcca accgccaga   5820 ggacgagtgt gtgggcgagg gcctggcctg ccaccagctg tgcgcccgag ggcactgctg   5880
gggtccaggg cccacccagt gtgtcaactg cagccagttc cttcggggcc aggagtgcgt   5940
ggaggaatgc cgagtactgc aggggctccc cagggagtat gtgaatgcca ggcactgttt   6000
gccgtgccac cctgagtgtc agccccagaa tggctcagtg acctgttttg gaccggaggc   6060
tgaccagtgt gtggcctgtg cccactataa ggaccctccc ttctgcgtgg cccgctgccc   6120
cagcggtgtg aaacctgacc tctcctacat gcccatctgg aagtttccag atgaggaggg   6180
cgcatgccag ccttgcccca tcaactgcac ccactcctgt gtggacctgg atgacaaggg   6240
ctgccccgcc gagcagagag ccagccctct gacgtccatc atctctgcgg tggttggcat   6300
tctgctggtc gtggtcttgg gggtggtctt tgggatcctc atcaagcgac ggcagcagaa   6360
gatccggaag tacacgatgc ggagactgct gcaggaaacg gagctggtgg agccgctgac   6420
acctagcgga gcgatgccca accaggcgca gatgcggatc ctgaaagaga cggagctgag   6480
gaaggtgaag gtgcttggat ctggcgcttt tggcacagtc tacaagggca tctggatccc   6540
tgatggggag aatgtgaaaa ttccagtggc catcaaagtg ttgagggaaa acacatcccc   6600
caaagccaac aaagaaatct tagacgaagc atacgtgatg gctggtgtgg gctccccata   6660
```

```
tgtctcccgc cttctgggca tctgcctgac atccacggtg cagctggtga cacagcttat   6720
gccctatggc tgcctcttag accatgtccg ggaaaaccgc ggacgcctgg gctcccagga   6780
cctgctgaac tggtgtatgc agattgccaa ggggatgagc tacctggagg atgtgcggct   6840
cgtacacagg gacttggccg ctcggaacgt gctggtcaag agtcccaacc atgtcaaaat   6900
tacagacttc gggctggctc ggctgctgga cattgacgag acagagtacc atgcagatgg   6960
gggcaaggtg cccatcaagt ggatggcgct ggagtccatt ctccgccggc ggttcaccca   7020
ccagagtgat gtgtggagtt atggtgtgac tgtgtgggag ctgatgactt ttggggccaa   7080
accttacgat gggatcccag cccgggagat ccctgacctg ctggaaaagg gggagcggct   7140
gccccagccc cccatctgca ccattgatgt ctacatgatc atggtcaaat gttggatgat   7200
tgactctgaa tgtcggccaa gattccggga gttggtgtct gaattctccc gcatggccag   7260
ggacccccag cgctttgtgg tcatccagaa tgaggacttg ggcccagcca gtcccttgga   7320
cagcaccttc taccgctcac tgctggagga cgatgacatg ggggacctgg tggatgctga   7380
ggagtatctg gtaccccagc agggcttctt ctgtccagac cctgccccgg cgctggggg   7440 catggtccac cacaggcacc gcagctcatc taccaggagt ggcggtgggg acctgacact   7500
agggctggag ccctctgaag aggaggcccc caggtctcca ctggcaccct ccgaaggggc   7560
tggctccgat gtatttgatg gtgacctggg aatgggggca gccaaggggc tgcaaagcct   7620
ccccacacat gaccccagcc ctctacagcg gtacagtgag gacccacag tacccctgcc   7680 ctctgagact gatggctacg ttgcccccct gacctgcagc cccagcctg aatatgtgaa   7740 ccagccagat gttcggcccc agccccttc gccccgagag ggccctctgc ctgctgcccg   7800
acctgctggt gccactctgg aaaggcccaa gactctctcc ccagggaaga atggggtcgt   7860
caaagacgtt tttgcctttg ggggtgccgt ggagaacccc gagtacttga caccccaggg   7920
aggagctgcc cctcagcccc accctcctcc tgccttcagc ccagccttcg acaacctcta   7980
ttactgggac caggacccac cagagcgggg ggctccaccc agcaccttca agggacacc   8040 tacggcagag aacccagagt acctgggtct ggacgtgcca gtgtgaacca gaaggccaag   8100
tccgcagaag ccctgatgtg tcctcaggga gcagggaagg cctgacttct gctggcatca   8160
agaggtggga gggccctccg accacttcca gggaacctg ccatgccagg aacctgtcct   8220
aaggaacctt ccttcctgct tgagttccca gatggctgga agggtccag cctcgttgga   8280 agaggaacag cactgggag tctttgtgga ttctgaggcc ctgcccaatg agactctagg   8340
gtccagtgga tgccacagcc cagcttggcc cttttccttcc agatcctggg tactgaaagc   8400
cttagggaag ctggcctgag aggggaagcg cccctaaggg agtgtctaag aacaaaagcg   8460
acccattcag agactgtccc tgaaacctag tactgccccc catgaggaag gaacagcaat   8520
ggtgtcagta tccaggcttt gtacagagtg cttttctgtt tagtttttac ttttttttgtt   8580 ttgttttttt aaagatgaaa taagaccca gggggagaat gggtgttgta tggggaggca   8640
agtgtggggg gtccttctcc accccactt tgtccatttg caaatatatt ttggaaaaca   8700
gcta                                                               8704
```

<210> SEQ ID NO 2
<211> LENGTH: 2260
<212> TYPE: DNA
<213> ORGANISM: Homo sapiens

<400> SEQUENCE: 2

-continued

```
ttttagtttc cttgggcctg gaatctggac acacagggct ccccccgcc tctgacttct      60
ctgtccgaag tcgggacacc ctcctaccac ctgtagagaa gcgggagtgg atctgaaata    120
aaatccagga atctgggggt tcctagacgg agccagactt cggaacgggt gtcctgctac    180
tcctgctggg gctcctccag gacaagggca cacaactggt tccgttaagc ccctctcttg    240
ctcagacgcc atggagctgg atctgtctcc acctcatctt agcagctctc cggaagacct    300
tgcccagcc cctgggaccc ctcctgggac tccccggccc cctgataccc ctctgcctga    360
ggaggtaaag aggtcccagc ctctcctcat cccaaccacc ggcaggaaac ttcgagagga    420
ggagaggcgt gccacctccc tcccctctat ccccaacccc ttccctgagc tctgcagtcc    480
tccctcacag agcccaattc tcggggccc ctccagtgca aggggctgc tcccccgcga     540
tgccagccgc cccatgtag taaaggtgta cagtgaggat ggggcctgca ggtctgtgga    600
ggtggcagca ggtgccacag ctcgccacgt gtgtgaaatg ctggtgcagc gagctcacgc    660
cttgagcgac gagacctggg ggctggtgga gtgccacccc cacctagcac tggagcgggg    720
tttggaggac cacgagtccg tggtggaagt gcaggctgcc tggcccgtgg gcggagatag    780
ccgcttcgtc ttccggaaaa acttcgccaa gtacgaactg ttcaagagct ccccacactc    840
cctgttccca gaaaaaatgg tctccagctg tctcgatgca cacactggta tatcccatga    900
agacctcatc cagaacttcc tgaatgctgg cagctttcct gagatccagg gctttctgca    960
gctgcgggt tcaggacgga agctttggaa acgctttttc tgcttcttgc gccgatctgg   1020
cctctattac tccaccaagg gcacctctaa ggatccgagg cacctgcagt acgtggcaga   1080
tgtgaacgag tccaacgtgt acgtggtgac gcagggccgc aagctctacg ggatgcccac   1140
tgacttcggt ttctgtgtca gcccaacaa gcttcgaaat ggccacaagg ggcttcggat   1200
cttctgcagt gaagatgagc agagccgcac ctgctggctg gctgccttcc gcctcttcaa   1260
gtacggggtg cagctgtaca agaattacca gcaggcacag tctcgccatc tgcatccatc   1320
ttgtttgggc tccccaccct tgagaagtgc ctcagataat accctggtgg ccatggactt   1380
ctctggccat gctgggcgtg tcattgagaa ccccgggag gctctgagtg tggccctgga   1440
ggaggcccag gcctggagga agaagacaaa ccaccgcctc agcctgccca tgccagcctc   1500
cggcacgagc ctcagtgcag ccatccaccg cacccaactc tggttccacg ggcgcatttc   1560
ccgtgaggag agccagcggc ttattggaca gcagggcttg gtagacggcc tgttcctggt   1620
ccgggagagt cagcggaacc cccagggctt tgtcctctct ttgtgccacc tgcagaaagt   1680
gaagcattat ctcatcctgc cgagcgagga ggagggccgc ctgtacttca gcatggatga   1740
tggccagacc cgcttcactg acctgctgca gctcgtggag ttccaccagc tgaaccgcgg   1800
catcctgccg tgcttgctgc gccattgctg cacgcgggtg gccctctgac caggcgtgg   1860
actggctcat gcctcagccc gccttcaggc tgcccgccgc cctccacccc atccagtgga   1920
ctctggggcg cggccacagg ggacgggatg aggagcggga gggttccgcc actccagttt   1980
tctcctctgc ttctttgcct ccctcagata gaaaacagcc cccactccag tccactcctg   2040
accctctcc tcaagggaag gccttgggtg gccccctctc cttctcctag ctctggaggt   2100
gctgctctag ggcagggaat tatgggagaa gtgggggcag cccaggcggt ttcacgcccc   2160
acactttgta cagaccgaga ggccagttga tctgctctgt tttatactag tgacaataaa   2220
gattatttt tgatacaaaa aaaaaaaaaa aaaaaaaaa                            2260
```

<210> SEQ ID NO 3
<211> LENGTH: 1866

<212> TYPE: DNA
<213> ORGANISM: Homo sapiens

<400> SEQUENCE: 3

```
cgttcctcgg cgccgccggg gccccagagg gcagcggcag caacagcagc agcagcagca      60
gcgggagtgg agatggcggc ggcggcggct caggggggcg ggggcgggga gccccgtaga     120
accgaggggg tcggcccggg ggtcccgggg gaggtggaga tggtgaaggg gcagccgttc     180
gacgtgggcc cgcgctacac gcagttgcag tacatcggcg agggcgcgta cggcatggtc     240
agctcggcct atgaccacgt gcgcaagact cgcgtggcca tcaagaagat cagccccttc     300
gaacatcaga cctactgcca gcgcacgctc cgggagatcc agatcctgct gcgcttccgc     360
catgagaatg tcatcggcat ccgagacatt ctgcgggcgt ccaccctgga agccatgaga     420
gatgtctaca ttgtgcagga cctgatggag actgacctgt acaagttgct gaaaagccag     480
cagctgagca atgaccatat ctgctacttc ctctaccaga tcctgcgggg cctcaagtac     540
atccactccg ccaacgtgct ccaccgagat ctaaagccct caacctgct cagcaacacc     600
acctgcgacc ttaagatttg tgatttcggc ctggcccgga ttgccgatcc tgagcatgac     660
cacaccggct tcctgacgga gtatgtggct acgcgctggt accgggcccc agagatcatg     720
ctgaactcca agggctatac caagtccatc gacatctggt ctgtgggctg cattctggct     780
gagatgctct ctaaccggcc catcttccct ggcaagcact acctggatca gctcaaccac     840
attctgggca tcctgggctc cccatcccag gaggacctga attgtatcat caacatgaag     900
gcccgaaact acctacagtc tctgccctcc aagaccaagg tggcttgggc caagcttttc     960
cccaagtcag actccaaagc ccttgacctg ctggaccgga tgttaacctt taaccccaat    1020
aaacggatca cagtggagga agcgctggct caccctacc tggagcagta ctatgacccg    1080
acggatgagc cagtggccga ggagcccttc accttcgcca tggagctgga tgacctacct    1140
aaggagcggc tgaaggagct catcttccag gagacagcac gcttccagcc cggagtgctg    1200
gaggccccct agcccagaca gacatctctg caccctgggg cctggacctg cctcctgcct    1260
gcccctctcc cgccagactg ttagaaaatg gacactgtgc ccagcccgga ccttggcagc    1320
ccaggccggg gtgagcatg ggcctggcca cctctctcct ttgctgaggc ctccagcttc    1380
aggcaggcca aggccttctc ctccccaccc gccctcccca cggggcctcg ggagctcagg    1440
tggccccagt tcaatctccc gctgctgctg ctgctgcgcc cttaccttcc ccagcgtccc    1500
agtctctggc agttctggaa tggaaggggtt ctggctgccc caacctgctg aagggcagag    1560
gtggagggtg gggggcgctg agtagggact cagggccatg cctgccccc tcatctcatt    1620
caaaccccac cctagtttcc ctgaaggaac attccttagt ctcaagggct agcatccctg    1680
aggagccagg ccgggccgaa tcccctccct gtcaaagctg tcacttcgcg tgccctcgct    1740
gcttctgtgt gtggtgagca gaagtggagc tgggggggcgct ggagagcccg cgcgccctgc    1800
cacctccctg acccgtctaa tatataaata tagagatgtg tctatggctg aaaaaaaaaa    1860
aaaaaa                                                               1866
```

<210> SEQ ID NO 4
<211> LENGTH: 1417
<212> TYPE: DNA
<213> ORGANISM: Homo sapiens

<400> SEQUENCE: 4

```
attaattgct tgccatcatg agcagaagca agcgtgacaa caatttttat agtgtagaga      60
```

-continued

| | |
|---|---|
| ttggagattc tacattcaca gtcctgaaac gatatcagaa tttaaaacct ataggctcag | 120 |
| gagctcaagg aatagtatgc gcagcttatg atgccattct tgaaagaaat gttgcaatca | 180 |
| agaagctaag ccgaccattt cagaatcaga ctcatgccaa gcgggcctac agagagctag | 240 |
| ttcttatgaa atgtgttaat cacaaaaata taattggcct tttgaatgtt ttcacaccac | 300 |
| agaaatccct agaagaattt caagatgttt acatagtcat ggagctcatg gatgcaaatc | 360 |
| tttgccaagt gattcagatg gagctagatc atgaaagaat gtcctacctt ctctatcaga | 420 |
| tgctgtgtgg aatcaagcac cttcattctg ctggaattat tcatcgggac ttaaagccca | 480 |
| gtaatatagt agtaaaatct gattgcactt tgaagattct tgacttcggt ctggccagga | 540 |
| ctgcaggaac gagttttatg atgacgcctt atgtagtgac tcgctactac agagcacccg | 600 |
| aggtcatcct tggcatgggc tacaaggaaa acgtggattt atggtctgtg ggtgcatta | 660 |
| tgggagaaat ggtttgccac aaaatcctct ttccaggaag ggactatatt gatcagtgga | 720 |
| ataaagttat tgaacagctt ggaacaccat gtcctgaatt catgaagaaa ctgcaaccaa | 780 |
| cagtaaggac ttacgttgaa aacagaccta atatgctgg atatagcttt gagaaactct | 840 |
| tccctgatgt cctttttccca gctgactcag aacacaacaa acttaaagcc agtcaggcaa | 900 |
| gggatttgtt atccaaaatg ctggtaatag atgcatctaa aaggatctct gtagatgaag | 960 |
| ctctccaaca cccgtacatc aatgtctggt atgatccttc tgaagcagaa gctccaccac | 1020 |
| caaagatccc tgacaagcag ttagatgaaa gggaacacac aatagaagag tggaaagaat | 1080 |
| tgatatataa ggaagttatg gacttggagg agagaaccaa gaatgagtt atacgggggc | 1140 |
| agccctctcc tttagcacag gtgcagcagt gatcaatggc tctcagcatc catcatcatc | 1200 |
| gtcgtctgtc aatgatgtgt cttcaatgtc aacagatccg actttggcct ctgatacaga | 1260 |
| cagcagtcta gaagcagcag ctgggcctct gggctgctgt agatgactac ttgggccatc | 1320 |
| gggggggtggg agggatgggg agtcggttag tcattgatag aactactttg aaaacaattc | 1380 |
| agtggtctta ttttttgggtg attttttcaaa aaatgta | 1417 |

<210> SEQ ID NO 5
<211> LENGTH: 6492
<212> TYPE: DNA
<213> ORGANISM: Homo sapiens

<400> SEQUENCE: 5

| | |
|---|---|
| tttctgtgaa gcagaagtct gggaatcgat ctggaaatcc tcctaatttt tactccctct | 60 |
| ccccgcgact cctgattcat tgggaagttt caaatcagct ataactggag agtgctgaag | 120 |
| attgatggga tcgttgcctt atgcatttgt tttggttta caaaaggaa acttgacaga | 180 |
| ggatcatgct gtacttaaaa aatacaacat cacagaggaa gtagactgat attaacaata | 240 |
| cttactaata ataacgtgcc tcatgaaata aagatccgaa aggaattgga ataaaaattt | 300 |
| cctgcatctc atgccaaggg ggaaacacca gaatcaagtg ttccgcgtga ttgaagacac | 360 |
| cccctcgtcc aagaatgcaa agcacatcca ataaaatagc tggattataa ctcctcttct | 420 |
| ttctctgggg gccgtggggt gggagctggg gcgagaggtg ccgttggccc ccgttgcttt | 480 |
| tcctctggga aggatggcgc acgctgggag aacagggtac gataaccggg agatagtgat | 540 |
| gaagtacatc cattataagc tgtcgcagag gggctacgag tgggatgcgg gagatgtggg | 600 |
| cgccgcgccc ccggggggccg ccccgcacc gggcatcttc tcctcccagc ccgggcacac | 660 |
| gccccatcca gccgcatccc gggacccggt cgccaggacc tcgccgctgc agaccccggc | 720 |
| tgcccccggc gccgccgcgg ggcctgcgct cagcccggtg ccacctgtgg tccacctgac | 780 |

```
cctccgccag gccggcgacg acttctcccg ccgctaccgc cgcgacttcg ccgagatgtc    840
cagccagctg cacctgacgc ccttcaccgc gcggggacgc tttgccacgg tggtggagga    900
gctcttcagg gacggggtga actggggag  gattgtggcc ttctttgagt tcggtggggt    960
catgtgtgtg gagagcgtca accgggagat gtcgcccctg gtggacaaca tcgccctgtg   1020
gatgactgag tacctgaacc ggcacctgca cacctggatc caggataacg gaggctggga   1080
tgcctttgtg gaactgtacg gccccagcat gcggcctctg tttgatttct cctggctgtc   1140
tctgaagact ctgctcagtt tggccctggt gggagcttgc atcaccctgg gtgcctatct   1200
gggccacaag tgaagtcaac atgcctgccc caaacaaata tgcaaaaggt tcactaaagc   1260
agtagaaata atatgcattg tcagtgatgt accatgaaac aaagctgcag gctgtttaag   1320
aaaaaataac acacatataa acatcacaca cacagacaga cacacacaca cacaacaatt   1380
aacagtcttc aggcaaaacg tcgaatcagc tatttactgc caaagggaaa tatcatttat   1440
tttttacatt attaagaaaa aaagatttat ttatttaaga cagtcccatc aaaactcctg   1500
tctttggaaa tccgaccact aattgccaag caccgcttcg tgtggctcca cctggatgtt   1560
ctgtgcctgt aaacatagat tcgctttcca tgttgttggc cggatcacca tctgaagagc   1620
agacggatgg aaaaaggacc tgatcattgg ggaagctggc tttctggctg ctggaggctg   1680
gggagaaggt gttcattcac ttgcatttct ttgccctggg ggctgtgata ttaacagagg   1740
gagggttcct gtgggggaa  gtccatgcct ccctggcctg aagaagagac tctttgcata   1800
tgactcacat gatgcatacc tggtgggagg aaaaagagttg ggaacttcag atggacctag   1860
tacccactga gatttccacg ccgaaggaca gcgatgggaa aaatgccctt aaatcatagg   1920
aaagtatttt tttaagctac caattgtgcc gagaaaagca ttttagcaat ttatacaata   1980
tcatccagta ccttaagccc tgattgtgta tattcatata ttttggatac gcacccccca   2040
actcccaata ctggctctgt ctgagtaaga aacagaatcc tctggaactt gaggaagtga   2100
acatttcggt gacttccgca tcaggaaggc tagagttacc cagagcatca ggccgccaca   2160
agtgcctgct tttaggagac cgaagtccgc agaacctgcc tgtgtcccag cttggaggcc   2220
tggtcctgga actgagccgg ggccctcact ggcctcctcc agggatgatc aacagggcag   2280
tgtggtctcc gaatgtctgg aagctgatgg agctcagaat tccactgtca agaaagagca   2340 gtagagggt  gtggctgggc ctgtcaccct ggggccctcc aggtaggccc gttttcacgt   2400
ggagcatggg agccacgacc cttcttaaga catgtatcac tgtagaggga aggaacagag   2460
gccctgggcc cttcctatca gaaggacatg gtgaaggctg ggaacgtgag gagaggcaat   2520
ggccacggcc cattttggct gtagcacatg gcacgttggc tgtgtggcct ggcccaccct   2580
gtgagtttaa agcaaggctt taaatgactt tggagagggt cacaaatcct aaaagaagca   2640
ttgaagtgag gtgtcatgga ttaattgacc cctgtctatg gaattacatg taaaacatta   2700
tcttgtcact gtagtttggt tttatttgaa aacctgacaa aaaaaaagtt ccaggtgtgg   2760
aatatggggg ttatctgtac atcctggggc attaaaaaaa aaatcaatgg tggggaacta   2820
taaagaagta acaaagaag  tgacatcttc agcaaataaa ctaggaaatt ttttttttctt   2880 ccagtttaga atcagccttg aaacattgat ggaataactc tgtggcatta ttgcattata   2940
taccatttat ctgtattaac tttggaatgt actctgttca atgttaatg  ctgtggttga   3000 tatttcgaaa gctgctttaa aaaaatacat gcatctcagc gtttttttgt ttttaattgt   3060
atttagttat ggcctataca ctatttgtga gcaaaggtga tcgttttctg tttgagattt   3120
```

```
ttatctcttg attcttcaaa agcattctga gaaggtgaga taagccctga gtctcagcta    3180
cctaagaaaa acctggatgt cactggccac tgaggagctt tgtttcaacc aagtcatgtg    3240
catttccacg tcaacagaat tgtttattgt gacagttata tctgttgtcc ctttgacctt    3300
gtttcttgaa ggtttcctcg tccctgggca attccgcatt taattcatgg tattcaggat    3360
tacatgcatg tttggttaaa cccatgagat tcattcagtt aaaaatccag atggcaaatg    3420
accagcagat tcaaatctat ggtggtttga cctttagaga gttgctttac gtggcctgtt    3480
tcaacacaga cccacccaga gccctcctgc cctccttccg cggggggcttt ctcatggctg    3540
tccttcaggg tcttcctgaa atgcagtggt gcttacgctc caccaagaaa gcaggaaacc    3600
tgtggtatga agccagacct ccccggcggg cctcagggaa cagaatgatc agacctttga    3660
atgattctaa ttttttaagca aaatattatt ttatgaaagg tttacattgt caaagtgatg    3720
aatatggaat atccaatcct gtgctgctat cctgccaaaa tcattttaat ggagtcagtt    3780
tgcagtatgc tccacgtggt aagatcctcc aagctgcttt agaagtaaca atgaagaacg    3840
tggacgtttt taatataaag cctgttttgt cttttgttgt tgttcaaacg ggattcacag    3900
agtatttgaa aaatgtatat atattaagag gtcacggggg ctaattgctg gctggctgcc    3960
ttttgctgtg gggttttgtt acctggtttt aataacagta aatgtgccca gcctcttggc    4020
cccagaactg tacagtattg tggctgcact tgctctaaga gtagttgatg ttgcattttc    4080
cttattgtta aaaacatgtt agaagcaatg aatgtatata aaagcctcaa ctagtcattt    4140
ttttctcctc ttctttttttt tcattatatc taattatttt gcagttgggc aacagagaac    4200
catccctatt ttgtattgaa gagggattca catctgcatc ttaactgctc tttatgaatg    4260
aaaaaacagt cctctgtatg tactcctctt tacactggcc agggtcagag ttaaatagag    4320
tatatgcact ttccaaattg gggacaaggg ctctaaaaaa agccccaaaa ggagaagaac    4380
atctgagaac ctcctcggcc ctcccagtcc ctcgctgcac aaatactccg caagagaggc    4440
cagaatgaca gctgacaggg tctatggcca tcgggtcgtc tccgaagatt tggcaggggc    4500
agaaaactct ggcaggctta agatttggaa taaagtcaca gaattaagga agcacctcaa    4560
tttagttcaa acaagacgcc aacattctct ccacagctca cttacctctc tgtgttcaga    4620
tgtggccttc catttatatg tgatctttgt tttattagta aatgcttatc atctaaagat    4680
gtagctctgg cccagtggga aaaattagga agtgattata atcgagagg agttataata    4740
atcaagatta aatgtaaata atcagggcaa tcccaacaca tgtctagctt tcacctccag    4800
gatctattga gtgaacagaa ttgcaaatag tctctatttg taattgaact tatcctaaaa    4860
caaatagttt ataaatgtga acttaaactc taattaattc caactgtact tttaaggcag    4920
tggctgtttt tagactttct tatcacttat agttagtaat gtacacctac tctatcagag    4980
aaaaacagga aaggctcgaa atacaagcca ttctaaggaa attagggagt cagttgaaat    5040
tctattctga tcttattctg tggtgtcttt tgcagcccag acaaatgtgg ttacacactt    5100
tttaagaaat acaattctac attgtcaagc ttatgaaggt tccaatcaga tctttattgt    5160
tattcaattt ggatctttca gggatttttt ttttaaatta ttatgggaca aaggacattt    5220
gttggagggg tgggagggag gaagaatttt taaatgtaaa acattcccaa gtttggatca    5280
gggagttgga agttttcaga ataaccagaa ctaagggtat gaaggacctg tattggggtc    5340
gatgtgatgc ctctgcgaag aaccttgtgt gacaaatgag aaacattttg aagtttgtgg    5400
tacgaccttt agattccaga gacatcagca tggctcaaag tgcagctccg tttggcagtg    5460
caatggtata aatttcaagc tggatatgtc taatgggtat ttaaacaata aatgtgcagt    5520
```

```
tttaactaac aggatattta atgcaaccct tctggttggt agggacatct gtttctaaat    5580
gtttattatg tacaatacag aaaaaaattt tataaaatta agcaatgtga aactgaattg    5640
gagagtgata atacaagtcc tttagtctta cccagtgaat cattctgttc catgtctttg    5700
gacaaccatg accttggaca atcatgaaat atgcatctca ctggatgcaa agaaaatcag    5760
atggagcatg aatggtactg taccggttca tctggactgc cccagaaaaa taacttcaag    5820
caaacatcct atcaacaaca aggttgttct gcataccaag ctgagcacag aagatgggaa    5880
cactggtgga ggatggaaag gctcgctcaa tcaagaaaat tctgagacta ttaataaata    5940
agactgtagt gtagatactg agtaaatcca tgcacctaaa cctttggaa aatctgccgt     6000 gggccctcca gatagctcat ttcattaagt ttttccctcc aaggtagaat ttgcaagagt    6060
gacagtggat tgcatttctt ttggggaagc tttcttttgg tggttttgtt tattatacct    6120
tcttaagttt tcaaccaagg tttgcttttg ttttgagtta ctggggttat ttttgttta    6180 aataaaaata agtgtacaat aagtgttttt gtattgaaag cttttgttat caagattttc    6240
atacttttac cttccatggc tctttttaag attgatactt ttaagaggtg gctgatattc    6300
tgcaacactg tacacataaa aaatacggta aggatacttt acatggttaa ggtaaagtaa    6360
gtctccagtt ggccaccatt agctataatg gcactttgtt tgtgttgttg gaaaagtca    6420 cattgccatt aaactttcct tgtctgtcta gttaatattg tgaagaaaaa taagtacag    6480 tgtgagatac tg                                                        6492

<210> SEQ ID NO 6
<211> LENGTH: 1639
<212> TYPE: DNA
<213> ORGANISM: Homo sapiens

<400> SEQUENCE: 6
atcatctata tgttaaatat ccgtgccgat ctgtcttgaa ggagaaatat atcgcttgtt      60 ttgttttta tagtatacaa aaggagtgaa aagccaagag gacgaagtct ttttcttttt     120
cttctgtggg agaacttaat gctgcattta tcgttaacct aacaccccaa cataaagaca     180
aaaggaagaa aaggaggaag gaaggaaaag gtgattcgcg aagagagtga tcatgtcagg     240
gcggcccaga accacctcct tgcggagag ctgcaagccg gtgcagcagc cttcagcttt      300
tggcagcatg aaagttagca gagacaagga cggcagcaag gtgacaacag tggtggcaac     360
tcctgggcag ggtccagaca ggccacaaga agtcagctat acagacacta aagtgattgg     420
aaatggatca tttggtgtgg tatatcaagc caaactttgt gattcaggag aactggtcgc     480
catcaagaaa gtattgcagg acaagagatt taagaatcga gagctccaga tcatgagaaa     540
gctagatcac tgtaacatag tccgattgcg ttatttcttc tactccagtg gtgagaagaa     600
agatgaggtc tatcttaatc tggtgctgga ctatgttccg gaaacagtat acagagttgc     660
cagacactat agtcgagcca acagacgct cccctgtgatt tatgtcaagt tgtatatgta     720
tcagctgttc cgaagtttag cctatatcca ttcctttgga atctgccatc gggatattaa     780
accgcagaac ctcttgttgg atcctgatac tgctgtatta aaactctgtg actttggaag     840
tgcaaagcag ctggtccgag agaacccaa tgtttcgtat atctgttctc ggtactatag     900
ggcaccagag ttgatctttg gagccactga ttatacctct agtatagatg tatggtctgc     960
tggctgtgtg ttggctgagc tgttactagg acaaccaata tttccagggg atagtggtgt    1020
ggatcagttg gtagaaataa tcaaggtcct gggaactcca acaaggggagc aaatcagaga    1080
```

| | |
|---|---|
| aatgaaccca aactacacag aatttaaatt ccctcaaatt aaggcacatc cttggactaa | 1140 |
| ggattcgtca ggaacaggac atttcacctc aggagtgcgg gtcttccgac cccgaactcc | 1200 |
| accggaggca attgcactgt gtagccgtct gctggagtat acaccaactg cccgactaac | 1260 |
| accactggaa gcttgtgcac attcattttt tgatgaatta cgggacccaa atgtcaaact | 1320 |
| accaaatggg cgagacacac ctgcactctt caacttcacc actcaagaac tgtcaagtaa | 1380 |
| tccacctctg gctaccatcc ttattcctcc tcatgctcgg attcaagcag ctgcttcaac | 1440 |
| ccccacaaat gccacagcag cgtcagatgc taatactgga gaccgtggac agaccaataa | 1500 |
| tgctgcttct gcatcagctt ccaactccac ctgaacagtc ccgagcagcc agctgcacag | 1560 |
| gaaaaaccac cagttacttg agtgtcactc agcaacactg gtcacgtttg aaagaatat | 1620 |
| taaaaaaaaa aaaaaaaa | 1639 |

<210> SEQ ID NO 7
<211> LENGTH: 2276
<212> TYPE: DNA
<213> ORGANISM: Homo sapiens

<400> SEQUENCE: 7

| | |
|---|---|
| aagcccagca gccccggggc ggatggctcc ggccgcctgg ctccgcagcg cggccgcgcg | 60 |
| cgccctcctg cccccgatgc tgctgctgct gctccagccg ccgccgctgc tggcccgggc | 120 |
| tctgccgccg gacgcccacc acctccatgc cgagaggagg gggccacagc cctggcatgc | 180 |
| agccctgccc agtagcccgg cacctgcccc tgccacgcag gaagccccc ggcctgccag | 240 |
| cagcctcagg cctccccgct gtggcgtgcc cgacccatct gatgggctga gtgcccgcaa | 300 |
| ccgacagaag aggttcgtgc tttctggcgg gcgctgggag aagacggacc tcacctacag | 360 |
| gatccttcgg ttcccatggc agttggtgca ggagcaggtg cggcagacga tggcagaggc | 420 |
| cctaaaggta tggagcgatg tgacgccact cacctttact gaggtgcacg agggccgtgc | 480 |
| tgacatcatg atcgacttcg ccaggtactg gcatggggac gacctgccgt ttgatgggcc | 540 |
| tgggggcatc ctggcccatg ccttcttccc caagactcac cgagaagggg atgtccactt | 600 |
| cgactatgat gagacctgga ctatcgggga tgaccagggc acagacctgc tgcaggtggc | 660 |
| agcccatgaa tttggccacg tgctggggct gcagcacaca acagcagcca aggccctgat | 720 |
| gtccgccttc tacacctttc gctacccact gagtctcagc ccagatgact gcaggggcgt | 780 |
| tcaaccccta tatggccagc cctggcccac tgtcacctcc aggacccag ccctgggccc | 840 |
| ccaggctggg atagacacca atgagattgc accgctggag ccagacgccc cgccagatgc | 900 |
| ctgtgaggcc tcctttgacg cggtctccac catccgaggc gagctctttt tcttcaaagc | 960 |
| gggctttgtg tggcgcctcc gtgggggcca gctgcagccc ggctaccag cattggcctc | 1020 |
| tcgccactgg cagggactgc ccagccctgt ggacgctgcc ttcgaggatg cccagggcca | 1080 |
| catttggttc ttccaaggtg ctcagtactg ggtgtacgac ggtgaaaagc cagtcctggg | 1140 |
| ccccgcaccc ctcaccgagc tgggcctggt gaggttcccg gtccatgctg ccttggtctg | 1200 |
| gggtccgag aagaacaaga tctacttctt ccgaggcagg gactactggc gtttccaccc | 1260 |
| cagcacccgg cgtgtagaca gtccgtgcc ccgcagggcc actgactgga gagggtgcc | 1320 |
| ctctgagatc gacgctgcct tccaggatgc tgatggctat gcctacttcc tgcgcggccg | 1380 |
| cctctactgg aagtttgacc ctgtgaaggt gaaggctctg gaaggcttcc cccgtctcgt | 1440 |
| gggtcctgac ttctttggct gtgccgagcc tgccaacact ttcctctgac catggcttgg | 1500 |
| atgccctcag gggtgctgac ccctgccagg ccacgaatat caggctagag acccatggcc | 1560 |

-continued

| | |
|---|---|
| atctttgtgg ctgtgggcac caggcatggg actgagccca tgtctcctca gggggatggg | 1620 |
| gtggggtaca accaccatga caactgccgg gagggccacg caggtcgtgg tcacctgcca | 1680 |
| gcgactgtct cagactgggc agggaggctt tggcatgact taagaggaag ggcagtcttg | 1740 |
| ggcccgctat gcaggtcctg gcaaacctgg ctgccctgtc tccatccctg tccctcaggg | 1800 |
| tagcaccatg gcaggactgg gggaactgga gtgtccttgc tgtatccctg ttgtgaggtt | 1860 |
| ccttccaggg gctggcactg aagcaagggt gctggggccc catggccttc agccctggct | 1920 |
| gagcaactgg gctgtagggc agggccactt cctgaggtca ggtcttggta ggtgcctgca | 1980 |
| tctgtctgcc ttctggctga caatcctgga aatctgttct ccagaatcca ggccaaaaag | 2040 |
| ttcacagtca aatggggagg ggtattcttc atgcaggaga ccccaggccc tgaggctgc | 2100 |
| aacataccte aatcctgtcc caggccggat cctcctgaag ccctttcgc agcactgcta | 2160 |
| tcctccaaag ccattgtaaa tgtgtgtaca gtgtgtataa accttcttct tcttttttt | 2220 |
| tttttaaact gaggattgtc attaaacaca gttgttttct aaaaaaaaaa aaaaaa | 2276 |

<210> SEQ ID NO 8
<211> LENGTH: 1496
<212> TYPE: DNA
<213> ORGANISM: Homo sapiens

<400> SEQUENCE: 8

| | |
|---|---|
| gctctaagcg cccggggccc cgcccagtgg ccggcacagc caatcgcagc gcggaaggc | 60 |
| ggtggggcg gggaaggccg cctggaaact taaatcccga ggcgggcgaa cctgcaccag | 120 |
| accgcggacg tctgtaatct cagaggcttg tttgctgagg gtgcctgcgc agctgcgacg | 180 |
| gctgctggtt ttgaaacatg aatctttcgc tcgtcctggc tgccttttgc ttgggaatag | 240 |
| cctccgctgt tccaaaattt gaccaaaatt tggatacaaa gtggtaccag tggaaggcaa | 300 |
| cacacagaag attatatggc gcgaatgaag aaggatggag gagagcagtg tgggaaaaga | 360 |
| atatgaaaat gattgaactg cacaatgggg aatacagcca agggaaacat ggcttcacaa | 420 |
| tggccatgaa tgcttttggt gacatgacca atgaagaatt caggcagatg atgggttgct | 480 |
| ttcgaaacca gaaattcagg aaggggaaag tgttccgtga gcctctgttt cttgatcttc | 540 |
| ccaaatctgt ggattggaga aagaaaggct acgtgacgcc agtgaagaat cagaaacagt | 600 |
| gtggttcttg ttgggctttt agtgcgactg gtgctcttga aggacagatg ttccggaaaa | 660 |
| ctgggaaact tgtctcactg agcgagcaga atctggtgga ctgttcgcgt cctcaaggca | 720 |
| atcagggctg caatggtggc ttcatggcta gggccttcca gtatgtcaag gagaacggag | 780 |
| gcctggactc tgaggaatcc tatccatatg tagcagtgga tgaaatctgt aagtacagac | 840 |
| ctgagaattc tgttgctaat gacactggct tcacagtggt cgcacctgga aaggagaagg | 900 |
| ccctgatgaa agcagtcgca actgtggggc ccatctccgt tgctatggat gcaggccatt | 960 |
| cgtccttcca gttctacaaa tcaggcattt attttgaacc agactgcagc agcaaaaacc | 1020 |
| tggatcatgt tgttctggtg gttggctacg gctttgaagg agcaaattcg aataacagca | 1080 |
| agtattggct cgtcaaaaac agctggggtc cagaatgggg ctcgaatggc tatgtaaaaa | 1140 |
| tagccaaaga caagaacaac cactgtgtaa tcgccacagc agccagctac cccaatgtgt | 1200 |
| gagctgatgg atggtgagga ggaaggactt aaggacagca tgtctgggga aattttatct | 1260 |
| tgaaactgac caaacgctta ttgtgtaaga taaaccagtt gaatcattga ggatccaagt | 1320 |
| tgagatttta attctgtgac attttacaa gggtaaaatg ttaccactac tttaattatt | 1380 |

-continued

| | |
|---|---|
| gttatacaca gctttatgat atcaaagact cattgcttaa ttctaagact tttgaatttt | 1440 |
| catttttaa aaagatgtac aaaacagttt gaaataaatt ttaattcgta tataaa | 1496 |

<210> SEQ ID NO 9
<211> LENGTH: 2101
<212> TYPE: DNA
<213> ORGANISM: Homo sapiens

<400> SEQUENCE: 9

| | |
|---|---|
| acgaacaggc caataaggag ggagcagtgc ggggtttaaa tctgaggcta ggctggctct | 60 |
| tctcggcgtg ctgcggcgga acggctgttg gtttctgctg ggtgtaggtc cttggctggt | 120 |
| cgggcctccg gtgttctgct tctccccgct gagctgctgc ctggtgaaga ggaagccatg | 180 |
| gcgctccgag tcaccaggaa ctcgaaaatt aatgctgaaa ataaggcgaa gatcaacatg | 240 |
| gcaggcgcaa agcgcgttcc tacggcccct gctgcaacct ccaagcccgg actgaggcca | 300 |
| agaacagctc ttggggacat tggtaacaaa gtcagtgaac aactgcaggc caaaatgcct | 360 |
| atgaagaagg aagcaaaacc ttcagctact ggaaaagtca ttgataaaaa actaccaaaa | 420 |
| cctcttgaaa aggtacctat gctggtgcca gtgccagtgt ctgagccagt gccagagcca | 480 |
| gaacctgagc cagaacctga gcctgttaaa aagaaaaaac tttcgcctga gcctattttg | 540 |
| gttgatactg cctctccaag cccaatggaa acatctggat gtgcccctgc agaagaagac | 600 |
| ctgtgtcagg ctttctctga tgtaattctt gcagtaaatg atgtggatgc agaagatgga | 660 |
| gctgatccaa acctttgtag tgaatatgtg aaagatattt atgcttatct gagacaactt | 720 |
| gaggaagagc aagcagtcag accaaaatac ctactgggtc gggaagtcac tggaaacatg | 780 |
| agagccatcc taattgactg gctagtacag gttcaaatga aattcaggtt gttgcaggag | 840 |
| accatgtaca tgactgtctc cattattgat cggttcatgc agaataattg tgtgcccaag | 900 |
| aagatgctgc agctggttgg tgtcactgcc atgtttattg caagcaaata tgaagaaatg | 960 |
| taccctccag aaattggtga ctttgctttt gtgactgaca cacttatac taagcaccaa | 1020 |
| atcagacaga tggaaatgaa gattctaaga gctttaaact ttggtctggg tcggcctcta | 1080 |
| cctttgcact tccttcggag agcatctaag attggagagg ttgatgtcga gcaacatact | 1140 |
| ttggccaaat acctgatgga actaactatg ttggactatg acatggtgca ctttcctcct | 1200 |
| tctcaaattg cagcaggagc tttttgctta gcactgaaaa ttctggataa tggtgaatgg | 1260 |
| acaccaactc tacaacatta cctgtcatat actgaagaat ctcttcttcc agttatgcag | 1320 |
| cacctggcta agaatgtagt catggtaaat caaggactta caaagcacat gactgtcaag | 1380 |
| aacaagtatg ccacatcgaa gcatgctaag atcagcactc taccacagct gaattctgca | 1440 |
| ctagttcaag atttagccaa ggctgtggca aaggtgtaac ttgtaaactt gagttggagt | 1500 |
| actatattta caaataaaat tggcaccatg tgccatctgt acatattact gttgcattta | 1560 |
| cttttaataa agcttgtggc cccttttact tttttatagc ttaactaatt tgaatgtggt | 1620 |
| tacttcctac tgtagggtag cggaaaagtt gtcttaaaag gtatggtggg gatattttta | 1680 |
| aaaactcctt ttggtttacc tggggatcca attgatgtat atgttatat actgggttct | 1740 |
| tgttttatat acctggcttt tactttatta atatgagtta ctgaaggtga tggaggtatt | 1800 |
| tgaaaatttt acttccatag gacatactgc atgtaagcca agtcatggag aatctgctgc | 1860 |
| atagctctat tttaaagtaa aagtctacca ccgaatccct agtcccctg ttttctgttt | 1920 |
| cttcttgtga ttgctgccat aattctaagt tatttacttt taccactatt taagttatca | 1980 |
| actttagcta gtatcttcaa actttcactt tgaaaaatga gaattttata ttctaagcca | 2040 |

```
gttttcattt tggttttgtg ttttggttaa taaaacaata ctcaaataca aaaaaaaaaa    2100
a                                                                    2101

<210> SEQ ID NO 10
<211> LENGTH: 2655
<212> TYPE: DNA
<213> ORGANISM: Homo sapiens

<400> SEQUENCE: 10
cccagaaggc cgcgggggt ggaccgccta agagggcgtg cgctcccgac atgccccgcg      60
gcgcgccatt aaccgccaga tttgaatcgc gggacccgtt ggcagaggtg gcggcggcgg    120
catgggtgcc ccgacgttgc ccctgcctg gcagcccttt ctcaaggacc accgcatctc     180
tacattcaag aactggccct tcttggaggg ctgcgcctgc accccggagc ggatggccga    240
ggctggcttc atccactgcc ccactgagaa cgagccagac ttggcccagt gtttcttctg    300
cttcaaggag ctggaaggct gggagccaga tgacgacccc atagaggaac ataaaaagca    360
ttcgtccggt tgcgctttcc tttctgtcaa gaagcagttt gaagaattaa cccttggtga    420 attttttgaaa ctggacagag aaagagccaa gaacaaaatt gcaaggaaa ccaacaataa    480 gaagaaagaa tttgaggaaa ctgcggagaa agtgcgccgt gccatcgagc agctggctgc    540
catggattga ggcctctggc cggagctgcc tggtcccaga gtggctgcac cacttccagg    600
gtttattccc tggtgccacc agccttcctg tgggcccctt agcaatgtct taggaaagga    660
gatcaacatt tcaaattag atgtttcaac tgtgctcttg ttttgtcttg aaagtggcac    720
cagaggtgct tctgcctgtg cagcgggtgc tgctggtaac agtggctgct tctctctctc    780
tctctctttt ttgggggctc attttttgctg ttttgattcc cgggcttacc aggtgagaag    840
tgagggagga agaaggcagt gtcccttttg ctagagctga cagctttgtt cgcgtgggca    900
gagccttcca cagtgaatgt gtctggacct catgttgttg aggctgtcac agtcctgagt    960
gtggacttgg caggtgcctg ttgaatctga gctgcaggtt ccttatctgt cacacctgtg   1020
cctcctcaga ggacagtttt tttgttgttg tgttttttg ttttttttt tttggtagat     1080 gcatgacttg tgtgtgatga gagaatggag acagagtccc tggctcctct actgtttaac   1140
aacatggctt tcttattttg tttgaattgt taattcacag aatagcacaa actacaatta   1200
aaactaagca caaagccatt ctaagtcatt ggggaaacgg ggtgaacttc aggtggatga   1260
ggagacagaa tagagtgata ggaagcgtct ggcagatact ccttttgcca ctgctgtgtg   1320
attagacagg cccagtgagc cgcggggcac atgctggccg ctcctccctc agaaaaaggc   1380
agtggcctaa atcctttta aatgacttgg ctcgatgctg tgggggactg gctgggctgc    1440
tgcaggccgt gtgtctgtca gcccaacctt cacatctgtc acgttctcca cacggggag    1500 agacgcagtc cgcccaggtc cccgctttct ttggaggcag cagctcccgc agggctgaag   1560
tctggcgtaa gatgatggat ttgattcgcc ctcctccctg tcatagagct gcagggtgga   1620
ttgttacagc ttcgctggaa acctctggag gtcatctcgg ctgttcctga gaataaaaaa   1680
gcctgtcatt tcaaacactg ctgtggaccc tactgggttt ttaaaatatt gtcagttttt   1740
catcgtcgtc cctagcctgc caacagccat ctgcccagac agccgcagtg aggatgagcg   1800
tcctggcaga gacgcagttg tctctgggcg cttgccagag ccacgaaccc cagacctgtt   1860
tgtatcatcc gggctccttc cgggcagaaa caactgaaaa tgcacttcag acccacttat   1920
ttctgccaca tctgagtcgg cctgagatag acttttccct ctaaactggg agaatatcac   1980
```

-continued

| | |
|---|---|
| agtggttttt gttagcagaa aatgcactcc agcctctgta ctcatctaag ctgcttattt | 2040 |
| ttgatatttg tgtcagtctg taaatggata cttcacttta ataactgttg cttagtaatt | 2100 |
| ggctttgtag agaagctgga aaaaaatggt tttgtcttca actcctttgc atgccaggcg | 2160 |
| gtgatgtgga tctcggcttc tgtgagcctg tgctgtgggc agggctgagc tggagccgcc | 2220 |
| cctctcagcc cgcctgccac ggcctttcct taaaggccat ccttaaaacc agaccctcat | 2280 |
| ggctaccagc acctgaaagc ttcctcgaca tctgttaata aagccgtagg cccttgtcta | 2340 |
| agtgcaaccg cctagacttt ctttcagata catgtccaca tgtccatttt tcaggttctc | 2400 |
| taagttggag tggagtctgg aagggttgt gaatgaggct tctgggctat gggtgaggtt | 2460 |
| ccaatggcag gttagagccc ctcgggccaa ctgccatcct ggaaagtaga cacagcagtg | 2520 |
| cccgctgccc agaagagacc agcaagccaa actggagccc ccattgcagg ctgtcgccat | 2580 |
| gtggaaagag taactcacaa ttgccaataa agtctcatgt ggtttttatct aaaaaaaaaa | 2640 |
| aaaaaaaaaa aaaaa | 2655 |

<210> SEQ ID NO 11
<211> LENGTH: 12684
<212> TYPE: DNA
<213> ORGANISM: Homo sapiens

<400> SEQUENCE: 11

| | |
|---|---|
| gcgggcgggc gggaggactc gactcggtgg gagccgctag agccgggcgc ccggggacgt | 60 |
| agcctgtagg gccaccgggt ccccgtcaga ggcggcggcg ggagcagcgg ggactgcagg | 120 |
| ccggggtgca gcgaacgcga ccccgcgggc tgcgccccgg tgtgtgcgga gcgtggcggg | 180 |
| cgcagcttac cgggcggagg tgagcgcggc gccggctcct cctgcggcgg actttgggtg | 240 |
| cgacttgacg agcggtggtt cgacaagtgg ccttgcgggc cggatcgtcc cagtggaaga | 300 |
| gttgtaaatt tgcttctggc cttccctac ggattatacc tggccttccc ctacggatta | 360 |
| tactcaactt actgtttaga aaatgtggcc cacgagacgc ctggttacta tcaaaggag | 420 |
| cggggtcgac ggtccccact ttcccctgag cctcagcacc tgcttgtttg aaggggtat | 480 |
| tgaatgtgac atccgtatcc agcttcctgt tgtgtcaaaa caacattgca aaattgaaat | 540 |
| ccatgagcag gaggcaatat tacataattt cagttccaca aatccaacac aagtaaatgg | 600 |
| gtctgttatt gatgagcctg tacggctaaa acatggagat gtaataacta ttattgatcg | 660 |
| ttccttcagg tatgaaaatg aaagtcttca gaatggaagg aagtcaactg aatttccaag | 720 |
| aaaaatacgt gaacaggagc cagcacgtcg tgtctcaaga tctagcttct cttctgaccc | 780 |
| tgatgagaaa gctcaagatt ccaaggccta ttcaaaaatc actgaaggaa aagtttcagg | 840 |
| aaatcctcag gtacatatca agaatgtcaa agaagacagt accgcagatg actcaaaaga | 900 |
| cagtgttgct cagggaacaa ctaatgttca ttcctcagaa catgctggac gtaatggcag | 960 |
| aaatgcagct gatcccattt ctggggattt taaagaaatt tccagcgtta aattagtgag | 1020 |
| ccgttatgga gaattgaagt ctgttcccac tacacaatgt cttgacaata gcaaaaaaaa | 1080 |
| tgaatctccc ttttggaagc tttatgagtc agtgaagaaa gagttggatg taaaatcaca | 1140 |
| aaagaaaat gtcctacagt attgtagaaa atctggatta caaactgatt acgcaacaga | 1200 |
| gaaagaaagt gctgatggtt tacagggga gacccaactg ttggtctcgc gtaagtcaag | 1260 |
| accaaaatct ggtgggagcg gccacgctgt ggcagagcct gcttcacctg aacaagagct | 1320 |
| tgaccagaac aaggggaagg gaagagacgt ggagtctgtt cagactccca gcaaggctgt | 1380 |
| gggcgccagc tttcctctct atgagccggc taaaatgaag acccctgtac aatattcaca | 1440 |

```
gcaacaaaat tctccacaaa aacataagaa caaagacctg tatactactg gtagaagaga   1500
atctgtgaat ctgggtaaaa gtgaaggctt caaggctggt gataaaactc ttactcccag   1560
gaagctttca actagaaatc gaacaccagc taaagttgaa gatgcagctg actctgccac   1620
taagccagaa aatctctctt ccaaaaccag aggaagtatt cctacagatg tggaagttct   1680
gcctacggaa actgaaattc acaatgagcc atttttaact ctgtggctca ctcaagttga   1740
gaggaagatc caaaaggatt ccctcagcaa gcctgagaaa ttgggcacta cagctggaca   1800
gatgtgctct gggttacctg gtcttagttc agttgatatc aacaactttg gtgattccat   1860
taatgagagt gagggaatac ctttgaaaag aaggcgtgtg tcctttggtg ggcacctaag   1920
acctgaacta tttgatgaaa acttgcctcc taatacgcct ctcaaaaggg gagaagcccc   1980
aaccaaaaga aagtctctgg taatgcacac tccacctgtc ctgaagaaaa tcatcaagga   2040
acagcctcaa ccatcaggaa aacaagagtc aggttcagaa atccatgtgg aagtgaaggc   2100
acaaagcttg gttataagcc ctccagctcc tagtcctagg aaaactccag ttgccagtga   2160
tcaacgccgt aggtcctgca aaacagcccc tgcttccagc agcaaatctc agacagaggt   2220
tcctaagaga ggagggagaa agagtggcaa cctgccttca aagagagtgt ctatcagccg   2280
aagtcaacat gatattttac agatgatatg ttccaaaaga agaagtggtg cttcggaagc   2340
aaatctgatt gttgcaaaat catgggcaga tgtagtaaaa cttggtgcaa aacaaacaca   2400
aactaaagtc ataaaacatg gtcctcaaag gtcaatgaac aaaaggcaaa gaagacctgc   2460
tactccaaag aagcctgtgg gcgaagttca cagtcaattt agtacaggcc acgcaaactc   2520
tccttgtacc ataataatag ggaaagctca tactgaaaaa gtacatgtgc ctgctcgacc   2580
ctacagagtg ctcaacaact tcatttccaa ccaaaaaatg gactttaagg aagatctttc   2640
aggaatagct gaaatgttca agaccccagt gaaggagcaa ccgcagttga caagcacatg   2700
tcacatcgct atttcaaatt cagagaattt gcttggaaaa cagtttcaag gaactgattc   2760
aggagaagaa cctctgctcc ccacctcaga gagttttgga ggaaatgtgt tcttcagtgc   2820
acagaatgca gcaaaacagc catctgataa atgtctgca agccctccct taagacggca   2880
gtgtattaga gaaaatggaa acgtagcaaa aacgcccagg aacacctaca aaatgacttc   2940
tctggagaca aaaacttcag atactgagac agagccttca aaaacagtat ccactgcaaa   3000
caggtcagga aggtctacag agttcaggaa tatacagaag ctacctgtgg aaagtaagag   3060
tgaagaaaca aatacagaaa ttgttgagtg catcctaaaa agaggtcaga aggcaacact   3120
actacaacaa aggagagaag gagagatgaa ggaaatagaa agacctttg agacatataa   3180 ggaaaatatt gaattaaaag aaaacgatga aaagatgaaa gcaatgaaga gatcaagaac   3240
ttgggggcag aaatgtgcac caatgtctga cctgacagac ctcaagagct tgcctgatac   3300
agaactcatg aaagacacgg cacgtggcca gaatctcctc caaacccaag atcatgccaa   3360
ggcaccaaag agtgagaaag gcaaaatcac taaaatgccc tgccagtcat acaaccaga   3420 accaataaac accccaacac acacaaaaca acagttgaag gcatccctgg ggaaagtagg   3480
tgtgaaagaa gagctcctag cagtcggcaa gttcacacgg acgtcagggg agaccacgca   3540
cacgcacaga gagccagcag gagatggcaa gagcatcaga acgtttaagg agtctccaaa   3600
gcagatcctg gacccagcag cccgtgtaac tggaatgaag aagtggccaa gaacgcctaa   3660
ggaagaggcc cagtcactag aagacctggc tggcttcaaa gagctcttcc agacaccagg   3720
tccctctgag gaatcaatga ctgatgagaa aactaccaaa atagcctgca aatctccacc   3780
```

```
accagaatca gtggacactc caacaagcac aaagcaatgg cctaagagaa gtctcaggaa    3840
agcagatgta gaggaagaat tcttagcact caggaaacta acaccatcag cagggaaagc    3900
catgcttacg cccaaaccag caggaggtga tgagaaagac attaaagcat ttatgggaac    3960
tccagtgcag aaactggacc tggcaggaac tttacctggc agcaaaagac agctacagac    4020
tcctaaggaa aaggcccagg ctctagaaga acctggctgg ctttaaagag ctcttccagac   4080 tcctggtcac accgaggaat tagtggctgc tggtaaaacc actaaaatac cctgcgactc    4140
tccacagtca gacccagtgg acaccccaac aagcacaaag caacgaccca agagaagtat    4200
caggaaagca gatgtagagg gagaactctt agcgtgcagg aatctaatgc catcagcagg    4260
caaagccatg cacacgccta aaccatcagt aggtgaagag aaagacatca tcatatttgt    4320
gggaactcca gtgcagaaac tggacctgac agagaactta accggcagca agagacggcc    4380
acaaactcct aaggaagagg cccaggctct ggaagacctg actggcttta aagagctctt    4440 ccagaccct ggtcatactg aagaagcagt ggctgctggc aaaactacta aaatgccctg    4500
cgaatcttct ccaccagaat cagcagacac cccaacaagc aagaaggc agcccaagac    4560 acctttggag aaaagggacg tacagaagga gctctcagcc ctgaagaagc tcacacagac    4620
atcaggggaa accacacaca cagataaagt accaggaggt gaggataaaa gcatcaacgc    4680 gtttaggga actgcaaaac agaaactgga cccagcagca agtgtaactg gtagcaagag    4740
gcacccaaaa actaaggaaa aggcccaacc cctagaagac ctggctggct tgaaagagct    4800
cttccagaca ccagtatgca ctgacaagcc cacgactcac gagaaaacta ccaaaatagc    4860
ctgcagatca caaccagacc cagtggacac accaacaagc tccaagccac agtccaagag    4920
aagtctcagg aaagtggacg tagaagaaga attcttcgca ctcaggaaac gaacaccatc    4980
agcaggcaaa gccatgcaca cacccaaacc agcagtaagt ggtgagaaaa acatctacgc    5040
atttatggga actccagtgc agaaactgga cctgacagag aacttaactg gcagcaagag    5100
acggctacaa actcctaagg aaaaggccca ggctctagaa gacctggctg ctttaaaga    5160 gctcttccag acacgaggtc acactgagga atcaatgact aacgataaaa ctgccaaagt    5220
agcctgcaaa tcttcacaac cagacccaga caaaaaccca gcaagctcca agcgacggct    5280
caagacatcc ctggggaaag tgggcgtgaa agaagagctc ctagcagttg gcaagctcac    5340
acagacatca ggagagacta cacacacaca cacgagcca acaggagatg gtaagagcat    5400
gaaagcattt atggagtctc caaagcagat cttagactca gcagcaagtc taactggcag    5460
caagaggcag ctgagaactc ctaagggaaa gtctgaagtc cctgaagacc tggccggctt    5520
catcgagctc ttccagacac caagtcacac taaggaatca atgactaacg aaaaaactac    5580
caaagtatcc tacagagctt cacagccaga cctagtggaa accccaacaa gctccaagcc    5640
acagcccaag agaagtctca ggaaagcaga cactgaagaa gattttttag catttaggaa    5700
acaaacgcca tcagcaggca aagccatgca cacccaaaa ccagcagtag gtgaagagaa    5760
agacatcaac acgttttgg gaactccagt gcagaaactg accagccag gaaatttacc    5820 tggcagcaat agacggctac aaactcgtaa ggaaaaggcc caggctctag aagaactgac    5880
tggcttcaga gagcttttcc agacaccatg cactgataac cccacgactg atgagaaaac    5940
taccaaaaaa atactctgca aatctccgca atcagcccca gcgacaccc caacaaacac    6000 aaagcaacgg cccaagagaa gcctcaagaa agcagacgta gaggaagaat ttttagcatt    6060
caggaaacta acaccatcag caggcaaagc catgcacacg cctaaagcag cagtaggtga    6120
agagaaagac atcaacacat tgtggggac tccagtggag aaactggacc tgctaggaaa    6180
```

```
tttacctggc agcaagagac ggccacaaac tcctaaagaa aaggccaagg ctctagaaga    6240
tctggctggc ttcaaagagc tcttccagac accaggtcac actgaggaat caatgaccga    6300
tgacaaaatc acagaagtat cctgcaaatc tccacaacca gacccagtca aaacccccaac   6360
aagctccaag caacgactca agatatcctt ggggaaagta ggtgtgaaag aagaggtcct    6420
accagtcggc aagctcacac agacgtcagg gaagaccaca cagacacaca gagagacagc    6480
aggagatgga aagagcatca aagcgtttaa ggaatctgca aagcagatgc tggacccagc    6540
aaactatgga actgggatgg agaggtggcc aagaacacct aaggaagagg cccaatcact    6600
agaagacctg gccggcttca aagagctctt ccagacacca gaccacactg aggaatcaac    6660
aactgatgac aaaactacca aaatagcctg caaatctcca ccaccagaat caatggacac    6720
tccaacaagc acaaggaggc ggcccaaaac acctttgggg aaagggata tagtggaaga     6780
gctctcagcc ctgaagcagc tcacacagac cacacacaca gacaaagtac caggagatga    6840
ggataaaggc atcaacgtgt tcagggaaac tgcaaacag aaactggacc cagcagcaag     6900
tgtaactggt agcaagaggc agccaagaac tcctaaggga aaagcccaac ccctagaaga    6960
cttggctggc ttgaaagagc tcttccagac accaatatgc actgacaagc ccacgactca    7020
tgagaaaact accaaaatag cctgcagatc tccacaacca gacccagtgg gtaccccaac    7080
aatcttcaag ccacagtcca agagaagtct caggaaagca gacgtagagg aagaatcctt    7140
agcactcagg aaacgaacac catcagtagg gaaagctatg gacacaccca accagcagg    7200
aggtgatgag aaagacatga aagcatttat gggaactcca gtgcagaaat tggacctgcc    7260
aggaaattta cctggcagca aaagatggcc acaaactcct aaggaaaagg cccaggctct    7320
agaagacctg gctggcttca aagagctctt ccagacacca ggcactgaca gcccacgac    7380
tgatgagaaa actaccaaaa tagcctgcaa atctccacaa ccagaccag tggacacccc     7440
agcaagcaca aagcaacggc ccaagagaaa cctcaggaaa gcagacgtag aggaagaatt    7500
tttagcactc aggaaacgaa caccatcagc aggcaaagcc atggacacac caaaaccagc    7560
agtaagtgat gagaaaaata tcaacacatt tgtggaaact ccagtgcaga aactggacct    7620
gctaggaaat ttacctggca gcaagagaca gccacagact cctaaggaaa aggctgaggc    7680
tctagaggac ctggttggct tcaaagaact cttccagaca ccaggtcaca ctgaggaatc    7740
aatgactgat gacaaaatca cagaagtatc ctgtaaatct ccacagccag agtcattcaa    7800
aacctcaaga agctccaagc aaaggctcaa gatacccctg gtgaaagtgg acatgaaaga    7860
agagccccta gcagtcagca agctcacacg gacatcaggg gagactacgc aaacacacac    7920
agagccaaca ggagatagta agagcatcaa agcgtttaag gagtctccaa agcagatcct    7980
ggacccagca gcaagtgtaa ctggtagcag gaggcagctg agaactcgta aggaaaaggc    8040
ccgtgctcta gaagacctgg ttgacttcaa agagctcttc tcagcaccag gtcacactga    8100
agagtcaatg actattgaca aaaacacaaa aattccctgc aaatctcccc caccagaact    8160
aacagacact gccacgagca caagagatg cccaagaca cgtcccagga agaagtaaa       8220
agaggagctc tcagcagttg agaggctcac gcaaacatca gggcaaagca cacacacaca    8280
caaagaacca gcaagcggtg atgagggcat caaagtattg aagcaacgtg caaagaagaa    8340
accaaacccca gtagaagagg aacccagcag gagaaggcca agagcaccta aggaaaaggc    8400
ccaaccccctg gaagacctgg ccggcttcac agagctctct gaaacatcag gtcacactca    8460
ggaatcactg actgctggca aagccactaa aatacccttgc gaatctcccc cactagaagt    8520
```

```
ggtagacacc acagcaagca caaagaggca tctcaggaca cgtgtgcaga aggtacaagt    8580
aaaagaagag ccttcagcag tcaagttcac acaaacatca ggggaaacca cggatgcaga    8640
caaagaacca gcaggtgaag ataaaggcat caaagcattg aaggaatctg caaaacagac    8700
accggctcca gcagcaagtg taactggcag caggagacgg ccaagagcac ccagggaaag    8760
tgcccaagcc atagaagacc tagctggctt caaagaccca gcagcaggtc acactgaaga    8820
atcaatgact gatgacaaaa ccactaaaat accctgcaaa tcatcaccag aactagaaga    8880
caccgcaaca agctcaaaga dacggcccag dacacgtgcc cagaaagtag aagtgaagga    8940
ggagctgtta gcagttggca agctcacaca aacctcaggg gagaccacgc acaccgacaa    9000
agagccggta ggtgagggca aaggcacgaa agcatttaag caacctgcaa agcggaagct    9060
ggacgcagaa gatgtaattg gcagcaggag acagccaaga gcacctaagg aaaaggccca    9120
accctggaa gatctggcca gcttccaaga gctctctcaa acaccaggcc acactgagga    9180
actggcaaat ggtgctgctg atagctttac aagcgctcca aagcaaacac ctgacagtgg    9240
aaaacctcta aaatatccga aagagttct tcgggcccct aaagtagaac cgtgggaga    9300
cgtggtaagc accagagacc ctgtaaaatc acaaagcaaa agcaacactt ccctgccccc    9360
actgccccttc aagaggggag gtggcaaaga tggaagcgtc acgggaacca agaggctgcg    9420
ctgcatgcca gcaccagagg aaattgtgga ggagctgcca gccagcaaga agcagagggt    9480
tgctcccagg gcaagaggca aatcatccga accgtggtc atcatgaaga gaagtttgag    9540
gacttctgca aaaagaattg aacctgcgga gagctgaac agcaacgaca tgaaaaccaa    9600
caaagaggaa cacaaattac aagactcggt ccctgaaaat aagggaatat ccctgcgctc    9660
cagacgccaa aataagactg aggcagaaca gcaaataact gaggtctttg tattagcaga    9720
aagaatagaa ataaacagaa atgaaaagaa gcccatgaag acctccccag agatggacat    9780
tcagaatcca gatgatggag cccggaaacc catacctaga gacaaagtca ctgagaacaa    9840
aaggtgcttg aggtctgcta gacagaatga gagctcccag cctaaggtgg cagaggagag    9900
cggagggcag aagagtgcga aggttctcat gcagaatcag aaagggaaag agaagcagg    9960
aaattcagac tccatgtgcc tgagatcaag aaagacaaaa agccagcctg cagcaagcac    10020
tttggagagc aaatctgtgc agagagtaac gcggagtgtc aagaggtgtg cagaaaatcc    10080
aaagaaggct gaggacaatg tgtgtgtcaa gaaaataaga accagaagtc atagggacag    10140
tgaagatatt tgacagaaaa atcgaactgg gaaaaatata ataaagttag ttttgtgata    10200
agttctagtg cagtttttgt cataaattac aagtgaattc tgtaagtaag gctgtcagtc    10260
tgcttaaggg aagaaaactt tggatttgct gggtctgaat cggcttcata aactccactg    10320
ggagcactgc tgggctcctg gactgagaat agttgaacac cggggctttt gtgaaggagt    10380
ctgggccaag gtttgccctc agctttgcag aatgaagcct tgaggtctgt caccacccac    10440
agccacccta cagcagcctt aactgtgaca cttgccacac tgtgtcgtcg tttgtttgcc    10500
tatgtcctcc agggcacggt ggcaggaaca actatcctcg tctgtcccaa cactgagcag    10560
gcactcggta aacacgaatg aatggatgag cgcacggatg aatggagctt acaagatctg    10620
tcttttccaat ggccgggggc atttggtccc caaattaagg ctattggaca tctgcacagg    10680
acagtcctat ttttgatgtc ctttcctttc tgaaaataaa gttttgtgct ttggagaatg    10740
actcgtgagc acatctttag ggaccaagag tgactttctg taaggagtga ctcgtggctt    10800
gccttggtct cttgggaata cttttctaac tagggttgct ctcacctgag acattctcca    10860
cccgcggaat ctcagggtcc caggctgtgg gccatcacga cctcaaactg ctcctaatc    10920
```

| | |
|---|---|
| tccagctttc ctgtcattga aagcttcgga agtttactgg ctctgctccc gcctgttttc | 10980 |
| tttctgactc tatctggcag cccgatgcca cccagtacag gaagtgacac cagtactctg | 11040 |
| taaagcatca tcatccttgg agagactgag cactcagcac cttcagccac gatttcagga | 11100 |
| tcgcttcctt gtgagccgct gcctccgaaa tctcctttga agcccagaca tctttctcca | 11160 |
| gcttcagact tgtagatata actcgttcat cttcatttac tttccacttt gcccctgtc | 11220 |
| ctctctgtgt tccccaaatc agagaatagc ccgccatccc ccaggtcacc tgtctggatt | 11280 |
| cctccccatt cacccacctt gccaggtgca ggtgaggatg gtgcaccaga cagggtagct | 11340 |
| gtcccccaaa atgtgccctg tgcgggcagt gccctgtctc cacgtttgtt tccccagtgt | 11400 |
| ctggcgggga gccaggtgac atcataaata cttgctgaat gaatgcagaa atcagcggta | 11460 |
| ctgacttgta ctatattggc tgccatgata gggttctcac agcgtcatcc atgatcgtaa | 11520 |
| gggagaatga cattctgctt gagggaggga atagaaaggg gcaggagggg acatctgag | 11580 |
| ggcttcacag ggctgcaaag ggtacaggga ttgcaccagg gcagaacagg ggagggtgtt | 11640 |
| caaggaagag tggctcttag cagaggcact ttggaaggtg tgaggcataa atgcttcctt | 11700 |
| ctacgtaggc caacctcaaa actttcagta ggaatgttgc tatgatcaag ttgttctaac | 11760 |
| actttagact tagtagtaat tatgaacctc acatagaaaa atttcatcca gccatatgcc | 11820 |
| tgtggagtgg aatattctgt ttagtagaaa aatcctttag agttcagctc taaccagaaa | 11880 |
| tcttgctgaa gtatgtcagc accttttctc accctggtaa gtacagtatt tcaagagcac | 11940 |
| gctaagggtg gttttcattt tacagggctg ttgatgatgg gttaaaaatg ttcatttaag | 12000 |
| ggctaccccc gtgtttaata gatgaacacc acttctacac aaccctcctt ggtactgggg | 12060 |
| gagggagaga tctgacaaat actgcccatt cccctaggct gactggattt gagaacaaat | 12120 |
| acccacccat ttccaccatg gtatggtaac ttctctgagc ttcagtttcc aagtgaattt | 12180 |
| ccatgtaata ggacattccc attaaataca agctgttttt acttttttcgc ctcccagggc | 12240 |
| ctgtgggatc tggtccccca gcctctcttg ggctttctta cactaactct gtacctacca | 12300 |
| tctcctgcct cccttaggca ggcacctcca accaccacac actccctgct gttttccctg | 12360 |
| cctggaactt tccctcctgc cccaccaaga tcatttcatc cagtcctgag ctcagcttaa | 12420 |
| gggaggcttc ttgcctgtgg gttccctcac ccccatgcct gtcctccagg ctggggcagg | 12480 |
| ttcttagttt gcctggaatt gttctgtacc tctttgtagc acgtagtgtt gtggaaacta | 12540 |
| agccactaat tgagtttctg gctcccctcc tggggttgta agttttgttc attcatgagg | 12600 |
| gccgactgca tttcctggtt actctatccc agtgaccagc cacaggagat gtccaataaa | 12660 |
| gtatgtgatg aaatggtctt aaaa | 12684 |

<210> SEQ ID NO 12
<211> LENGTH: 2346
<212> TYPE: DNA
<213> ORGANISM: Homo sapiens

<400> SEQUENCE: 12

| | |
|---|---|
| acaaggcagc ctcgctcgag cgcaggccaa tcggctttct agctagaggg tttaactcct | 60 |
| atttaaaaag aagaaccttt gaattctaac ggctgagctc ttggaagact tgggtccttg | 120 |
| ggtcgcaggt gggagccgac gggtgggtag accgtggggg atatctcagt ggcggacgag | 180 |
| gacggcgggg acaaggggcg gctggtcgga gtggcggagc gtcaagtccc ctgtcggttc | 240 |
| ctccgtccct gagtgtcctt ggcgctgcct tgtgcccgcc cagcgccttt gcatccgctc | 300 |

-continued

```
ctgggcaccg aggcgccctg taggatactg cttgttactt attacagcta gaggcatcat      360
ggaccgatct aaagaaaact gcatttcagg acctgttaag gctacagctc cagttggagg      420
tccaaaacgt gttctcgtga ctcagcaatt tccttgtcag aatccattac ctgtaaatag      480
tggccaggct cagcgggtct tgtgtccttc aaattcttcc cagcgcattc ctttgcaagc      540
acaaaagctt gtctccagtc acaagccggt tcagaatcag aagcagaagc aattgcaggc      600
aaccagtgta cctcatcctg tctccaggcc actgaataac acccaaaaga gcaagcagcc      660
cctgccatcg gcacctgaaa ataatcctga ggaggaactg gcatcaaaac agaaaaatga      720
agaatcaaaa aagaggcagt gggctttgga agactttgaa attggtcgcc ctctgggtaa      780
aggaaagttt ggtaatgttt atttggcaag agaaaagcaa agcaagttta ttctggctct      840
taaagtgtta tttaaagctc agctggagaa agccggagtg gagcatcagc tcagaagaga      900
agtagaaata cagtcccacc ttcggcatcc taatattctt agactgtatg gttatttcca      960
tgatgctacc agagtctacc taattctgga atatgcacca cttggaacag tttatagaga     1020
acttcagaaa ctttcaaagt tgatgagca gagaactgct acttatataa cagaattggc     1080
aaatgccctg tcttactgtc attcgaagag agttattcat agagacatta agccagagaa     1140
cttacttctt ggatcagctg gagagcttaa aattgcagat tttgggtggt cagtacatgc     1200
tccatcttcc aggaggacca ctctctgtgg caccctggac tacctgcccc ctgaaatgat     1260
tgaaggtcgg atgcatgatg agaaggtgga tctctggagc cttggagttc tttgctatga     1320
atttttagtt gggaagcctc cttttgaggc aaacacatac caagagacct acaaaagaat     1380
atcacgggtt gaattcacat tccctgactt tgtaacagag ggagccaggg acctcatttc     1440
aagactgttg aagcataatc ccagccagag gccaatgctc agagaagtac ttgaacaccc     1500
ctggatcaca gcaaattcat caaaaccatc aaattgccaa aacaaagaat cagctagcaa     1560
acagtcttag gaatcgtgca gggggagaaa tccttgagcc agggctgcca tataacctga     1620
caggaacatg ctactgaagt ttattttacc attgactgct gccctcaatc tagaacgcta     1680
cacaagaaat atttgtttta ctcagcaggt gtgccttaac ctccctattc agaaagctcc     1740
acatcaataa acatgacact ctgaagtgaa agtagccacg agaattgtgc tacttatact     1800
ggttcataat ctggaggcaa ggttcgactg cagccgcccc gtcagcctgt gctaggcatg     1860
gtgtcttcac aggaggcaaa tccagagcct ggctgtgggg aaagtgacca ctctgccctg     1920
accccgatca gttaaggagc tgtgcaataa ccttcctagt acctgagtga gtgtgtaact     1980
tattgggttg gcgaagcctg gtaaagctgt tggaatgagt atgtgattct ttttaagtat     2040
gaaaataaag atatatgtac agacttgtat ttttctctg gtggcattcc tttaggaatg      2100
ctgtgtgtct gtccggcacc ccggtaggcc tgattgggtt tctagtcctc cttaaccact     2160
tatctcccat atgagagtgt gaaaatagg aacacgtgct ctacctccat ttagggattt      2220
gcttgggata cagaagaggc catgtgtctc agagctgtta agggcttatt ttttaaaac      2280 attggagtca tagcatgtgt gtaaacttta aatatgcaaa taataagta tctatgtcta      2340 aaaaaa                                                                2346

<210> SEQ ID NO 13
<211> LENGTH: 3008
<212> TYPE: DNA
<213> ORGANISM: Homo sapiens

<400> SEQUENCE: 13
taattatggg tctgtaacca ccctggactg ggtgctcctc actgacggac ttgtctgaac        60
```

```
ctctctttgt ctccagcgcc cagcactggg cctggcaaaa cctgagacgc ccggtacatg    120
ttggccaaat gaatgaacca gattcagacc ggcaggggcg ctgtggttta ggagggcct     180 ggggtttctc ccaggaggtt tttgggcttg cgctggaggg ctctggactc ccgtttgcgc    240
cagtggcctg catcctggtc ctgtcttcct catgtttgaa tttctttgct ttcctagtct    300
ggggagcagg gaggagccct gtgccctgtc ccaggatcca tgggtaggaa caccatggac    360
agggagagca aacgggcca tctgtcacca ggggcttagg gaaggccgag ccagcctggg     420
tcaaagaagt caaaggggct gcctggagga ggcagcctgt cagctggtgc atcagaggct    480
gtggccaggc cagctgggct cggggagcgc cagcctgaga ggagcgcgtg agcgtcgcgg    540
gagcctcggg caccatgagc gacgtggcta ttgtgaagga gggttggctg cacaaacgag    600
gggagtacat caagacctgg cggccacgct acttcctcct caagaatgat ggcaccttca    660
ttggctacaa ggagcggccg caggatgtgg accaacgtga ggctcccctc aacaacttct    720
ctgtggcgca gtgccagctg atgaagacgg agcggccccg gcccaacacc ttcatcatcc    780
gctgcctgca gtggaccact gtcatcgaac gcaccttcca tgtggagact cctgaggagc    840
gggaggagtg gacaaccgcc atccagactg tggctgacgg cctcaagaag caggaggagg    900
aggagatgga cttccggtcg ggctcaccca gtgacaactc aggggctgaa gagatggagg    960
tgtccctggc caagcccaag caccgcgtga ccatgaacga gtttgagtac ctgaagctgc   1020
tgggcaaggg cactttcggc aaggtgatcc tggtgaagga aaggccaca ggccgctact    1080 acgccatgaa gatcctcaag aaggaagtca tcgtggccaa ggacgaggtg gcccacacac   1140
tcaccgagaa ccgcgtcctg cagaactcca ggcacccctt cctcacagcc ctgaagtact   1200 cttttccagac ccacgaccgc ctctgctttg tcatggagta cgccaacggg ggcgagctgt   1260
tcttccacct gtcccgggag cgtgtgttct ccgaggaccg ggcccgcttc tatggcgctg   1320
agattgtgtc agccctggac tacctgcact cggagaagaa cgtggtgtac cgggacctca   1380
agctggagaa cctcatgctg acaaggacg ggcacattaa gatcacagac ttcgggctgt   1440
gcaaggaggg gatcaaggac ggtgccacca tgaagacctt tgcggcaca cctgagtacc    1500 tggcccccga ggtgctggag acaatgact acggccgtgc agtggactgg tgggggctgg    1560
gcgtggtcat gtacgagatg atgtgcggtc gcctgcccct ctacaaccag gaccatgaga    1620 agcttttga gctcatcctc atggaggaga tccgcttccc gcgcacgctt ggtcccgagg    1680
ccaagtcctt gctttcaggg ctgctcaaga aggaccccaa gcagaggctt ggcggggct    1740 ccgaggacgc caaggagatc atgcagcatc gcttctttgc cggtatcgtg tggcagcacg    1800
tgtacgagaa gaagctcagc ccaccccttca agccccaggt cacgtcggag actgacacca    1860
ggtattttga tgaggagttc acggcccaga tgatcaccat cacaccacct gaccaagatg    1920
acagcatgga gtgtgtggac agcgagcgca ggccccactt cccccagttc tcctactcgg    1980
ccagcggcac ggcctgaggc ggcggtggac tgcgctggac gatagcttgg agggatggag    2040
aggcggcctc gtgccatgat ctgtatttaa tggttttat ttctcgggtg catttgagag     2100
aagccacgct gtcctctcga gcccagatgg aaagacgttt ttgtgctgtg ggcagcaccc    2160 tccccccgcag cggggtaggg aagaaaaacta tcctgcgggt tttaatttat ttcatccagt   2220
ttgttctccg ggtgtggcct cagccctcag aacaatccga ttcacgtagg gaatgttaa    2280 ggacttctgc agctatgcgc aatgtggcat tgggggccg ggcaggtcct gcccatgtgt    2340
cccctcactc tgtcagccag ccgccctggg ctgtctgtca ccagctatct gtcatctctc    2400
```

| | |
|---|---:|
| tggggccctg ggcctcagtt caacctggtg gcaccagatg caacctcact atggtatgct | 2460 |
| ggccagcacc ctctcctggg ggtggcaggc acacagcagc cccccagcac taaggccgtg | 2520 |
| tctctgagga cgtcatcgga ggctgggccc ctgggatggg accagggatg gggatgggc | 2580 |
| cagggtttac ccagtgggac agaggagcaa ggtttaaatt tgttattgtg tattatgttg | 2640 |
| ttcaaatgca ttttgggggt ttttaatctt tgtgacagga aagccctccc ccttcccctt | 2700 |
| ctgtgtcaca gttcttggtg actgtcccac cgggagcctc cccctcagat gatctctcca | 2760 |
| cggtagcact tgacctttc gacgcttaac cttccgctg tcgccccagg ccctccctga | 2820 |
| ctccctgtgg gggtggccat ccctgggccc ctccacgcct cctggccaga cgctgccgct | 2880 |
| gccgctgcac cacggcgttt tttacaaca ttcaacttta gtatttttac tattataata | 2940 |
| taatatggaa ccttccctcc aaattcttca ataaagttg cttttcaaaa aaaaaaaaa | 3000 |
| aaaaaaaa | 3008 |

<210> SEQ ID NO 14
<211> LENGTH: 1872
<212> TYPE: DNA
<213> ORGANISM: Homo sapiens

<400> SEQUENCE: 14

| | |
|---|---:|
| ttaattacaa aaactaatga ctaagagaga ggtggctaga gctgaggccc ctgagtcagg | 60 |
| ctgtgggtgg gatcatctcc agtacaggaa gtgagacttt catttcctcc tttccaagag | 120 |
| agggctgagg gagcagggtt gagcaactgg tgcagacagc ctagctggac tttgggtgag | 180 |
| gcggttcagc catgaggctg gctgtgcttt tctcgggggc cctgctgggg ctactggcag | 240 |
| cccaggggac agggaatgac tgtcctcaca aaaaatcagc tactttgctg ccatccttca | 300 |
| cggtgacacc cacggttaca gagagcactg gaacaaccag ccacaggact accaagagcc | 360 |
| acaaaaccac cactcacagg acaaccacca caggcaccac cagccacgga cccacgactg | 420 |
| ccactcacaa ccccaccacc accagccatg gaaacgtcac agttcatcca caagcaata | 480 |
| gcactgccac cagccaggga ccctcaactg ccactcacag tcctgccacc actagtcatg | 540 |
| gaaatgccac ggttcatcca acaagcaaca gcactgccac cagcccagga ttcaccagtt | 600 |
| ctgcccaccc agaaccacct ccaccctctc cgagtcctag cccaacctcc aaggagacca | 660 |
| ttggagacta cacgtggacc aatggttccc agccctgtgt ccacctccaa gcccagattc | 720 |
| agattcgagt catgtacaca acccagggtg gaggagaggc ctggggcatc tctgtactga | 780 |
| accccaacaa aaccaaggtc cagggaagct gtgagggtgc ccatccccac ctgcttctct | 840 |
| cattccccta tggacacctc agctttggat tcatgcagga cctccagcag aaggttgtct | 900 |
| acctgagcta catggcggtg gagtacaatg tgtccttccc ccacgcagca cagtggacat | 960 |
| tctcggctca gaatgcatcc cttcgagatc tccaagcacc cctggggcag agcttcagtt | 1020 |
| gcagcaactc gagcatcatt cttttcaccag ctgtccacct cgacctgctc tccctgaggc | 1080 |
| tccaggctgc tcagctgccc cacacagggg tctttgggca aagtttctcc tgccccagtg | 1140 |
| accggtccat cttgctgcct ctcatcatcg gcctgatcct tcttggcctc ctcgccctgg | 1200 |
| tgcttattgc tttctgcatc atccggagac gcccatccgc ctaccaggcc ctctgagcat | 1260 |
| ttgcttcaaa cccagggca ctgaggggt tgggtgtgg tgggggta cccttatttc | 1320 |
| ctcgacacgc aactggctca agacaatgt tattttcctt cccttcttg aagaacaaaa | 1380 |
| agaaagccgg gcatgacggc tcatgcctgt aatcccagca ctttgggagg ctgaggcagg | 1440 |
| tggatcactg gaggtcagga gtttgagacc agcctggcca acatggtgaa accctgtctc | 1500 |

| | |
|---|---:|
| tactaaaaat acaattagcc aggtgtggcg gcgtaatccc agctggcctg taatcccagc | 1560 |
| tacttgggag gctgaggcag aactgcttga acccaggagg tggaggttgc agtgagccgt | 1620 |
| catcgcgcca ctaagccaag atcgcgccac tgcactccag cctgggcgac agagccagac | 1680 |
| tgtctcaaat aaataaatat gagataatgc agtcgggaga agggagggag agaattttat | 1740 |
| taaatgtgac gaactgcccc ccccccccccc ccagcaggag agcagcaaaa tttatgcaaa | 1800 |
| tctttgacgg ggttttcctt gtcctgccag gattaaaagc catgagtttc ttgtcaaaaa | 1860 |
| aaaaaaaaaa aa | 1872 |

```
<210> SEQ ID NO 15
<211> LENGTH: 3885
<212> TYPE: DNA
<213> ORGANISM: Homo sapiens

<400> SEQUENCE: 15
```

| | |
|---|---:|
| gcaggccggg gcggggctgg gaagtagtcg ggcggggttg tgagacgccg cgctcagctt | 60 |
| ccatcgctgg gcggtcaaca agtgcgggcc tggctcagcg cggggggggcg cggagaccgc | 120 |
| gaggcgaccg ggagcggctg ggttcccggc tgcgcgccct tcggccaggc cgggagccgc | 180 |
| gccagtcgga gccccccggcc cagcgtggtc cgcctccctc tgggcgtcca cctgcccgga | 240 |
| gtactgccag cgggcatgac cgaccccacca ggggcgccgc cgccggcgct cgcaggccgc | 300 |
| ggatgaagaa gaaaacccgg cgccgctcga cccggagcga ggagttgacc cggagcgagg | 360 |
| agttgaccct gagtgaggaa gcgacctgga gtgaagaggc gacccagagt gaggaggcga | 420 |
| cccagggcga agagatgaat cggagccagg aggtgacccg ggacgaggag tcgacccgga | 480 |
| gcgaggaggt gaccagggag gaaatggcgg cagctgggct caccgtgact gtcacccaca | 540 |
| gcaatgagaa gcacgacctt catgttacct cccagcaggg cagcagtgaa ccagttgtcc | 600 |
| aagacctggc ccaggttgtt gaagaggtca taggggttcc acagtctttt cagaaactca | 660 |
| tatttaaggg aaaatctctg aaggaaatgg aaacaccgtt gtcagcactt ggaatacaag | 720 |
| atggttgccg ggtcatgtta attgggaaaa agaacagtcc acaggaagag gttgaactaa | 780 |
| agaagttgaa acatttggag aagtctgtgg agaagatagc tgaccagctg aagagttga | 840 |
| ataaagagct tactggaatc cagcagggtt ttctgcccaa ggatttgcaa gctgaagctc | 900 |
| tctgcaaaact tgataggaga gtaaaagcca caatagagca gtttatgaag atcttggagg | 960 |
| agattgacac actgatcctg ccagaaaatt tcaaagacag tagattgaaa aggaaaggct | 1020 |
| tggtaaaaaa ggttcaggca ttcctagccg agtgtgacac agtggagcag aacatctgcc | 1080 |
| aggagactga gcggctgcag tctacaaact ttgccctggc cgagtgaggt gtagcagaaa | 1140 |
| aaggctgtgc tgccctgaag aatggcgcca ccagctctgc cgtctctgga gcggaattta | 1200 |
| cctgatttct tcaggctgc tgggggcaac tggccatttg ccaattttcc tactctcaca | 1260 |
| ctggttctca atgaaaaata gtgtctttgt gattttgagt aaagctccta tctgttttct | 1320 |
| ccttctgtct ctgtggttgt actgtccagc aatccacctt ttctggagag ggccacctct | 1380 |
| gcccaaattt tcccagctgt ttggacctct gggtgctttc tttgggctgg tgagagctct | 1440 |
| aatttgcctt gggccagttt caggtttata ggccccctca gtcttcagat acatgagggc | 1500 |
| ttctttgctc ttgtgatcgt gtagtcccat agctgtaaaa ccagaatcac caggaggttg | 1560 |
| cacctagtca ggaatattgg gaatggccta gaacaaggtg tttggcacat aagtagacca | 1620 |
| cttatccctc attgtgacct aattccagag catctggctg ggttgttggg ttctagactt | 1680 |

-continued

```
tgtcctcacc tcccagtgac cctgactagc cacaggccat gagataccag ggggccgttc    1740
cttggatgga gcctgtggtt gatgcaaggc ttccttgtcc ccaagcaagt cttcagaagg    1800
ttagaaccca gtgttgactg agtctgtgct tgaaaccagg ccagagccat ggattaggaa    1860
gggcaaagag aaggcaccag aatgagtaaa gcaggcaggt ggtgaagcca accataaact    1920
tctcaggagt gacatgtgct tccttcaaag gcattttgt taaccatatc cttctgagtt    1980
ctatgtttcc ttcacagctg ttctatccat tttgtggact gtcccccacc cccacccat    2040
cattgttttt aaaaaattaa ggcctggcgc agcagctcat gcctataatc ccagcacttt    2100
gggaggctga ggcgggcgga tcacttgagg ccaggagttt gagaccagcc caggcaacat    2160
agcaaaaccc cattctgctt taaaaaaaaa aaaaaaaaaa attagcttgg cgtagtggca    2220
tgtgcctata atcccagcta ctggggaggc tgaggcacaa gaatcatttg aacctgggag    2280
gtagaggttg ctgtgagccg agattacgcc cctgcactcc agcctgggtc acagagtgag    2340
actccatctc agaaaaaaaa aaaattgagt caggtgcagt agctccttcc tgtagtccca    2400
gctacttggg aggctgaggc tagaggatca cttgagccca ggagtttgag tctagtctgg    2460
gcaacatagc aagaccccat ctctaaaatt taagtaagta aaagtagata aataaaaga     2520
aaaaaaaact gtttatgtgc tcatcataaa gtagaagagt ggtttgcttt ttttttttt    2580
tttggattaa tgaggaaatc attctgtggc tctagtcata atttatgctt aataacattg    2640
atagtagccc tttgcgctat aactctacct aaagactcac atcatttggc agagagagag    2700
tcgttgaagt cccaggaatt caggactggg caggttaaga cctcagacaa ggtagtagag    2760
gtagacttgt ggacaaggct cgggtcccag cccaccgcac cccaacttta atcagagtgg    2820
ttcactattg atctattttt gtgtgatagc tgtgtggcgt gggccacaac atttaatgag    2880
aagttactgt gcaccaaact gccgaacacc attctaaact attcatatat attagtcatt    2940
taattcttac ataacttgag aggtagacag atatccttat tttagagatg aggaaaccaa    3000
gagaacttag gtcattagcg caaggttgta gagtaagcgg caaagccaag acacaaagct    3060
gggtggtttg gtttcagagc cagtgctttt cccctctact gtactgcctc tcaaccaaca    3120
cagggttgca caggcccatt ctctgatttt ttcctcttg tcctctgcct ctccctctag    3180
ctcccacttc ctctctgctc tagttcattt tctttagagc agcccgagtg atcatgaagt    3240
gcaaatcttg ccatgtcagt cccctgctta gaaccctcca atggctcact ttctctttag    3300
gcaaaagtct ttaccccatg ccttctccca tctcatctca acccctcat tgttggctg    3360
tctgctgtca gccactcttc tttcaggtcc tcagatgcac tgcaccctct cctgcctggg    3420
ggtctttgct cctgctacta cctctgcttg aacagctcct caccttcctt cctccaaccc    3480
tacccttgta taggtgactt tgttcatcc ttcagaattc aactcacatg tctccttgcat    3540
ggagaaccct cacctactgt gttgagaccc tgtccagccc ccaggtggga tcctctctcg    3600
acttcccata catttctttc acagcattta catagtccat gatagtttac ttgtgggatt    3660
atttggttaa tctttgcctt taacaccagg gttccttggg tgaaggagct tctttatctt    3720
ggtaacagca ttatttcaag cataacttgt aatatagtta tattcacatat ataacatata    3780
tatatataac ataacatata taacatatat aacaagcata acttgttata tagtcttgta    3840
tatagtaaga cctcaataaa tatttggaga acaaaaaaaa aaaaa                    3885
```

<210> SEQ ID NO 16
<211> LENGTH: 1050
<212> TYPE: DNA
<213> ORGANISM: Homo sapiens

<400> SEQUENCE: 16

```
ctctgagccc tgctcggttt aggcctgtct gcggaatccg caccaaccag caccatgccc      60
atgatactgg ggtactggga catccgcggg ctggcccacg ccatccgcct gctcctggaa     120
tacacagact caagctatga ggaaaagaag tacacgatgg gggacgctcc tgattatgac     180
agaagccagt ggctgaatga aaaattcaag ctgggcctgg actttcccaa tctgccctac     240
ttgattgatg gggctcacaa gatcacccag agcaacgcca tcttgtgcta cattgcccgc     300
aagcacaacc tgtgtgggga gacagaagag gagaagattc gtgtggacat tttggagaac     360
cagaccatgg acaaccatat gcagctgggc atgatctgct acaatccaga atttgagaaa     420
ctgaagccaa agtacttgga ggaactccct gaaaagctaa agctctactc agagtttctg     480
gggaagcggc catggtttgc aggaaacaag ggcttggaga gatctctgc ctacatgaag      540
tccagccgct cctcccaag acctgtgttc tcaaagatgg ctgtctgggg caacaagtag      600
ggccttgaag gccaggaggt gggagtgagg agcccatact cagcctgctg cccaggctgt     660
gcagcgcagc tggactctgc atcccagcac ctgcctcctc gttcctttct cctgtttatt     720
cccatctta ctcccaagac ttcattgtcc ctcttcactc cccctaaacc cctgtcccat      780
gcaggccctt tgaagcctca gctacccact atccttcgtg aacatcccct cccatcatta     840
cccttccctg cactaaagcc agcctgacct tccttcctgt tagtggttgt gtctgcttta     900
aagggcctgc ctggcccctc gcctgtggag ctcagcccg agctgtcccc gtgttgcatg      960
aaggagcagc attgactggt ttacaggccc tgctcctgca gcatggtccc tgccttaggc    1020
ctacctgatg gaagtaaagc ctcaaccaca                                     1050
```

<210> SEQ ID NO 17
<211> LENGTH: 586
<212> TYPE: DNA
<213> ORGANISM: Homo sapiens

<400> SEQUENCE: 17

```
aaacactctg tgtggctcct cggctttgac agagtgcaag acgatgactt gcaaaatgtc      60
gcagctggaa cgcaacatag agaccatcat caacaccttc caccaatact ctgtgaagct     120
ggggcaccca gacaccctga ccaggggga attcaaagag ctggtgcgaa agatctgca      180
aaattttctc aagaaggaga ataagaatga aaaggtcata gaacacatca tggaggacct     240
ggacacaaat gcagacaagc agctgagctt cgaggagttc atcatgctga tggcgaggct     300
aacctgggcc tcccacgaga gatgcacga gggtgacgag ggccctggcc accaccataa     360
gccaggcctc ggggagggca ccccctaaga ccacagtggc caagatcaca gtggccacgg     420
ccacggccac agtcatggtg ccacggcca cagccactaa tcaggaggcc aggccaccct     480
gcctctaccc aaccagggcc ccggggcctg ttatgtcaaa ctgtcttggc tgtggggcta     540
ggggctgggg ccaaataaag tctcttcctc caagtcaaaa aaaaaa                    586
```

<210> SEQ ID NO 18
<211> LENGTH: 1793
<212> TYPE: DNA
<213> ORGANISM: Homo sapiens

<400> SEQUENCE: 18

```
cgcgtccgcc ccgcgagcac agagcctcgc ctttgccgat ccgccgcccg tccacacccg      60
ccgccagctc accatggatg atgatatcgc cgcgctcgtc gtcgacaacg gctccggcat     120
```

|  |  |  |
|---|---|---|
| gtgcaaggcc ggcttcgcgg gcgacgatgc cccccgggcc gtcttcccct ccatcgtggg | 180 | |
| gcgccccagg caccagggcg tgatggtggg catgggtcag aaggattcct atgtgggcga | 240 | |
| cgaggcccag agcaagagag gcatcctcac cctgaagtac cccatcgagc acggcatcgt | 300 | |
| caccaactgg gacgacatgg agaaaatctg gcaccacacc ttctacaatg agctgcgtgt | 360 | |
| ggctcccgag gagcaccccg tgctgctgac cgaggccccc ctgaacccca aggccaaccg | 420 | |
| cgagaagatg acccagatca tgtttgagac cttcaacacc ccagccatgt acgttgctat | 480 | |
| ccaggctgtg ctatccctgt acgcctctgg ccgtaccact ggcatcgtga tggactccgg | 540 | |
| tgacggggtc acccacactg tgcccatcta cgaggggtat gccctccccc atgccatcct | 600 | |
| gcgtctggac ctggctggcc gggacctgac tgactacctc atgaagatcc tcaccgagcg | 660 | |
| cggctacagc ttcaccacca cggccgagcg ggaaatcgtg cgtgacatta aggagaagct | 720 | |
| gtgctacgtc gccctggact cgagcaaga gatggccacg gctgcttcca gctcctccct | 780 | |
| ggagaagagc tacgagctgc ctgacggcca ggtcatcacc attggcaatg agcggttccg | 840 | |
| ctgccctgag gcactcttcc agccttcctt cctgggcatg gagtcctgtg gcatccacga | 900 | |
| aactaccttc aactccatca tgaagtgtga cgtggacatc cgcaaagacc tgtacgccaa | 960 | |
| cacagtgctg tctggcggca ccaccatgta ccctggcatt gccgacagga tgcagaagga | 1020 | |
| gatcactgcc ctggcaccca gcacaatgaa gatcaagatc attgctcctc ctgagcgcaa | 1080 | |
| gtactccgtg tggatcggcg gctccatcct ggcctcgctg tccaccttcc agcagatgtg | 1140 | |
| gatcagcaag caggagtatg acgagtccgg cccctccatc gtccaccgca atgcttcta | 1200 | |
| ggcggactat gacttagttg cgttacaccc tttcttgaca aaacctaact tgcgcagaaa | 1260 | |
| acaagatgag attggcatgg ctttatttgt tttttttgtt ttgttttggt ttttttttt | 1320 | |
| tttttggctt gactcaggat ttaaaaactg gaacggtgaa ggtgacagca gtcggttgga | 1380 | |
| gcgagcatcc cccaaagttc acaatgtggc cgaggacttt gattgcacat tgttgttttt | 1440 | |
| ttaatagtca ttccaaatat gagatgcatt gttacaggaa gtcccttgcc atcctaaaag | 1500 | |
| ccacccact tctctctaag gagaatggcc cagtcctctc ccaagtccac acaggggagg | 1560 | |
| tgatagcatt gctttcgtgt aaattatgta atgcaaaatt ttttaatct tcgccttaat | 1620 | |
| acttttttat tttgttttat tttgaatgat gagccttcgt gccccccctt ccccttttt | 1680 | |
| gtcccccaac ttgagatgta tgaaggcttt tggtctccct gggagtgggt ggaggcagcc | 1740 | |
| agggcttacc tgtacactga cttgagacca gttgaataaa agtgcacacc tta | 1793 | |

<210> SEQ ID NO 19
<211> LENGTH: 1310
<212> TYPE: DNA
<213> ORGANISM: Homo sapiens

<400> SEQUENCE: 19

|  |  |  |
|---|---|---|
| aaattgagcc cgcagcctcc cgcttcgctc tctgctcctc ctgttcgaca gtcagccgca | 60 | |
| tcttcttttg cgtcgccagc cgagccacat cgctcagaca ccatggggaa ggtgaaggtc | 120 | |
| ggagtcaacg gatttggtcg tattgggcgc ctggtcacca gggctgcttt taactctggt | 180 | |
| aaagtggata ttgttgccat caatgacccc ttcattgacc tcaactacat ggtttacatg | 240 | |
| ttccaatatg attccaccca tggcaaattc catggcaccg tcaaggctga gaacgggaag | 300 | |
| cttgtcatca atggaaatcc catcaccatc ttccaggagc gagatccctc caaaatcaag | 360 | |
| tggggcgatg ctggcgctga gtacgtcgtg gagtccactg gcgtcttcac caccatggag | 420 | |
| aaggctgggg ctcatttgca gggggagcc aaaagggtca tcatctctgc ccctctgct | 480 | |

```
gatgccccca tgttcgtcat gggtgtgaac catgagaagt atgacaacag cctcaagatc    540
atcagcaatg cctcctgcac caccaactgc ttagcacccc tggccaaggt catccatgac    600
aactttggta tcgtggaagg actcatgacc acagtccatg ccatcactgc cacccagaag    660
actgtggatg gcccctccgg gaaactgtgg cgtgatggcc gcgggctct ccagaacatc     720 atccctgcct ctactggcgc tgccaaggct gtgggcaagg tcatccctga gctgaacggg    780
aagctcactg gcatggcctt ccgtgtcccc actgccaacg tgtcagtggt ggacctgacc    840
tgccgtctag aaaaacctgc caaatatgat gacatcaaga aggtggtgaa gcaggcgtcg    900
gagggccccc tcagggcat cctgggctac actgagcacc aggtggtctc ctctgacttc      960
aacagcgaca cccactcctc cacctttgac gctggggctg gcattgccct caacgaccac   1020
tttgtcaagc tcatttcctg gtatgacaac gaatttggct acagcaacag ggtggtggac   1080
ctcatggccc acatgcctc caaggagtaa gaccctggg ccaccagccc cagcaagagc      1140
acaagaggaa gagagagacc ctcactgctg gggagtccct gccacactca gtcccccacc   1200
acactgaatc tcccctcctc acagttgcca tgtagacccc ttgaagaggg gaggggccta   1260
gggagccgca ccttgtcatg taccatcaat aaagtaccct gtgctcaacc                1310

<210> SEQ ID NO 20
<211> LENGTH: 2245
<212> TYPE: DNA
<213> ORGANISM: Homo sapiens

<400> SEQUENCE: 20
acgcgacccg ccctacgggc acctcccgcg cttttcttag cgccgcagac ggtggccgag      60
cgggggaccg ggaagcatgg cccggggtc ggcggttgcc tgggcggcgc tcgggccgtt      120
gttgtggggc tgcgcgctgg ggctgcaggg cgggatgctg tacccccagg agagcccgtc     180
gcgggagtgc aaggagctgg acggcctctg gagcttccgc gccgacttct ctgacaaccg    240
acgccggggc ttcgaggagc agtggtaccg gcggccgctg tgggagtcag gccccaccgt    300
ggacatgcca gttccctcca gcttcaatga catcagccag gactggcgtc tgcggcattt    360
tgtcggctgg gtgtggtacg aacgggaggt gatcctgccg gagcgatgga cccaggacct    420
gcgcacaaga gtggtgctga ggattggcag tgcccattcc tatgccatcg tgtgggtgaa    480 tgggtcgac acgctagagc atgagggggg ctacctcccc ttcgaggccg acatcagcaa      540
cctggtccag gtggggcccc tgccctcccg gctccgaatc actatcgcca tcaacaacac   600 actcacccc accaccctgc caccagggac catccaatac ctgactgaca cctccaagta    660
tcccaagggt tactttgtcc agaacacata ttttgacttt ttcaactacg ctggactgca    720
gcggtctgta cttctgtaca cgacacccac cacctacatc gatgacatca ccgtcaccac   780
cagcgtggag caagacagtg ggctggtgaa ttaccagatc tctgtcaagg gcagtaacct   840
gttcaagttg gaagtgcgtc ttttggatgc agaaaacaaa gtcgtggcga atgggactgg    900
gacccagggc caacttaagg tgccaggtgt cagcctctgg tggccgtacc tgatgcacga   960
acgccctgcc tatctgtatt cattggaggt gcagctgact gcacagacgt cactggggcc   1020
tgtgtctgac ttctacacac tccctgtggg gatccgcact gtggctgtca ccaagagcca   1080
gttcctcatc aatgggaaac cttctctattt ccacggtgtc aacaagcatg aggatgcgga    1140
catccgaggg aagggcttcg actgccgct gctggtgaag gacttcaacc tgcttcgctg    1200
gcttggtgcc aacgctttcc gtaccagcca ctaccccctat gcagaggaag tgatgcagat    1260
```

```
gtgtgaccgc tatgggattg tggtcatcga tgagtgtccc ggcgtgggcc tggcgctgcc    1320
gcagttcttc aacaacgttt ctctgcatca ccacatgcag gtgatggaag aagtggtgcg    1380
tagggacaag aaccacccg cggtcgtgat gtggtctgtg ccaacgagc ctgcgtccca      1440 cctagaatct gctggctact acttgaagat ggtgatcgct cacaccaaat ccttggaccc    1500
ctcccggcct gtgacctttg tgagcaactc taactatgca gcagacaagg gggctccgta    1560
tgtggatgtg atctgtttga acagctacta ctcttggtat cacgactacg ggcacctgga    1620
gttgattcag ctgcagctgg ccacccagtt tgagaactgg tataagaagt atcagaagcc    1680
cattattcag agcgagtatg gagcagaaac gattgcaggg tttcaccagg atccacctct    1740
gatgttcact gaagagtacc agaaaagtct gctagagcag taccatctgg gtctggatca    1800
aaaacgcaga aaatacgtgg ttggagagct catttggaat tttgccgatt tcatgactga    1860
acagtcaccg acgagagtgc tggggaataa aaaggggatc ttcactcggc agagacaacc    1920
aaaaagtgca gcgttccttt tgcgagagag atactggaag attgccaatg aaaccaggta    1980
tccccactca gtagccaagt cacaatgttt ggaaaacagc ccgtttactt gagcaagact    2040
gataccacct gcgtgtccct cctccccga gtcaggggga cttccacagc agcagaacaa    2100
gtgcctcctg gactgttcac ggcagaccag aacgtttctg gcctgggttt tgtggtcatc    2160
tattctagca gggaacacta aaggtggaaa taaagatttt ctattatgg aaataaagag     2220 ttggcatgaa agtggctact gaaaa                                          2245

<210> SEQ ID NO 21
<211> LENGTH: 1229
<212> TYPE: DNA
<213> ORGANISM: Homo sapiens

<400> SEQUENCE: 21
gtctgacggg cgatggcgca gccaatagac aggagcgcta tccgcggttt ctgattggct      60
actttgttcg cattataaaa ggcacgcgcg ggcgcgaggc ccttctctcg ccaggcgtcc     120
tcgtggaagt gacatcgtct ttaaaccctg cgtggcaatc cctgacgcac cgccgtgatg     180
cccagggaag acagggcgac ctggaagtcc aactacttcc ttaagatcat ccaactattg     240
gatgattatc cgaaatgttt cattgtggga gcagacaatg tgggctccaa gcagatgcag     300
cagatccgca tgtcccttcg cgggaaggct gtggtgctga tgggcaagaa caccatgatg     360
cgcaaggcca tccgagggca cctggaaaac aacccagctc tggagaaact gctgcctcat     420
atccggggga atgtgggctt tgtgttcacc aaggaggacc tcactgagat cagggacatg     480
ttgctggcca ataaggtgcc agctgctgcc cgtgctggtg ccattgcccc atgtgaagtc     540
actgtgccag cccagaacac tggtctcggg cccgagaaga cctccttttt ccaggcttta     600
ggtatcacca ctaaaatctc caggggcacc attgaaatcc tgagtgatgt gcagctgatc     660
aagactggag acaaagtggg agccagcgaa gccacgctgc tgaacatgct caacatctcc     720
cccttctcct tgggctggt catccagcag tgttcgaca atggcagcat ctacaaccct     780
gaagtgcttg atatcacaga ggaaactctg cattctcgct tcctggaggg tgtccgcaat    840
gttgccagtg tctgtctgca gattggctac ccaactgttg catcagtacc ccattctatc    900
atcaacgggt acaacgagt cctggccttg tctgtggaga cggattacac cttcccactt    960
gctgaaaagg tcaaggcctt cttggctgat ccatctgcct tgtggctgc tgcccctgtg    1020 gctgctgcca ccacagctgc tcctgctgct gctgcagccc cagctaaggt tgaagccaag    1080
gaagagtcgg aggagtcgga cgaggatatg ggatttggtc tctttgacta atcaccaaaa   1140
```

```
agcaaccaac ttagccagtt ttatttgcaa aacaaggaaa taaaggctta cttcttttaaa    1200 aagtaaaaaa aaaaaaaaaa aaaaaaaaa                                      1229

<210> SEQ ID NO 22
<211> LENGTH: 5010
<212> TYPE: DNA
<213> ORGANISM: Homo sapiens

<400> SEQUENCE: 22
ggcggctcgg gacggaggac gcgctagtgt gagtgcgggc ttctagaact acaccgaccc      60
tcgtgtcctc ccttcatcct gcggggctgg ctggagcggc cgctccggtg ctgtccagca     120
gccataggga gccgcacggg gagcgggaaa gcggtcgcgg ccccaggcgg ggcggccggg     180
atggagcggg gccgcgagcc tgtggggaag gggctgtggc ggcgcctcga gcggctgcag     240
gttcttctgt gtggcagttc agaatgatgg atcaagctag atcagcattc tctaacttgt     300
ttggtggaga accattgtca tatcccggt tcagcctggc tcggcaagta gatggcgata      360
acagtcatgt ggagatgaaa cttgctgtag atgaagaaga aaatgctgac aataacacaa     420
aggccaatgt cacaaaacca aaaaggtgta gtggaagtat ctgctatggg actattgctg     480
tgatcgtctt tttcttgatt ggatttatga ttggctactt gggctattgt aaaggggtag     540
aaccaaaaac tgagtgtgag agactggcag gaaccgagtc tccagtgagg gaggagccag     600
gagaggactt ccctgcagca cgtcgcttat attgggatga cctgaagaga aagttgtcgg     660
agaaactgga cagcacagac ttcaccagca ccatcaagct gctgaatgaa aattcatatg     720
tccctcgtga ggctggatct caaaaagatg aaaatcttgc gttgtatgtt gaaaatcaat     780
ttcgtgaatt taaactcagc aaagtctggc gtgatcaaca ttttgttaag attcaggtca     840
aagacagcgc tcaaaactcg gtgatcatag ttgataagaa cggtagactt gtttacctgg     900
tggagaatcc tggggttat gtggcgtata gtaaggctgc aacagttact ggtaaactgg      960
tccatgctaa ttttggtact aaaaaagatt tgaggatttt atacactcct gtgaatggat    1020
ctatagtgat tgtcagagca gggaaaatca ccttttgcaga aaaggttgca aatgctgaaa    1080
gcttaaatgc aattggtgtg ttgatataca tggaccagac taaatttccc attgttaacg    1140
cagaactttc attctttgga catgctcatc tggggacagg tgacccttac acacctggat    1200
tcccttcctt caatcacact cagtttccac catctcggtc atcaggattg cctaatatac    1260
ctgtccagac aatctccaga gctgctgcag aaaagctgtt tgggaatatg aaggagact     1320 gtccctctga ctggaaaaca gactctacat gtaggatggt aacctcagaa agcaagaatg    1380
tgaagctcac tgtgagcaat gtgctgaaag agataaaaat tcttaacatc tttggagtta    1440
ttaaaggctt tgtagaacca gatcactatg ttgtagttgg ggcccagaga gatgcatggg    1500
gccctggagc tgcaaaatcc ggtgtaggca cagctctcct attgaaactt gcccagatgt    1560
tctcagatat ggtcttaaaa gatgggtttc agcccagcag aagcattatc tttgccagtt    1620
ggagtgctgg agactttgga tcggttggtg ccactgaatg gctagaggga tacctttcgt    1680
ccctgcattt aaaggctttc acttatatta atctggataa agcggttctt ggtaccagca    1740
acttcaaggt ttctgccagc ccactgttgt atacgcttat tgagaaaaca atgcaaaatg    1800
tgaagcatcc ggttactggg caatttctat atcaggacac caactgggcc agcaaagttg    1860
agaaactcac tttagacaat gctgcttccc ctttccttgc atattctgga atcccagcag    1920 tttcttctctg ttttttgcgag gacacagatt atccttattt gggtaccacc atggacacct    1980
```

```
ataaggaact gattgagagg attcctgagt tgaacaaagt ggcacgagca gctgcagagg    2040
tcgctggtca gttcgtgatt aaactaaccc atgatgttga attgaacctg gactatgaga    2100
ggtacaacag ccaactgctt tcatttgtga gggatctgaa ccaatacaga gcagacataa    2160
aggaaatggg cctgagttta cagtggctgt attctgctcg tggagacttc ttccgtgcta    2220
cttccagact aacaacagat ttcgggaatg ctgagaaaac agacagattt gtcatgaaga    2280
aactcaatga tcgtgtcatg agagtggagt atcacttcct ctctccctac gtatctccaa    2340
aagagtctcc tttccgacat gtcttctggg gctccggctc tcacacgctg ccagctttac    2400
tggagaactt gaaactgcgt aaacaaaata acggtgcttt taatgaaacg ctgttcagaa    2460
accagttggc tctagctact tggactattc agggagctgc aaatgccctc tctggtgacg    2520
tttgggacat tgacaatgag ttttaaatgt gatacccata gcttccatga aacagcagg    2580 gtagtctggt ttctagactt gtgctgatcg tgctaaattt tcagtagggc tacaaaacct    2640
gatgttaaaa ttcatccca tcatcttggt actactagat gtctttaggc agcagctttt    2700
aatacagggt agataacctg tacttcaagt taaagtgaat aaccacttaa aaaatgtcca    2760
tgatggaata ttcccctatc tctagaattt taagtgcttt gtaatgggaa ctgcctcttt    2820
cctgttgttg ttaatgaaaa tgtcagaaac cagttatgtg aatgatctct ctgaatccta    2880
agggctggtc tctgctgaag gttgtaagtg gttcgcttac tttgagtgat cctccaactt    2940
catttgatgc taaataggag ataccaggtt gaaagacctc tccaaatgag atctaagcct    3000
ttccataagg aatgtagcag gtttcctcat tcctgaaaga aacagttaac tttcagaaga    3060
gatgggcttg ttttcttgcc aatgaggtct gaaatggagg tccttctgct ggataaaatg    3120
aggttcaact gttgattgca ggaataaggc cttaatatgt taacctcagt gtcatttatg    3180
aaaagagggg accagaagcc aaagacttag tatattttct tttcctctgt cccttccccc    3240
ataagcctcc atttagttct ttgttatttt tgtttcttcc aaagcacatt gaaagagaac    3300
cagtttcagg tgtttagttg cagactcagt ttgtcagact ttaaagaata atatgctgcc    3360
aaattttggc caaagtgtta atcttagggg agagctttct gtccttttgg cactgagata    3420
tttattgttt atttatcagt gacagagttc actataaatg gtgttttttt aatagaatat    3480
aattatcgga agcagtgcct tccataatta tgacagttat actgtcggtt tttttaaat    3540 aaaagcagca tctgctaata aaacccaaca gatactggaa gttttgcatt tatggtcaac    3600
acttaagggt tttagaaaac agccgtcagc caaatgtaat tgaataaagt tgaagctaag    3660
atttagagat gaattaaatt taattagggg ttgctaagaa gcgagcactg accagataag    3720
aatgctggtt ttcctaaatg cagtgaattg tgaccaagtt ataaatcaat gtcacttaaa    3780
ggctgtggta gtactcctgc aaaatttat agctcagttt atccaaggtg taactctaat    3840
tcccatttgc aaaatttcca gtacctttgt cacaatccta acacattatc gggagcagtg    3900
tcttccataa tgtataaaga acaaggtagt ttttacctac cacagtgtct gtatcggaga    3960
cagtgatctc catatgttac actaagggtg taagtaatta tcgggaacag tgtttcccat    4020 aatttttcttc atgcaatgac atcttcaaag cttgaagatc gttagtatct aacatgtatc    4080
ccaactccta taattcccta tcttttagtt ttagttgcag aaacattttg tggtcattaa    4140
gcattgggtg ggtaaattca accactgtaa aatgaaatta ctacaaaatt tgaaatttag    4200
cttgggtttt tgttacccttt atggtttctc caggtcctct acttaatgag atagcagcat    4260
acatttataa tgtttgctat tgacaagtca ttttaattta tcacattatt tgcatgttac    4320
ctcctataaa cttagtgcgg acaagtttta atccagaatt gacctttga cttaaagcag    4380
```

-continued

```
agggactttg tatagaaggt ttgggggctg tggggaagga gagtcccctg aaggtctgac      4440
acgtctgcct acccattcgt ggtgatcaat taaatgtagg tatgaataag ttcgaagctc      4500
cgtgagtgaa ccatcatata aacgtgtagt acagctgttt gtcataggc agttggaaac      4560
ggcctcctag ggaaaagttc atagggtctc ttcaggttct tagtgtcact tacctagatt      4620
tacagcctca cttgaatgtg tcactactca cagtctcttt aatcttcagt tttatcttta      4680
atctcctctt ttatcttgga ctgacattta gcgtagctaa gtgaaaaggt catagctgag      4740
attcctggtt cgggtgttac gcacacgtac ttaaatgaaa gcatgtggca tgttcatcgt      4800
ataacacaat atgaatacag ggcatgcatt ttgcagcagt gagtctcttc agaaaaccct      4860
tttctacagt tagggttgag ttacttccta tcaagccagt acgtgctaac aggctcaata      4920
ttcctgaatg aaatatcaga ctagtgacaa gctcctggtc ttgagatgtc ttctcgttaa      4980
ggagtagggc cttttggagg taaaggtata                                       5010
```

<210> SEQ ID NO 23
<211> LENGTH: 1255
<212> TYPE: PRT
<213> ORGANISM: Homo sapiens

<400> SEQUENCE: 23

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255
```

```
His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
            275                 280                 285

Tyr Thr Phe Gly Ala Ser Cys Val Thr Ala Cys Pro Tyr Asn Tyr Leu
            290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
            370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
            450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
            515                 520                 525

Val Asn Cys Ser Gln Phe Leu Arg Gly Gln Glu Cys Val Glu Glu Cys
            530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
            595                 600                 605

Ser Tyr Met Pro Ile Trp Lys Phe Pro Asp Glu Glu Gly Ala Cys Gln
            610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
```

-continued

```
            675                 680                 685
Arg Leu Leu Gln Glu Thr Glu Leu Val Glu Pro Leu Thr Pro Ser Gly
690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
                740                 745                 750

Lys Val Leu Arg Glu Asn Thr Ser Pro Lys Ala Asn Lys Glu Ile Leu
                755                 760                 765

Asp Glu Ala Tyr Val Met Ala Gly Val Gly Ser Pro Tyr Val Ser Arg
770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
                820                 825                 830

Met Ser Tyr Leu Glu Asp Val Arg Leu Val His Arg Asp Leu Ala Ala
                835                 840                 845

Arg Asn Val Leu Val Lys Ser Pro Asn His Val Lys Ile Thr Asp Phe
                850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
                900                 905                 910

Trp Glu Leu Met Thr Phe Gly Ala Lys Pro Tyr Asp Gly Ile Pro Ala
                915                 920                 925

Arg Glu Ile Pro Asp Leu Leu Glu Lys Gly Glu Arg Leu Pro Gln Pro
                930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
                980                 985                 990

Asp Leu Gly Pro Ala Ser Pro Leu Asp Ser Thr Phe Tyr Arg Ser Leu
                995                 1000                1005

Leu Glu Asp Asp Asp Met Gly Asp Leu Val Asp Ala Glu Glu Tyr
                1010                1015                1020

Leu Val Pro Gln Gln Gly Phe Phe Cys Pro Asp Pro Ala Pro Gly
                1025                1030                1035

Ala Gly Gly Met Val His His Arg His Arg Ser Ser Ser Thr Arg
                1040                1045                1050

Ser Gly Gly Gly Asp Leu Thr Leu Gly Leu Glu Pro Ser Glu Glu
                1055                1060                1065

Glu Ala Pro Arg Ser Pro Leu Ala Pro Ser Glu Gly Ala Gly Ser
                1070                1075                1080

Asp Val Phe Asp Gly Asp Leu Gly Met Gly Ala Ala Lys Gly Leu
                1085                1090                1095
```

-continued

```
Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 24
<211> LENGTH: 532
<212> TYPE: PRT
<213> ORGANISM: Homo sapiens

<400> SEQUENCE: 24

Met Glu Leu Asp Leu Ser Pro Pro His Leu Ser Ser Pro Glu Asp
1               5                   10                  15

Leu Cys Pro Ala Pro Gly Thr Pro Gly Thr Pro Arg Pro Pro Asp
                20                  25                  30

Thr Pro Leu Pro Glu Glu Val Lys Arg Ser Gln Pro Leu Leu Ile Pro
            35                  40                  45

Thr Thr Gly Arg Lys Leu Arg Glu Glu Arg Arg Ala Thr Ser Leu
    50                  55                  60

Pro Ser Ile Pro Asn Pro Phe Pro Glu Leu Cys Ser Pro Ser Gln
65                  70                  75                  80

Ser Pro Ile Leu Gly Gly Pro Ser Ser Ala Arg Gly Leu Leu Pro Arg
                85                  90                  95

Asp Ala Ser Arg Pro His Val Val Lys Val Tyr Ser Glu Asp Gly Ala
                100                 105                 110

Cys Arg Ser Val Glu Val Ala Ala Gly Ala Thr Ala Arg His Val Cys
                115                 120                 125

Glu Met Leu Val Gln Arg Ala His Ala Leu Ser Asp Glu Thr Trp Gly
    130                 135                 140

Leu Val Glu Cys His Pro His Leu Ala Leu Glu Arg Gly Leu Glu Asp
145                 150                 155                 160

His Glu Ser Val Val Glu Val Gln Ala Ala Trp Pro Val Gly Gly Asp
                    165                 170                 175

Ser Arg Phe Val Phe Arg Lys Asn Phe Ala Lys Tyr Glu Leu Phe Lys
                180                 185                 190

Ser Ser Pro His Ser Leu Phe Pro Glu Lys Met Val Ser Ser Cys Leu
```

```
                195                 200                 205
Asp Ala His Thr Gly Ile Ser His Glu Asp Leu Ile Gln Asn Phe Leu
    210                 215                 220
Asn Ala Gly Ser Phe Pro Glu Ile Gln Gly Phe Leu Gln Leu Arg Gly
225                 230                 235                 240
Ser Gly Arg Lys Leu Trp Lys Arg Phe Phe Cys Phe Leu Arg Arg Ser
                245                 250                 255
Gly Leu Tyr Tyr Ser Thr Lys Gly Thr Ser Lys Asp Pro Arg His Leu
            260                 265                 270
Gln Tyr Val Ala Asp Val Asn Glu Ser Asn Val Tyr Val Val Thr Gln
        275                 280                 285
Gly Arg Lys Leu Tyr Gly Met Pro Thr Asp Phe Gly Phe Cys Val Lys
    290                 295                 300
Pro Asn Lys Leu Arg Asn Gly His Lys Gly Leu Arg Ile Phe Cys Ser
305                 310                 315                 320
Glu Asp Glu Gln Ser Arg Thr Cys Trp Leu Ala Ala Phe Arg Leu Phe
                325                 330                 335
Lys Tyr Gly Val Gln Leu Tyr Lys Asn Tyr Gln Gln Ala Gln Ser Arg
            340                 345                 350
His Leu His Pro Ser Cys Leu Gly Ser Pro Leu Arg Ser Ala Ser
        355                 360                 365
Asp Asn Thr Leu Val Ala Met Asp Phe Ser Gly His Ala Gly Arg Val
    370                 375                 380
Ile Glu Asn Pro Arg Glu Ala Leu Ser Val Ala Leu Glu Glu Ala Gln
385                 390                 395                 400
Ala Trp Arg Lys Lys Thr Asn His Arg Leu Ser Leu Pro Met Pro Ala
                405                 410                 415
Ser Gly Thr Ser Leu Ser Ala Ala Ile His Arg Thr Gln Leu Trp Phe
            420                 425                 430
His Gly Arg Ile Ser Arg Glu Glu Ser Gln Arg Leu Ile Gly Gln Gln
        435                 440                 445
Gly Leu Val Asp Gly Leu Phe Leu Val Arg Glu Ser Gln Arg Asn Pro
    450                 455                 460
Gln Gly Phe Val Leu Ser Leu Cys His Leu Gln Lys Val Lys His Tyr
465                 470                 475                 480
Leu Ile Leu Pro Ser Glu Glu Gly Arg Leu Tyr Phe Ser Met Asp
                485                 490                 495
Asp Gly Gln Thr Arg Phe Thr Asp Leu Leu Gln Leu Val Glu Phe His
            500                 505                 510
Gln Leu Asn Arg Gly Ile Leu Pro Cys Leu Leu Arg His Cys Cys Thr
        515                 520                 525
Arg Val Ala Leu
    530

<210> SEQ ID NO 25
<211> LENGTH: 379
<212> TYPE: PRT
<213> ORGANISM: Homo sapiens

<400> SEQUENCE: 25

Met Ala Ala Ala Ala Gln Gly Gly Gly Gly Gly Glu Pro Arg Arg
1               5                   10                  15
Thr Glu Gly Val Gly Pro Gly Val Pro Gly Glu Val Glu Met Val Lys
                20                  25                  30
```

```
Gly Gln Pro Phe Asp Val Gly Pro Arg Tyr Thr Gln Leu Gln Tyr Ile
        35                  40                  45

Gly Glu Gly Ala Tyr Gly Met Val Ser Ser Ala Tyr Asp His Val Arg
 50                  55                  60

Lys Thr Arg Val Ala Ile Lys Lys Ile Ser Pro Phe Glu His Gln Thr
 65                  70                  75                  80

Tyr Cys Gln Arg Thr Leu Arg Glu Ile Gln Ile Leu Leu Arg Phe Arg
                 85                  90                  95

His Glu Asn Val Ile Gly Ile Arg Asp Ile Leu Arg Ala Ser Thr Leu
            100                 105                 110

Glu Ala Met Arg Asp Val Tyr Ile Val Gln Asp Leu Met Glu Thr Asp
            115                 120                 125

Leu Tyr Lys Leu Leu Lys Ser Gln Gln Leu Ser Asn Asp His Ile Cys
130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ile Asn Thr
                165                 170                 175

Thr Cys Asp Leu Lys Ile Cys Asp Phe Gly Leu Ala Arg Ile Ala Asp
            180                 185                 190

Pro Glu His Asp His Thr Gly Phe Leu Thr Glu Tyr Val Ala Thr Arg
            195                 200                 205

Trp Tyr Arg Ala Pro Glu Ile Met Leu Asn Ser Lys Gly Tyr Thr Lys
            210                 215                 220

Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
                245                 250                 255

Ile Leu Gly Ile Leu Gly Ser Pro Ser Gln Glu Asp Leu Asn Cys Ile
            260                 265                 270

Ile Asn Met Lys Ala Arg Asn Tyr Leu Gln Ser Leu Pro Ser Lys Thr
            275                 280                 285

Lys Val Ala Trp Ala Lys Leu Phe Pro Lys Ser Asp Ser Lys Ala Leu
            290                 295                 300

Asp Leu Leu Asp Arg Met Leu Thr Phe Asn Pro Asn Lys Arg Ile Thr
305                 310                 315                 320

Val Glu Glu Ala Leu Ala His Pro Tyr Leu Glu Gln Tyr Tyr Asp Pro
                325                 330                 335

Thr Asp Glu Pro Val Ala Glu Glu Pro Phe Thr Phe Ala Met Glu Leu
            340                 345                 350

Asp Asp Leu Pro Lys Glu Arg Leu Lys Glu Leu Ile Phe Gln Glu Thr
            355                 360                 365

Ala Arg Phe Gln Pro Gly Val Leu Glu Ala Pro
            370                 375

<210> SEQ ID NO 26
<211> LENGTH: 384
<212> TYPE: PRT
<213> ORGANISM: Homo sapiens

<400> SEQUENCE: 26

Met Ser Arg Ser Lys Arg Asp Asn Asn Phe Tyr Ser Val Glu Ile Gly
1               5                  10                  15

Asp Ser Thr Phe Thr Val Leu Lys Arg Tyr Gln Asn Leu Lys Pro Ile
            20                  25                  30
```

-continued

Gly Ser Gly Ala Gln Gly Ile Val Cys Ala Ala Tyr Asp Ala Ile Leu
            35                  40                  45

Glu Arg Asn Val Ala Ile Lys Lys Leu Ser Arg Pro Phe Gln Asn Gln
 50                  55                  60

Thr His Ala Lys Arg Ala Tyr Arg Glu Leu Val Leu Met Lys Cys Val
 65                  70                  75                  80

Asn His Lys Asn Ile Ile Gly Leu Leu Asn Val Phe Thr Pro Gln Lys
                85                  90                  95

Ser Leu Glu Glu Phe Gln Asp Val Tyr Ile Val Met Glu Leu Met Asp
            100                 105                 110

Ala Asn Leu Cys Gln Val Ile Gln Met Glu Leu Asp His Glu Arg Met
            115                 120                 125

Ser Tyr Leu Leu Tyr Gln Met Leu Cys Gly Ile Lys His Leu His Ser
            130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Gly Thr Ser Phe Met Met Thr Pro Tyr Val Val Thr Arg Tyr Tyr Arg
            180                 185                 190

Ala Pro Glu Val Ile Leu Gly Met Gly Tyr Lys Glu Asn Val Asp Leu
            195                 200                 205

Trp Ser Val Gly Cys Ile Met Gly Glu Met Val Cys His Lys Ile Leu
210                 215                 220

Phe Pro Gly Arg Asp Tyr Ile Asp Gln Trp Asn Lys Val Ile Glu Gln
225                 230                 235                 240

Leu Gly Thr Pro Cys Pro Glu Phe Met Lys Lys Leu Gln Pro Thr Val
            245                 250                 255

Arg Thr Tyr Val Glu Asn Arg Pro Lys Tyr Ala Gly Tyr Ser Phe Glu
            260                 265                 270

Lys Leu Phe Pro Asp Val Leu Phe Pro Ala Asp Ser Glu His Asn Lys
            275                 280                 285

Leu Lys Ala Ser Gln Ala Arg Asp Leu Leu Ser Lys Met Leu Val Ile
            290                 295                 300

Asp Ala Ser Lys Arg Ile Ser Val Asp Glu Ala Leu Gln His Pro Tyr
305                 310                 315                 320

Ile Asn Val Trp Tyr Asp Pro Ser Glu Ala Glu Ala Pro Pro Pro Lys
                325                 330                 335

Ile Pro Asp Lys Gln Leu Asp Glu Arg Glu His Thr Ile Glu Glu Trp
            340                 345                 350

Lys Glu Leu Ile Tyr Lys Glu Val Met Asp Leu Glu Glu Arg Thr Lys
            355                 360                 365

Asn Gly Val Ile Arg Gly Gln Pro Ser Pro Leu Ala Gln Val Gln Gln
            370                 375                 380

<210> SEQ ID NO 27
<211> LENGTH: 239
<212> TYPE: PRT
<213> ORGANISM: Homo sapiens

<400> SEQUENCE: 27

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala

-continued

```
                        20                  25                  30
Gly Asp Val Gly Ala Ala Pro Pro Gly Ala Ala Pro Pro Gly Ile
             35                  40                  45
Phe Ser Ser Gln Pro Gly His Thr Pro His Pro Ala Ala Ser Arg Asp
 50                  55                  60
Pro Val Ala Arg Thr Ser Pro Leu Gln Thr Pro Ala Ala Pro Gly Ala
 65                  70                  75                  80
Ala Ala Gly Pro Ala Leu Ser Pro Val Pro Pro Val Val His Leu Thr
                 85                  90                  95
Leu Arg Gln Ala Gly Asp Asp Phe Ser Arg Arg Tyr Arg Arg Asp Phe
            100                 105                 110
Ala Glu Met Ser Ser Gln Leu His Leu Thr Pro Phe Thr Ala Arg Gly
            115                 120                 125
Arg Phe Ala Thr Val Val Glu Glu Leu Phe Arg Asp Gly Val Asn Trp
            130                 135                 140
Gly Arg Ile Val Ala Phe Phe Glu Phe Gly Gly Val Met Cys Val Glu
145                 150                 155                 160
Ser Val Asn Arg Glu Met Ser Pro Leu Val Asp Asn Ile Ala Leu Trp
                165                 170                 175
Met Thr Glu Tyr Leu Asn Arg His Leu His Thr Trp Ile Gln Asp Asn
                180                 185                 190
Gly Gly Trp Asp Ala Phe Val Glu Leu Tyr Gly Pro Ser Met Arg Pro
            195                 200                 205
Leu Phe Asp Phe Ser Trp Leu Ser Leu Lys Thr Leu Leu Ser Leu Ala
            210                 215                 220
Leu Val Gly Ala Cys Ile Thr Leu Gly Ala Tyr Leu Gly His Lys
225                 230                 235

<210> SEQ ID NO 28
<211> LENGTH: 433
<212> TYPE: PRT
<213> ORGANISM: Homo sapiens

<400> SEQUENCE: 28

Met Ser Gly Arg Pro Arg Thr Thr Ser Phe Ala Glu Ser Cys Lys Pro
 1               5                  10                  15
Val Gln Gln Pro Ser Ala Phe Gly Ser Met Lys Val Ser Arg Asp Lys
                20                  25                  30
Asp Gly Ser Lys Val Thr Thr Val Val Ala Thr Pro Gly Gln Gly Pro
             35                  40                  45
Asp Arg Pro Gln Glu Val Ser Tyr Thr Asp Thr Lys Val Ile Gly Asn
 50                  55                  60
Gly Ser Phe Gly Val Val Tyr Gln Ala Lys Leu Cys Asp Ser Gly Glu
 65                  70                  75                  80
Leu Val Ala Ile Lys Lys Val Leu Gln Asp Lys Arg Phe Lys Asn Arg
                 85                  90                  95
Glu Leu Gln Ile Met Arg Lys Leu Asp His Cys Asn Ile Val Arg Leu
            100                 105                 110
Arg Tyr Phe Phe Tyr Ser Ser Gly Glu Lys Lys Asp Glu Val Tyr Leu
            115                 120                 125
Asn Leu Val Leu Asp Tyr Val Pro Glu Thr Val Tyr Arg Val Ala Arg
            130                 135                 140
His Tyr Ser Arg Ala Lys Gln Thr Leu Pro Val Ile Tyr Val Lys Leu
145                 150                 155                 160
```

```
Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285

Thr Glu Phe Lys Phe Pro Gln Ile Lys Ala His Pro Trp Thr Lys Asp
    290                 295                 300

Ser Ser Gly Thr Gly His Phe Thr Ser Gly Val Arg Val Phe Arg Pro
305                 310                 315                 320

Arg Thr Pro Pro Glu Ala Ile Ala Leu Cys Ser Arg Leu Leu Glu Tyr
                325                 330                 335

Thr Pro Thr Ala Arg Leu Thr Pro Leu Glu Ala Cys Ala His Ser Phe
            340                 345                 350

Phe Asp Glu Leu Arg Asp Pro Asn Val Lys Leu Pro Asn Gly Arg Asp
        355                 360                 365

Thr Pro Ala Leu Phe Asn Phe Thr Thr Gln Glu Leu Ser Ser Asn Pro
    370                 375                 380

Pro Leu Ala Thr Ile Leu Ile Pro Pro His Ala Arg Ile Gln Ala Ala
385                 390                 395                 400

Ala Ser Thr Pro Thr Asn Ala Thr Ala Ala Ser Asp Ala Asn Thr Gly
                405                 410                 415

Asp Arg Gly Gln Thr Asn Asn Ala Ala Ser Ala Ser Ala Ser Asn Ser
            420                 425                 430

Thr

<210> SEQ ID NO 29
<211> LENGTH: 488
<212> TYPE: PRT
<213> ORGANISM: Homo sapiens

<400> SEQUENCE: 29

Met Ala Pro Ala Ala Trp Leu Arg Ser Ala Ala Ala Arg Ala Leu Leu
1               5                   10                  15

Pro Pro Met Leu Leu Leu Leu Leu Gln Pro Pro Leu Leu Leu Ala Arg
            20                  25                  30

Ala Leu Pro Pro Asp Ala His His Leu His Ala Glu Arg Arg Gly Pro
        35                  40                  45

Gln Pro Trp His Ala Ala Leu Pro Ser Ser Pro Ala Pro Ala Pro Ala
    50                  55                  60

Thr Gln Glu Ala Pro Arg Pro Ala Ser Ser Leu Arg Pro Pro Arg Cys
65                  70                  75                  80

Gly Val Pro Asp Pro Ser Asp Gly Leu Ser Ala Arg Asn Arg Gln Lys
                85                  90                  95
```

```
Arg Phe Val Leu Ser Gly Gly Arg Trp Glu Lys Thr Asp Leu Thr Tyr
                100                 105                 110

Arg Ile Leu Arg Phe Pro Trp Gln Leu Val Gln Glu Gln Val Arg Gln
            115                 120                 125

Thr Met Ala Glu Ala Leu Lys Val Trp Ser Asp Val Thr Pro Leu Thr
        130                 135                 140

Phe Thr Glu Val His Glu Gly Arg Ala Asp Ile Met Ile Asp Phe Ala
145                 150                 155                 160

Arg Tyr Trp His Gly Asp Asp Leu Pro Phe Asp Gly Pro Gly Gly Ile
                165                 170                 175

Leu Ala His Ala Phe Phe Pro Lys Thr His Arg Glu Gly Asp Val His
            180                 185                 190

Phe Asp Tyr Asp Glu Thr Trp Thr Ile Gly Asp Asp Gln Gly Thr Asp
        195                 200                 205

Leu Leu Gln Val Ala Ala His Glu Phe Gly His Val Leu Gly Leu Gln
210                 215                 220

His Thr Thr Ala Ala Lys Ala Leu Met Ser Ala Phe Tyr Thr Phe Arg
225                 230                 235                 240

Tyr Pro Leu Ser Leu Ser Pro Asp Asp Cys Arg Gly Val Gln His Leu
                245                 250                 255

Tyr Gly Gln Pro Trp Pro Thr Val Thr Ser Arg Thr Pro Ala Leu Gly
            260                 265                 270

Pro Gln Ala Gly Ile Asp Thr Asn Glu Ile Ala Pro Leu Glu Pro Asp
        275                 280                 285

Ala Pro Pro Asp Ala Cys Glu Ala Ser Phe Asp Ala Val Ser Thr Ile
290                 295                 300

Arg Gly Glu Leu Phe Phe Phe Lys Ala Gly Phe Val Trp Arg Leu Arg
305                 310                 315                 320

Gly Gly Gln Leu Gln Pro Gly Tyr Pro Ala Leu Ala Ser Arg His Trp
                325                 330                 335

Gln Gly Leu Pro Ser Pro Val Asp Ala Ala Phe Glu Asp Ala Gln Gly
            340                 345                 350

His Ile Trp Phe Phe Gln Gly Ala Gln Tyr Trp Val Tyr Asp Gly Glu
        355                 360                 365

Lys Pro Val Leu Gly Pro Ala Pro Leu Thr Glu Leu Gly Leu Val Arg
370                 375                 380

Phe Pro Val His Ala Ala Leu Val Trp Gly Pro Glu Lys Asn Lys Ile
385                 390                 395                 400

Tyr Phe Phe Arg Gly Arg Asp Tyr Trp Arg Phe His Pro Ser Thr Arg
                405                 410                 415

Arg Val Asp Ser Pro Val Pro Arg Arg Ala Thr Asp Trp Arg Gly Val
            420                 425                 430

Pro Ser Glu Ile Asp Ala Ala Phe Gln Asp Ala Asp Gly Tyr Ala Tyr
        435                 440                 445

Phe Leu Arg Gly Arg Leu Tyr Trp Lys Phe Asp Pro Val Lys Val Lys
450                 455                 460

Ala Leu Glu Gly Phe Pro Arg Leu Val Gly Pro Asp Phe Phe Gly Cys
465                 470                 475                 480

Ala Glu Pro Ala Asn Thr Phe Leu
                485

<210> SEQ ID NO 30
<211> LENGTH: 334
<212> TYPE: PRT
```

<213> ORGANISM: Homo sapiens

<400> SEQUENCE: 30

```
Met Asn Leu Ser Leu Val Leu Ala Ala Phe Cys Leu Gly Ile Ala Ser
1               5                   10                  15

Ala Val Pro Lys Phe Asp Gln Asn Leu Asp Thr Lys Trp Tyr Gln Trp
            20                  25                  30

Lys Ala Thr His Arg Arg Leu Tyr Gly Ala Asn Glu Glu Gly Trp Arg
        35                  40                  45

Arg Ala Val Trp Glu Lys Asn Met Lys Met Ile Glu Leu His Asn Gly
    50                  55                  60

Glu Tyr Ser Gln Gly Lys His Gly Phe Thr Met Ala Met Asn Ala Phe
65                  70                  75                  80

Gly Asp Met Thr Asn Glu Glu Phe Arg Gln Met Met Gly Cys Phe Arg
                85                  90                  95

Asn Gln Lys Phe Arg Lys Gly Lys Val Phe Arg Glu Pro Leu Phe Leu
            100                 105                 110

Asp Leu Pro Lys Ser Val Asp Trp Arg Lys Lys Gly Tyr Val Thr Pro
        115                 120                 125

Val Lys Asn Gln Lys Gln Cys Gly Ser Cys Trp Ala Phe Ser Ala Thr
    130                 135                 140

Gly Ala Leu Glu Gly Gln Met Phe Arg Lys Thr Gly Lys Leu Val Ser
145                 150                 155                 160

Leu Ser Glu Gln Asn Leu Val Asp Cys Ser Arg Pro Gln Gly Asn Gln
                165                 170                 175

Gly Cys Asn Gly Gly Phe Met Ala Arg Ala Phe Gln Tyr Val Lys Glu
            180                 185                 190

Asn Gly Gly Leu Asp Ser Glu Glu Ser Tyr Pro Tyr Val Ala Val Asp
        195                 200                 205

Glu Ile Cys Lys Tyr Arg Pro Glu Asn Ser Val Ala Asn Asp Thr Gly
    210                 215                 220

Phe Thr Val Val Ala Pro Gly Lys Glu Lys Ala Leu Met Lys Ala Val
225                 230                 235                 240

Ala Thr Val Gly Pro Ile Ser Val Ala Met Asp Ala Gly His Ser Ser
                245                 250                 255

Phe Gln Phe Tyr Lys Ser Gly Ile Tyr Phe Glu Pro Asp Cys Ser Ser
            260                 265                 270

Lys Asn Leu Asp His Gly Val Leu Val Val Gly Tyr Gly Phe Glu Gly
        275                 280                 285

Ala Asn Ser Asn Asn Ser Lys Tyr Trp Leu Val Lys Asn Ser Trp Gly
    290                 295                 300

Pro Glu Trp Gly Ser Asn Gly Tyr Val Lys Ile Ala Lys Asp Lys Asn
305                 310                 315                 320

Asn His Cys Gly Ile Ala Thr Ala Ala Ser Tyr Pro Asn Val
                325                 330
```

<210> SEQ ID NO 31
<211> LENGTH: 433
<212> TYPE: PRT
<213> ORGANISM: Homo sapiens

<400> SEQUENCE: 31

```
Met Ala Leu Arg Val Thr Arg Asn Ser Lys Ile Asn Ala Glu Asn Lys
1               5                   10                  15

Ala Lys Ile Asn Met Ala Gly Ala Lys Arg Val Pro Thr Ala Pro Ala
```

```
                    20                  25                  30
Ala Thr Ser Lys Pro Gly Leu Arg Pro Arg Thr Ala Leu Gly Asp Ile
            35                  40                  45
Gly Asn Lys Val Ser Glu Gln Leu Gln Ala Lys Met Pro Met Lys Lys
 50                  55                  60
Glu Ala Lys Pro Ser Ala Thr Gly Lys Val Ile Asp Lys Lys Leu Pro
 65                  70                  75                  80
Lys Pro Leu Glu Lys Val Pro Met Leu Val Pro Val Pro Val Ser Glu
                 85                  90                  95
Pro Val Pro Glu Pro Glu Pro Glu Pro Glu Pro Val Lys Glu
                100                 105                 110
Glu Lys Leu Ser Pro Glu Pro Ile Leu Val Asp Thr Ala Ser Pro Ser
            115                 120                 125
Pro Met Glu Thr Ser Gly Cys Ala Pro Ala Glu Glu Asp Leu Cys Gln
            130                 135                 140
Ala Phe Ser Asp Val Ile Leu Ala Val Asn Asp Val Asp Ala Glu Asp
145                 150                 155                 160
Gly Ala Asp Pro Asn Leu Cys Ser Glu Tyr Val Lys Asp Ile Tyr Ala
                165                 170                 175
Tyr Leu Arg Gln Leu Glu Glu Glu Gln Ala Val Arg Pro Lys Tyr Leu
            180                 185                 190
Leu Gly Arg Glu Val Thr Gly Asn Met Arg Ala Ile Leu Ile Asp Trp
            195                 200                 205
Leu Val Gln Val Gln Met Lys Phe Arg Leu Leu Gln Glu Thr Met Tyr
210                 215                 220
Met Thr Val Ser Ile Ile Asp Arg Phe Met Gln Asn Asn Cys Val Pro
225                 230                 235                 240
Lys Lys Met Leu Gln Leu Val Gly Val Thr Ala Met Phe Ile Ala Ser
                245                 250                 255
Lys Tyr Glu Glu Met Tyr Pro Pro Glu Ile Gly Asp Phe Ala Phe Val
            260                 265                 270
Thr Asp Asn Thr Tyr Thr Lys His Gln Ile Arg Gln Met Glu Met Lys
            275                 280                 285
Ile Leu Arg Ala Leu Asn Phe Gly Leu Gly Arg Pro Leu Pro Leu His
290                 295                 300
Phe Leu Arg Arg Ala Ser Lys Ile Gly Glu Val Asp Val Glu Gln His
305                 310                 315                 320
Thr Leu Ala Lys Tyr Leu Met Glu Leu Thr Met Leu Asp Tyr Asp Met
                325                 330                 335
Val His Phe Pro Pro Ser Gln Ile Ala Ala Gly Ala Phe Cys Leu Ala
            340                 345                 350
Leu Lys Ile Leu Asp Asn Gly Glu Trp Thr Pro Thr Leu Gln His Tyr
            355                 360                 365
Leu Ser Tyr Thr Glu Glu Ser Leu Leu Pro Val Met Gln His Leu Ala
            370                 375                 380
Lys Asn Val Val Met Val Asn Gln Gly Leu Thr Lys His Met Thr Val
385                 390                 395                 400
Lys Asn Lys Tyr Ala Thr Ser Lys His Ala Lys Ile Ser Thr Leu Pro
                405                 410                 415
Gln Leu Asn Ser Ala Leu Val Gln Asp Leu Ala Lys Ala Val Ala Lys
            420                 425                 430
Val
```

```
<210> SEQ ID NO 32
<211> LENGTH: 142
<212> TYPE: PRT
<213> ORGANISM: Homo sapiens

<400> SEQUENCE: 32

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Pro Ile Glu His Lys Lys His
65                  70                  75                  80

Ser Ser Gly Cys Ala Phe Leu Ser Val Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Lys Glu Phe Glu Glu Thr Ala
        115                 120                 125

Glu Lys Val Arg Arg Ala Ile Glu Gln Leu Ala Ala Met Asp
    130                 135                 140

<210> SEQ ID NO 33
<211> LENGTH: 3256
<212> TYPE: PRT
<213> ORGANISM: Homo sapiens

<400> SEQUENCE: 33

Met Trp Pro Thr Arg Arg Leu Val Thr Ile Lys Arg Ser Gly Val Asp
1               5                   10                  15

Gly Pro His Phe Pro Leu Ser Leu Ser Thr Cys Leu Phe Gly Arg Gly
            20                  25                  30

Ile Glu Cys Asp Ile Arg Ile Gln Leu Pro Val Val Ser Lys Gln His
        35                  40                  45

Cys Lys Ile Glu Ile His Glu Gln Glu Ala Ile Leu His Asn Phe Ser
    50                  55                  60

Ser Thr Asn Pro Thr Gln Val Asn Gly Ser Val Ile Asp Glu Pro Val
65                  70                  75                  80

Arg Leu Lys His Gly Asp Val Ile Thr Ile Asp Arg Ser Phe Arg
                85                  90                  95

Tyr Glu Asn Glu Ser Leu Gln Asn Gly Arg Lys Ser Thr Glu Phe Pro
            100                 105                 110

Arg Lys Ile Arg Glu Gln Glu Pro Ala Arg Arg Val Ser Arg Ser Ser
        115                 120                 125

Phe Ser Ser Asp Pro Asp Glu Lys Ala Gln Asp Ser Lys Ala Tyr Ser
    130                 135                 140

Lys Ile Thr Glu Gly Lys Val Ser Gly Asn Pro Gln Val His Ile Lys
145                 150                 155                 160

Asn Val Lys Glu Asp Ser Thr Ala Asp Ser Lys Asp Ser Val Ala
                165                 170                 175

Gln Gly Thr Thr Asn Val His Ser Ser Glu His Ala Gly Arg Asn Gly
            180                 185                 190
```

-continued

```
Arg Asn Ala Ala Asp Pro Ile Ser Gly Asp Phe Lys Glu Ile Ser Ser
        195                 200                 205

Val Lys Leu Val Ser Arg Tyr Gly Glu Leu Lys Ser Val Pro Thr Thr
    210                 215                 220

Gln Cys Leu Asp Asn Ser Lys Lys Asn Glu Ser Pro Phe Trp Lys Leu
225                 230                 235                 240

Tyr Glu Ser Val Lys Lys Glu Leu Asp Val Lys Ser Gln Lys Glu Asn
                245                 250                 255

Val Leu Gln Tyr Cys Arg Lys Ser Gly Leu Gln Thr Asp Tyr Ala Thr
                260                 265                 270

Glu Lys Glu Ser Ala Asp Gly Leu Gln Gly Glu Thr Gln Leu Leu Val
        275                 280                 285

Ser Arg Lys Ser Arg Pro Lys Ser Gly Ser Gly His Ala Val Ala
    290                 295                 300

Glu Pro Ala Ser Pro Glu Gln Glu Leu Asp Gln Asn Lys Gly Lys Gly
305                 310                 315                 320

Arg Asp Val Glu Ser Val Gln Thr Pro Ser Lys Ala Val Gly Ala Ser
                325                 330                 335

Phe Pro Leu Tyr Glu Pro Ala Lys Met Lys Thr Pro Val Gln Tyr Ser
                340                 345                 350

Gln Gln Gln Asn Ser Pro Gln Lys His Lys Asn Lys Asp Leu Tyr Thr
        355                 360                 365

Thr Gly Arg Arg Glu Ser Val Asn Leu Gly Lys Ser Glu Gly Phe Lys
    370                 375                 380

Ala Gly Asp Lys Thr Leu Thr Pro Arg Lys Leu Ser Thr Arg Asn Arg
385                 390                 395                 400

Thr Pro Ala Lys Val Glu Asp Ala Ala Asp Ser Ala Thr Lys Pro Glu
                405                 410                 415

Asn Leu Ser Ser Lys Thr Arg Gly Ser Ile Pro Thr Asp Val Glu Val
                420                 425                 430

Leu Pro Thr Glu Thr Glu Ile His Asn Glu Pro Phe Leu Thr Leu Trp
        435                 440                 445

Leu Thr Gln Val Glu Arg Lys Ile Gln Lys Asp Ser Leu Ser Lys Pro
    450                 455                 460

Glu Lys Leu Gly Thr Thr Ala Gly Gln Met Cys Ser Gly Leu Pro Gly
465                 470                 475                 480

Leu Ser Ser Val Asp Ile Asn Asn Phe Gly Asp Ser Ile Asn Glu Ser
                485                 490                 495

Glu Gly Ile Pro Leu Lys Arg Arg Val Ser Phe Gly Gly His Leu
                500                 505                 510

Arg Pro Glu Leu Phe Asp Glu Asn Leu Pro Pro Asn Thr Pro Leu Lys
        515                 520                 525

Arg Gly Glu Ala Pro Thr Lys Arg Lys Ser Leu Val Met His Thr Pro
    530                 535                 540

Pro Val Leu Lys Lys Ile Ile Lys Glu Gln Pro Gln Pro Ser Gly Lys
545                 550                 555                 560

Gln Glu Ser Gly Ser Glu Ile His Val Glu Val Lys Ala Gln Ser Leu
                565                 570                 575

Val Ile Ser Pro Pro Ala Pro Ser Pro Arg Lys Thr Pro Val Ala Ser
                580                 585                 590

Asp Gln Arg Arg Arg Ser Cys Lys Thr Ala Pro Ala Ser Ser Ser Lys
        595                 600                 605

Ser Gln Thr Glu Val Pro Lys Arg Gly Gly Arg Lys Ser Gly Asn Leu
```

-continued

```
            610                 615                 620
Pro Ser Lys Arg Val Ser Ile Ser Arg Ser Gln His Asp Ile Leu Gln
625                 630                 635                 640

Met Ile Cys Ser Lys Arg Arg Ser Gly Ala Ser Glu Ala Asn Leu Ile
                645                 650                 655

Val Ala Lys Ser Trp Ala Asp Val Val Lys Leu Gly Ala Lys Gln Thr
                660                 665                 670

Gln Thr Lys Val Ile Lys His Gly Pro Gln Arg Ser Met Asn Lys Arg
                675                 680                 685

Gln Arg Arg Pro Ala Thr Pro Lys Lys Pro Val Gly Glu Val His Ser
690                 695                 700

Gln Phe Ser Thr Gly His Ala Asn Ser Pro Cys Thr Ile Ile Ile Gly
705                 710                 715                 720

Lys Ala His Thr Glu Lys Val His Val Pro Ala Arg Pro Tyr Arg Val
                725                 730                 735

Leu Asn Asn Phe Ile Ser Asn Gln Lys Met Asp Phe Lys Glu Asp Leu
                740                 745                 750

Ser Gly Ile Ala Glu Met Phe Lys Thr Pro Val Lys Glu Gln Pro Gln
            755                 760                 765

Leu Thr Ser Thr Cys His Ile Ala Ile Ser Asn Ser Glu Asn Leu Leu
            770                 775                 780

Gly Lys Gln Phe Gln Gly Thr Asp Ser Gly Glu Glu Pro Leu Leu Pro
785                 790                 795                 800

Thr Ser Glu Ser Phe Gly Gly Asn Val Phe Phe Ser Ala Gln Asn Ala
                805                 810                 815

Ala Lys Gln Pro Ser Asp Lys Cys Ser Ala Ser Pro Pro Leu Arg Arg
                820                 825                 830

Gln Cys Ile Arg Glu Asn Gly Asn Val Ala Lys Thr Pro Arg Asn Thr
            835                 840                 845

Tyr Lys Met Thr Ser Leu Glu Thr Lys Thr Ser Asp Thr Glu Thr Glu
            850                 855                 860

Pro Ser Lys Thr Val Ser Thr Ala Asn Arg Ser Gly Arg Ser Thr Glu
865                 870                 875                 880

Phe Arg Asn Ile Gln Lys Leu Pro Val Glu Ser Lys Ser Glu Glu Thr
                885                 890                 895

Asn Thr Glu Ile Val Glu Cys Ile Leu Lys Arg Gly Gln Lys Ala Thr
                900                 905                 910

Leu Leu Gln Gln Arg Arg Glu Gly Glu Met Lys Glu Ile Glu Arg Pro
            915                 920                 925

Phe Glu Thr Tyr Lys Glu Asn Ile Glu Leu Lys Glu Asn Asp Glu Lys
            930                 935                 940

Met Lys Ala Met Lys Arg Ser Arg Thr Trp Gly Gln Lys Cys Ala Pro
945                 950                 955                 960

Met Ser Asp Leu Thr Asp Leu Lys Ser Leu Pro Asp Thr Glu Leu Met
                965                 970                 975

Lys Asp Thr Ala Arg Gly Gln Asn Leu Leu Gln Thr Gln Asp His Ala
                980                 985                 990

Lys Ala Pro Lys Ser Glu Lys Gly Lys Ile Thr Lys Met Pro Cys Gln
            995                 1000                1005

Ser Leu Gln Pro Glu Pro Ile Asn Thr Pro Thr His Thr Lys Gln
    1010                1015                1020

Gln Leu Lys Ala Ser Leu Gly Lys Val Gly Val Lys Glu Glu Leu
    1025                1030                1035
```

-continued

```
Leu Ala Val Gly Lys Phe Thr Arg Thr Ser Gly Glu Thr Thr His
    1040                1045                1050

Thr His Arg Glu Pro Ala Gly Asp Gly Lys Ser Ile Arg Thr Phe
    1055                1060                1065

Lys Glu Ser Pro Lys Gln Ile Leu Asp Pro Ala Ala Arg Val Thr
    1070                1075                1080

Gly Met Lys Lys Trp Pro Arg Thr Pro Lys Glu Glu Ala Gln Ser
    1085                1090                1095

Leu Glu Asp Leu Ala Gly Phe Lys Glu Leu Phe Gln Thr Pro Gly
    1100                1105                1110

Pro Ser Glu Glu Ser Met Thr Asp Glu Lys Thr Thr Lys Ile Ala
    1115                1120                1125

Cys Lys Ser Pro Pro Glu Ser Val Asp Thr Pro Thr Ser Thr
    1130                1135                1140

Lys Gln Trp Pro Lys Arg Ser Leu Arg Lys Ala Asp Val Glu Glu
    1145                1150                1155

Glu Phe Leu Ala Leu Arg Lys Leu Thr Pro Ser Ala Gly Lys Ala
    1160                1165                1170

Met Leu Thr Pro Lys Pro Ala Gly Gly Asp Glu Lys Asp Ile Lys
    1175                1180                1185

Ala Phe Met Gly Thr Pro Val Gln Lys Leu Asp Leu Ala Gly Thr
    1190                1195                1200

Leu Pro Gly Ser Lys Arg Gln Leu Gln Thr Pro Lys Glu Lys Ala
    1205                1210                1215

Gln Ala Leu Glu Asp Leu Ala Gly Phe Lys Glu Leu Phe Gln Thr
    1220                1225                1230

Pro Gly His Thr Glu Glu Leu Val Ala Ala Gly Lys Thr Thr Lys
    1235                1240                1245

Ile Pro Cys Asp Ser Pro Gln Ser Asp Pro Val Asp Thr Pro Thr
    1250                1255                1260

Ser Thr Lys Gln Arg Pro Lys Arg Ser Ile Arg Lys Ala Asp Val
    1265                1270                1275

Glu Gly Glu Leu Leu Ala Cys Arg Asn Leu Met Pro Ser Ala Gly
    1280                1285                1290

Lys Ala Met His Thr Pro Lys Pro Ser Val Gly Glu Glu Lys Asp
    1295                1300                1305

Ile Ile Ile Phe Val Gly Thr Pro Val Gln Lys Leu Asp Leu Thr
    1310                1315                1320

Glu Asn Leu Thr Gly Ser Lys Arg Arg Pro Gln Thr Pro Lys Glu
    1325                1330                1335

Glu Ala Gln Ala Leu Glu Asp Leu Thr Gly Phe Lys Glu Leu Phe
    1340                1345                1350

Gln Thr Pro Gly His Thr Glu Glu Ala Val Ala Ala Gly Lys Thr
    1355                1360                1365

Thr Lys Met Pro Cys Glu Ser Ser Pro Pro Glu Ser Ala Asp Thr
    1370                1375                1380

Pro Thr Ser Thr Arg Arg Gln Pro Lys Thr Pro Leu Glu Lys Arg
    1385                1390                1395

Asp Val Gln Lys Glu Leu Ser Ala Leu Lys Lys Leu Thr Gln Thr
    1400                1405                1410

Ser Gly Glu Thr Thr His Thr Asp Lys Val Pro Gly Gly Glu Asp
    1415                1420                1425
```

-continued

```
Lys Ser Ile Asn Ala Phe Arg Glu Thr Ala Lys Gln Lys Leu Asp
1430                1435                1440

Pro Ala Ala Ser Val Thr Gly Ser Lys Arg His Pro Lys Thr Lys
1445                1450                1455

Glu Lys Ala Gln Pro Leu Glu Asp Leu Ala Gly Leu Lys Glu Leu
1460                1465                1470

Phe Gln Thr Pro Val Cys Thr Asp Lys Pro Thr Thr His Glu Lys
1475                1480                1485

Thr Thr Lys Ile Ala Cys Arg Ser Gln Pro Asp Pro Val Asp Thr
1490                1495                1500

Pro Thr Ser Ser Lys Pro Gln Ser Lys Arg Ser Leu Arg Lys Val
1505                1510                1515

Asp Val Glu Glu Phe Phe Ala Leu Arg Lys Arg Thr Pro Ser
1520                1525                1530

Ala Gly Lys Ala Met His Thr Pro Lys Pro Ala Val Ser Gly Glu
1535                1540                1545

Lys Asn Ile Tyr Ala Phe Met Gly Thr Pro Val Gln Lys Leu Asp
1550                1555                1560

Leu Thr Glu Asn Leu Thr Gly Ser Lys Arg Arg Leu Gln Thr Pro
1565                1570                1575

Lys Glu Lys Ala Gln Ala Leu Glu Asp Leu Ala Gly Phe Lys Glu
1580                1585                1590

Leu Phe Gln Thr Arg Gly His Thr Glu Glu Ser Met Thr Asn Asp
1595                1600                1605

Lys Thr Ala Lys Val Ala Cys Lys Ser Ser Gln Pro Asp Pro Asp
1610                1615                1620

Lys Asn Pro Ala Ser Ser Lys Arg Arg Leu Lys Thr Ser Leu Gly
1625                1630                1635

Lys Val Gly Val Lys Glu Glu Leu Leu Ala Val Gly Lys Leu Thr
1640                1645                1650

Gln Thr Ser Gly Glu Thr Thr His Thr His Thr Glu Pro Thr Gly
1655                1660                1665

Asp Gly Lys Ser Met Lys Ala Phe Met Glu Ser Pro Lys Gln Ile
1670                1675                1680

Leu Asp Ser Ala Ala Ser Leu Thr Gly Ser Lys Arg Gln Leu Arg
1685                1690                1695

Thr Pro Lys Gly Lys Ser Glu Val Pro Glu Asp Leu Ala Gly Phe
1700                1705                1710

Ile Glu Leu Phe Gln Thr Pro Ser His Thr Lys Glu Ser Met Thr
1715                1720                1725

Asn Glu Lys Thr Thr Lys Val Ser Tyr Arg Ala Ser Gln Pro Asp
1730                1735                1740

Leu Val Asp Thr Pro Thr Ser Ser Lys Pro Gln Pro Lys Arg Ser
1745                1750                1755

Leu Arg Lys Ala Asp Thr Glu Glu Phe Leu Ala Phe Arg Lys
1760                1765                1770

Gln Thr Pro Ser Ala Gly Lys Ala Met His Thr Pro Lys Pro Ala
1775                1780                1785

Val Gly Glu Glu Lys Asp Ile Asn Thr Phe Leu Gly Thr Pro Val
1790                1795                1800

Gln Lys Leu Asp Gln Pro Gly Asn Leu Pro Gly Ser Asn Arg Arg
1805                1810                1815

Leu Gln Thr Arg Lys Glu Lys Ala Gln Ala Leu Glu Glu Leu Thr
```

-continued

```
                1820                1825                1830
Gly Phe Arg Glu Leu Phe Gln Thr Pro Cys Thr Asp Asn Pro Thr
    1835                1840                1845

Thr Asp Glu Lys Thr Thr Lys Lys Ile Leu Cys Lys Ser Pro Gln
    1850                1855                1860

Ser Asp Pro Ala Asp Thr Pro Thr Asn Thr Lys Gln Arg Pro Lys
    1865                1870                1875

Arg Ser Leu Lys Lys Ala Asp Val Glu Glu Glu Phe Leu Ala Phe
    1880                1885                1890

Arg Lys Leu Thr Pro Ser Ala Gly Lys Ala Met His Thr Pro Lys
    1895                1900                1905

Ala Ala Val Gly Glu Glu Lys Asp Ile Asn Thr Phe Val Gly Thr
    1910                1915                1920

Pro Val Glu Lys Leu Asp Leu Leu Gly Asn Leu Pro Gly Ser Lys
    1925                1930                1935

Arg Arg Pro Gln Thr Pro Lys Glu Lys Ala Lys Ala Leu Glu Asp
    1940                1945                1950

Leu Ala Gly Phe Lys Glu Leu Phe Gln Thr Pro Gly His Thr Glu
    1955                1960                1965

Glu Ser Met Thr Asp Asp Lys Ile Thr Glu Val Ser Cys Lys Ser
    1970                1975                1980

Pro Gln Pro Asp Pro Val Lys Thr Pro Thr Ser Ser Lys Gln Arg
    1985                1990                1995

Leu Lys Ile Ser Leu Gly Lys Val Gly Val Lys Glu Glu Val Leu
    2000                2005                2010

Pro Val Gly Lys Leu Thr Gln Thr Ser Gly Lys Thr Thr Gln Thr
    2015                2020                2025

His Arg Glu Thr Ala Gly Asp Gly Lys Ser Ile Lys Ala Phe Lys
    2030                2035                2040

Glu Ser Ala Lys Gln Met Leu Asp Pro Ala Asn Tyr Gly Thr Gly
    2045                2050                2055

Met Glu Arg Trp Pro Arg Thr Pro Lys Glu Glu Ala Gln Ser Leu
    2060                2065                2070

Glu Asp Leu Ala Gly Phe Lys Glu Leu Phe Gln Thr Pro Asp His
    2075                2080                2085

Thr Glu Glu Ser Thr Thr Asp Asp Lys Thr Thr Lys Ile Ala Cys
    2090                2095                2100

Lys Ser Pro Pro Pro Glu Ser Met Asp Thr Pro Thr Ser Thr Arg
    2105                2110                2115

Arg Arg Pro Lys Thr Pro Leu Gly Lys Arg Asp Ile Val Glu Glu
    2120                2125                2130

Leu Ser Ala Leu Lys Gln Leu Thr Gln Thr Thr His Thr Asp Lys
    2135                2140                2145

Val Pro Gly Asp Glu Asp Lys Gly Ile Asn Val Phe Arg Glu Thr
    2150                2155                2160

Ala Lys Gln Lys Leu Asp Pro Ala Ala Ser Val Thr Gly Ser Lys
    2165                2170                2175

Arg Gln Pro Arg Thr Pro Lys Gly Lys Ala Gln Pro Leu Glu Asp
    2180                2185                2190

Leu Ala Gly Leu Lys Glu Leu Phe Gln Thr Pro Ile Cys Thr Asp
    2195                2200                2205

Lys Pro Thr Thr His Glu Lys Thr Thr Lys Ile Ala Cys Arg Ser
    2210                2215                2220
```

-continued

```
Pro Gln Pro Asp Pro Val Gly Thr Pro Thr Ile Phe Lys Pro Gln
    2225                2230                2235

Ser Lys Arg Ser Leu Arg Lys Ala Asp Val Glu Glu Glu Ser Leu
    2240                2245                2250

Ala Leu Arg Lys Arg Thr Pro Ser Val Gly Lys Ala Met Asp Thr
    2255                2260                2265

Pro Lys Pro Ala Gly Gly Asp Glu Lys Asp Met Lys Ala Phe Met
    2270                2275                2280

Gly Thr Pro Val Gln Lys Leu Asp Leu Pro Gly Asn Leu Pro Gly
    2285                2290                2295

Ser Lys Arg Trp Pro Gln Thr Pro Lys Glu Lys Ala Gln Ala Leu
    2300                2305                2310

Glu Asp Leu Ala Gly Phe Lys Glu Leu Phe Gln Thr Pro Gly Thr
    2315                2320                2325

Asp Lys Pro Thr Thr Asp Glu Lys Thr Thr Lys Ile Ala Cys Lys
    2330                2335                2340

Ser Pro Gln Pro Asp Pro Val Asp Thr Pro Ala Ser Thr Lys Gln
    2345                2350                2355

Arg Pro Lys Arg Asn Leu Arg Lys Ala Asp Val Glu Glu Glu Phe
    2360                2365                2370

Leu Ala Leu Arg Lys Arg Thr Pro Ser Ala Gly Lys Ala Met Asp
    2375                2380                2385

Thr Pro Lys Pro Ala Val Ser Asp Glu Lys Asn Ile Asn Thr Phe
    2390                2395                2400

Val Glu Thr Pro Val Gln Lys Leu Asp Leu Leu Gly Asn Leu Pro
    2405                2410                2415

Gly Ser Lys Arg Gln Pro Gln Thr Pro Lys Glu Lys Ala Glu Ala
    2420                2425                2430

Leu Glu Asp Leu Val Gly Phe Lys Glu Leu Phe Gln Thr Pro Gly
    2435                2440                2445

His Thr Glu Glu Ser Met Thr Asp Asp Lys Ile Thr Glu Val Ser
    2450                2455                2460

Cys Lys Ser Pro Gln Pro Glu Ser Phe Lys Thr Ser Arg Ser Ser
    2465                2470                2475

Lys Gln Arg Leu Lys Ile Pro Leu Val Lys Val Asp Met Lys Glu
    2480                2485                2490

Glu Pro Leu Ala Val Ser Lys Leu Thr Arg Thr Ser Gly Glu Thr
    2495                2500                2505

Thr Gln Thr His Thr Glu Pro Thr Gly Asp Ser Lys Ser Ile Lys
    2510                2515                2520

Ala Phe Lys Glu Ser Pro Lys Gln Ile Leu Asp Pro Ala Ala Ser
    2525                2530                2535

Val Thr Gly Ser Arg Arg Gln Leu Arg Thr Arg Lys Glu Lys Ala
    2540                2545                2550

Arg Ala Leu Glu Asp Leu Val Asp Phe Lys Glu Leu Phe Ser Ala
    2555                2560                2565

Pro Gly His Thr Glu Glu Ser Met Thr Ile Asp Lys Asn Thr Lys
    2570                2575                2580

Ile Pro Cys Lys Ser Pro Pro Pro Glu Leu Thr Asp Thr Ala Thr
    2585                2590                2595

Ser Thr Lys Arg Cys Pro Lys Thr Arg Pro Arg Lys Glu Val Lys
    2600                2605                2610
```

-continued

```
Glu Glu Leu Ser Ala Val Glu Arg Leu Thr Gln Thr Ser Gly Gln
2615                2620                2625

Ser Thr His Thr His Lys Glu Pro Ala Ser Gly Asp Glu Gly Ile
2630                2635                2640

Lys Val Leu Lys Gln Arg Ala Lys Lys Lys Pro Asn Pro Val Glu
2645                2650                2655

Glu Glu Pro Ser Arg Arg Pro Arg Ala Pro Lys Glu Lys Ala
2660                2665                2670

Gln Pro Leu Glu Asp Leu Ala Gly Phe Thr Glu Leu Ser Glu Thr
2675                2680                2685

Ser Gly His Thr Gln Glu Ser Leu Thr Ala Gly Lys Ala Thr Lys
2690                2695                2700

Ile Pro Cys Glu Ser Pro Pro Leu Glu Val Val Asp Thr Thr Ala
2705                2710                2715

Ser Thr Lys Arg His Leu Arg Thr Arg Val Gln Lys Val Gln Val
2720                2725                2730

Lys Glu Glu Pro Ser Ala Val Lys Phe Thr Gln Thr Ser Gly Glu
2735                2740                2745

Thr Thr Asp Ala Asp Lys Glu Pro Ala Gly Glu Asp Lys Gly Ile
2750                2755                2760

Lys Ala Leu Lys Glu Ser Ala Lys Gln Thr Pro Ala Pro Ala Ala
2765                2770                2775

Ser Val Thr Gly Ser Arg Arg Arg Pro Arg Ala Pro Arg Glu Ser
2780                2785                2790

Ala Gln Ala Ile Glu Asp Leu Ala Gly Phe Lys Asp Pro Ala Ala
2795                2800                2805

Gly His Thr Glu Glu Ser Met Thr Asp Asp Lys Thr Thr Lys Ile
2810                2815                2820

Pro Cys Lys Ser Ser Pro Glu Leu Glu Asp Thr Ala Thr Ser Ser
2825                2830                2835

Lys Arg Arg Pro Arg Thr Arg Ala Gln Lys Val Glu Val Lys Glu
2840                2845                2850

Glu Leu Leu Ala Val Gly Lys Leu Thr Gln Thr Ser Gly Glu Thr
2855                2860                2865

Thr His Thr Asp Lys Glu Pro Val Gly Glu Gly Lys Gly Thr Lys
2870                2875                2880

Ala Phe Lys Gln Pro Ala Lys Arg Lys Leu Asp Ala Glu Asp Val
2885                2890                2895

Ile Gly Ser Arg Arg Gln Pro Arg Ala Pro Lys Glu Lys Ala Gln
2900                2905                2910

Pro Leu Glu Asp Leu Ala Ser Phe Gln Glu Leu Ser Gln Thr Pro
2915                2920                2925

Gly His Thr Glu Glu Leu Ala Asn Gly Ala Ala Asp Ser Phe Thr
2930                2935                2940

Ser Ala Pro Lys Gln Thr Pro Asp Ser Gly Lys Pro Leu Lys Ile
2945                2950                2955

Ser Arg Arg Val Leu Arg Ala Pro Lys Val Glu Pro Val Gly Asp
2960                2965                2970

Val Val Ser Thr Arg Asp Pro Val Lys Ser Gln Ser Lys Ser Asn
2975                2980                2985

Thr Ser Leu Pro Pro Leu Pro Phe Lys Arg Gly Gly Lys Asp
2990                2995                3000

Gly Ser Val Thr Gly Thr Lys Arg Leu Arg Cys Met Pro Ala Pro
```

```
                3005                3010                3015

Glu Glu Ile Val Glu Glu Leu Pro Ala Ser Lys Lys Gln Arg Val
    3020                3025                3030

Ala Pro Arg Ala Arg Gly Lys Ser Ser Glu Pro Val Val Ile Met
    3035                3040                3045

Lys Arg Ser Leu Arg Thr Ser Ala Lys Arg Ile Glu Pro Ala Glu
    3050                3055                3060

Glu Leu Asn Ser Asn Asp Met Lys Thr Asn Lys Glu Glu His Lys
    3065                3070                3075

Leu Gln Asp Ser Val Pro Glu Asn Lys Gly Ile Ser Leu Arg Ser
    3080                3085                3090

Arg Arg Gln Asn Lys Thr Glu Ala Glu Gln Gln Ile Thr Glu Val
    3095                3100                3105

Phe Val Leu Ala Glu Arg Ile Glu Ile Asn Arg Asn Glu Lys Lys
    3110                3115                3120

Pro Met Lys Thr Ser Pro Glu Met Asp Ile Gln Asn Pro Asp Asp
    3125                3130                3135

Gly Ala Arg Lys Pro Ile Pro Arg Asp Lys Val Thr Glu Asn Lys
    3140                3145                3150

Arg Cys Leu Arg Ser Ala Arg Gln Asn Glu Ser Ser Gln Pro Lys
    3155                3160                3165

Val Ala Glu Glu Ser Gly Gly Gln Lys Ser Ala Lys Val Leu Met
    3170                3175                3180

Gln Asn Gln Lys Gly Lys Gly Glu Ala Gly Asn Ser Asp Ser Met
    3185                3190                3195

Cys Leu Arg Ser Arg Lys Thr Lys Ser Gln Pro Ala Ala Ser Thr
    3200                3205                3210

Leu Glu Ser Lys Ser Val Gln Arg Val Thr Arg Ser Val Lys Arg
    3215                3220                3225

Cys Ala Glu Asn Pro Lys Lys Ala Glu Asp Asn Val Cys Val Lys
    3230                3235                3240

Lys Ile Arg Thr Arg Ser His Arg Asp Ser Glu Asp Ile
    3245                3250                3255

<210> SEQ ID NO 34
<211> LENGTH: 403
<212> TYPE: PRT
<213> ORGANISM: Homo sapiens

<400> SEQUENCE: 34

Met Asp Arg Ser Lys Glu Asn Cys Ile Ser Gly Pro Val Lys Ala Thr
1               5                   10                  15

Ala Pro Val Gly Gly Pro Lys Arg Val Leu Val Thr Gln Gln Phe Pro
                20                  25                  30

Cys Gln Asn Pro Leu Pro Val Asn Ser Gly Gln Ala Gln Arg Val Leu
            35                  40                  45

Cys Pro Ser Asn Ser Ser Gln Arg Ile Pro Leu Gln Ala Gln Lys Leu
        50                  55                  60

Val Ser Ser His Lys Pro Val Asn Gln Lys Gln Lys Gln Leu Gln
65                  70                  75                  80

Ala Thr Ser Val Pro His Pro Val Ser Arg Pro Leu Asn Asn Thr Gln
                85                  90                  95

Lys Ser Lys Gln Pro Leu Pro Ser Ala Pro Glu Asn Asn Pro Glu Glu
            100                 105                 110
```

```
Glu Leu Ala Ser Lys Gln Lys Asn Glu Glu Ser Lys Lys Arg Gln Trp
            115                 120                 125

Ala Leu Glu Asp Phe Glu Ile Gly Arg Pro Leu Gly Lys Gly Lys Phe
            130                 135                 140

Gly Asn Val Tyr Leu Ala Arg Glu Lys Gln Ser Lys Phe Ile Leu Ala
145                 150                 155                 160

Leu Lys Val Leu Phe Lys Ala Gln Leu Glu Lys Ala Gly Val Glu His
                165                 170                 175

Gln Leu Arg Arg Glu Val Glu Ile Gln Ser His Leu Arg His Pro Asn
            180                 185                 190

Ile Leu Arg Leu Tyr Gly Tyr Phe His Asp Ala Thr Arg Val Tyr Leu
            195                 200                 205

Ile Leu Glu Tyr Ala Pro Leu Gly Thr Val Tyr Arg Glu Leu Gln Lys
            210                 215                 220

Leu Ser Lys Phe Asp Glu Gln Arg Thr Ala Thr Tyr Ile Thr Glu Leu
225                 230                 235                 240

Ala Asn Ala Leu Ser Tyr Cys His Ser Lys Arg Val Ile His Arg Asp
                245                 250                 255

Ile Lys Pro Glu Asn Leu Leu Leu Gly Ser Ala Gly Glu Leu Lys Ile
            260                 265                 270

Ala Asp Phe Gly Trp Ser Val His Ala Pro Ser Ser Arg Arg Thr Thr
            275                 280                 285

Leu Cys Gly Thr Leu Asp Tyr Leu Pro Pro Glu Met Ile Glu Gly Arg
290                 295                 300

Met His Asp Glu Lys Val Asp Leu Trp Ser Leu Gly Val Leu Cys Tyr
305                 310                 315                 320

Glu Phe Leu Val Gly Lys Pro Pro Phe Glu Ala Asn Thr Tyr Gln Glu
                325                 330                 335

Thr Tyr Lys Arg Ile Ser Arg Val Glu Phe Thr Phe Pro Asp Phe Val
            340                 345                 350

Thr Glu Gly Ala Arg Asp Leu Ile Ser Arg Leu Leu Lys His Asn Pro
            355                 360                 365

Ser Gln Arg Pro Met Leu Arg Glu Val Leu Glu His Pro Trp Ile Thr
            370                 375                 380

Ala Asn Ser Ser Lys Pro Ser Asn Cys Gln Asn Lys Glu Ser Ala Ser
385                 390                 395                 400

Lys Gln Ser

<210> SEQ ID NO 35
<211> LENGTH: 480
<212> TYPE: PRT
<213> ORGANISM: Homo sapiens

<400> SEQUENCE: 35

Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80
```

```
Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
        435                 440                 445

Ile Thr Pro Pro Asp Gln Asp Asp Ser Met Glu Cys Val Asp Ser Glu
450                 455                 460

Arg Arg Pro His Phe Pro Gln Phe Ser Tyr Ser Ala Ser Gly Thr Ala
465                 470                 475                 480

<210> SEQ ID NO 36
<211> LENGTH: 354
<212> TYPE: PRT
```

<213> ORGANISM: Homo sapiens

<400> SEQUENCE: 36

```
Met Arg Leu Ala Val Leu Phe Ser Gly Ala Leu Leu Gly Leu Leu Ala
1               5                   10                  15

Ala Gln Gly Thr Gly Asn Asp Cys Pro His Lys Lys Ser Ala Thr Leu
            20                  25                  30

Leu Pro Ser Phe Thr Val Thr Pro Thr Val Thr Glu Ser Thr Gly Thr
        35                  40                  45

Thr Ser His Arg Thr Thr Lys Ser His Lys Thr Thr Thr His Arg Thr
50                  55                  60

Thr Thr Thr Gly Thr Thr Ser His Gly Pro Thr Thr Ala Thr His Asn
65                  70                  75                  80

Pro Thr Thr Thr Ser His Gly Asn Val Thr Val His Pro Thr Ser Asn
                85                  90                  95

Ser Thr Ala Thr Ser Gln Gly Pro Ser Thr Ala Thr His Ser Pro Ala
            100                 105                 110

Thr Thr Ser His Gly Asn Ala Thr Val His Pro Thr Ser Asn Ser Thr
        115                 120                 125

Ala Thr Ser Pro Gly Phe Thr Ser Ser Ala His Pro Glu Pro Pro
130                 135                 140

Pro Ser Pro Ser Pro Ser Pro Thr Ser Lys Glu Thr Ile Gly Asp Tyr
145                 150                 155                 160

Thr Trp Thr Asn Gly Ser Gln Pro Cys Val His Leu Gln Ala Gln Ile
                165                 170                 175

Gln Ile Arg Val Met Tyr Thr Thr Gln Gly Gly Gly Glu Ala Trp Gly
            180                 185                 190

Ile Ser Val Leu Asn Pro Asn Lys Thr Lys Val Gln Gly Ser Cys Glu
        195                 200                 205

Gly Ala His Pro His Leu Leu Leu Ser Phe Pro Tyr Gly His Leu Ser
210                 215                 220

Phe Gly Phe Met Gln Asp Leu Gln Gln Lys Val Val Tyr Leu Ser Tyr
225                 230                 235                 240

Met Ala Val Glu Tyr Asn Val Ser Phe Pro His Ala Ala Gln Trp Thr
                245                 250                 255

Phe Ser Ala Gln Asn Ala Ser Leu Arg Asp Leu Gln Ala Pro Leu Gly
            260                 265                 270

Gln Ser Phe Ser Cys Ser Asn Ser Ser Ile Ile Leu Ser Pro Ala Val
        275                 280                 285

His Leu Asp Leu Leu Ser Leu Arg Leu Gln Ala Ala Gln Leu Pro His
290                 295                 300

Thr Gly Val Phe Gly Gln Ser Phe Ser Cys Pro Ser Asp Arg Ser Ile
305                 310                 315                 320

Leu Leu Pro Leu Ile Ile Gly Leu Ile Leu Gly Leu Leu Ala Leu
                325                 330                 335

Val Leu Ile Ala Phe Cys Ile Ile Arg Arg Arg Pro Ser Ala Tyr Gln
            340                 345                 350

Ala Leu
```

<210> SEQ ID NO 37
<211> LENGTH: 345
<212> TYPE: PRT
<213> ORGANISM: Homo sapiens

<400> SEQUENCE: 37

```
Met Ala Gln Arg Gly Gly Ala Arg Arg Pro Arg Gly Asp Arg Glu Arg
1               5                   10                  15

Leu Gly Ser Arg Leu Arg Ala Leu Arg Pro Gly Arg Glu Pro Arg Gln
            20                  25                  30

Ser Glu Pro Pro Ala Gln Arg Gly Pro Pro Ser Gly Arg Pro Pro
        35                  40                  45

Ala Arg Ser Thr Ala Ser Gly His Asp Arg Pro Thr Arg Gly Ala Ala
    50                  55                  60

Ala Gly Ala Arg Arg Pro Arg Met Lys Lys Thr Arg Arg Ser
65              70                  75                  80

Thr Arg Ser Glu Glu Leu Thr Arg Ser Glu Glu Leu Thr Leu Ser Glu
                85                  90                  95

Glu Ala Thr Trp Ser Glu Glu Ala Thr Gln Ser Glu Glu Ala Thr Gln
                100                 105                 110

Gly Glu Glu Met Asn Arg Ser Gln Glu Val Thr Arg Asp Glu Glu Ser
            115                 120                 125

Thr Arg Ser Glu Glu Val Thr Arg Glu Met Ala Ala Ala Gly Leu
130                 135                 140

Thr Val Thr Val Thr His Ser Asn Glu Lys His Asp Leu His Val Thr
145                 150                 155                 160

Ser Gln Gln Gly Ser Ser Glu Pro Val Val Gln Asp Leu Ala Gln Val
                165                 170                 175

Val Glu Glu Val Ile Gly Val Pro Gln Ser Phe Gln Lys Leu Ile Phe
            180                 185                 190

Lys Gly Lys Ser Leu Lys Glu Met Glu Thr Pro Leu Ser Ala Leu Gly
            195                 200                 205

Ile Gln Asp Gly Cys Arg Val Met Leu Ile Gly Lys Lys Asn Ser Pro
    210                 215                 220

Gln Glu Glu Val Glu Leu Lys Lys Leu Lys His Leu Glu Lys Ser Val
225                 230                 235                 240

Glu Lys Ile Ala Asp Gln Leu Glu Glu Leu Asn Lys Glu Leu Thr Gly
            245                 250                 255

Ile Gln Gln Gly Phe Leu Pro Lys Asp Leu Gln Ala Glu Ala Leu Cys
            260                 265                 270

Lys Leu Asp Arg Arg Val Lys Ala Thr Ile Glu Gln Phe Met Lys Ile
            275                 280                 285

Leu Glu Glu Ile Asp Thr Leu Ile Leu Pro Glu Asn Phe Lys Asp Ser
            290                 295                 300

Arg Leu Lys Arg Lys Gly Leu Val Lys Val Gln Ala Phe Leu Ala
305                 310                 315                 320

Glu Cys Asp Thr Val Glu Gln Asn Ile Cys Gln Glu Thr Glu Arg Leu
                325                 330                 335

Gln Ser Thr Asn Phe Ala Leu Ala Glu
                340                 345

<210> SEQ ID NO 38
<211> LENGTH: 181
<212> TYPE: PRT
<213> ORGANISM: Homo sapiens

<400> SEQUENCE: 38

Met Pro Met Ile Leu Gly Tyr Trp Asp Ile Arg Gly Leu Ala His Ala
1               5                   10                  15

Ile Arg Leu Leu Leu Glu Tyr Thr Asp Ser Ser Tyr Glu Glu Lys Lys
```

-continued

```
                 20                  25                  30
Tyr Thr Met Gly Asp Ala Pro Asp Tyr Asp Arg Ser Gln Trp Leu Asn
             35                  40                  45

Glu Lys Phe Lys Leu Gly Leu Asp Phe Pro Asn Leu Pro Tyr Leu Ile
         50                  55                  60

Asp Gly Ala His Lys Ile Thr Gln Ser Asn Ala Ile Leu Cys Tyr Ile
 65                  70                  75                  80

Ala Arg Lys His Asn Leu Cys Gly Glu Thr Glu Glu Lys Ile Arg
                 85                  90                  95

Val Asp Ile Leu Glu Asn Gln Thr Met Asp Asn His Met Gln Leu Gly
             100                 105                 110

Met Ile Cys Tyr Asn Pro Glu Phe Glu Lys Leu Lys Pro Lys Tyr Leu
         115                 120                 125

Glu Glu Leu Pro Glu Lys Leu Lys Leu Tyr Ser Glu Phe Leu Gly Lys
     130                 135                 140

Arg Pro Trp Phe Ala Gly Asn Lys Gly Leu Glu Lys Ile Ser Ala Tyr
145                 150                 155                 160

Met Lys Ser Ser Arg Phe Leu Pro Arg Pro Val Phe Ser Lys Met Ala
                165                 170                 175

Val Trp Gly Asn Lys
            180

<210> SEQ ID NO 39
<211> LENGTH: 375
<212> TYPE: PRT
<213> ORGANISM: Homo sapiens

<400> SEQUENCE: 39

Met Asp Asp Asp Ile Ala Ala Leu Val Val Asp Asn Gly Ser Gly Met
 1               5                  10                  15

Cys Lys Ala Gly Phe Ala Gly Asp Asp Ala Pro Arg Ala Val Phe Pro
             20                  25                  30

Ser Ile Val Gly Arg Pro Arg His Gln Gly Val Met Val Gly Met Gly
         35                  40                  45

Gln Lys Asp Ser Tyr Val Gly Asp Glu Ala Gln Ser Lys Arg Gly Ile
     50                  55                  60

Leu Thr Leu Lys Tyr Pro Ile Glu His Gly Ile Val Thr Asn Trp Asp
 65                  70                  75                  80

Asp Met Glu Lys Ile Trp His His Thr Phe Tyr Asn Glu Leu Arg Val
                 85                  90                  95

Ala Pro Glu Glu His Pro Val Leu Leu Thr Glu Ala Pro Leu Asn Pro
             100                 105                 110

Lys Ala Asn Arg Glu Lys Met Thr Gln Ile Met Phe Glu Thr Phe Asn
         115                 120                 125

Thr Pro Ala Met Tyr Val Ala Ile Gln Ala Val Leu Ser Leu Tyr Ala
     130                 135                 140

Ser Gly Arg Thr Thr Gly Ile Val Met Asp Ser Gly Asp Gly Val Thr
145                 150                 155                 160

His Thr Val Pro Ile Tyr Glu Gly Tyr Ala Leu Pro His Ala Ile Leu
                165                 170                 175

Arg Leu Asp Leu Ala Gly Arg Asp Leu Thr Asp Tyr Leu Met Lys Ile
             180                 185                 190

Leu Thr Glu Arg Gly Tyr Ser Phe Thr Thr Thr Ala Glu Arg Glu Ile
         195                 200                 205
```

```
Val Arg Asp Ile Lys Glu Lys Leu Cys Tyr Val Ala Leu Asp Phe Glu
    210                 215                 220

Gln Glu Met Ala Thr Ala Ser Ser Ser Leu Glu Lys Ser Tyr
225                 230                 235                 240

Glu Leu Pro Asp Gly Gln Val Ile Thr Ile Gly Asn Glu Arg Phe Arg
                    245                 250                 255

Cys Pro Glu Ala Leu Phe Gln Pro Ser Phe Leu Gly Met Glu Ser Cys
                260                 265                 270

Gly Ile His Glu Thr Thr Phe Asn Ser Ile Met Lys Cys Asp Val Asp
            275                 280                 285

Ile Arg Lys Asp Leu Tyr Ala Asn Thr Val Leu Ser Gly Gly Thr Thr
        290                 295                 300

Met Tyr Pro Gly Ile Ala Asp Arg Met Gln Lys Glu Ile Thr Ala Leu
305                 310                 315                 320

Ala Pro Ser Thr Met Lys Ile Lys Ile Ile Ala Pro Pro Glu Arg Lys
                    325                 330                 335

Tyr Ser Val Trp Ile Gly Gly Ser Ile Leu Ala Ser Leu Ser Thr Phe
                340                 345                 350

Gln Gln Met Trp Ile Ser Lys Gln Glu Tyr Asp Glu Ser Gly Pro Ser
            355                 360                 365

Ile Val His Arg Lys Cys Phe
        370                 375

<210> SEQ ID NO 40
<211> LENGTH: 335
<212> TYPE: PRT
<213> ORGANISM: Homo sapiens

<400> SEQUENCE: 40

Met Gly Lys Val Lys Val Gly Val Asn Gly Phe Gly Arg Ile Gly Arg
1                   5                   10                  15

Leu Val Thr Arg Ala Ala Phe Asn Ser Gly Lys Val Asp Ile Val Ala
                20                  25                  30

Ile Asn Asp Pro Phe Ile Asp Leu Asn Tyr Met Val Tyr Met Phe Gln
            35                  40                  45

Tyr Asp Ser Thr His Gly Lys Phe His Gly Thr Val Lys Ala Glu Asn
        50                  55                  60

Gly Lys Leu Val Ile Asn Gly Asn Pro Ile Thr Ile Phe Gln Glu Arg
65                  70                  75                  80

Asp Pro Ser Lys Ile Lys Trp Gly Asp Ala Gly Ala Glu Tyr Val Val
                85                  90                  95

Glu Ser Thr Gly Val Phe Thr Thr Met Glu Lys Ala Gly Ala His Leu
                100                 105                 110

Gln Gly Gly Ala Lys Arg Val Ile Ile Ser Ala Pro Ser Ala Asp Ala
            115                 120                 125

Pro Met Phe Val Met Gly Val Asn His Glu Lys Tyr Asp Asn Ser Leu
        130                 135                 140

Lys Ile Ile Ser Asn Ala Ser Cys Thr Thr Asn Cys Leu Ala Pro Leu
145                 150                 155                 160

Ala Lys Val Ile His Asp Asn Phe Gly Ile Val Glu Gly Leu Met Thr
                165                 170                 175

Thr Val His Ala Ile Thr Ala Thr Gln Lys Thr Val Asp Gly Pro Ser
            180                 185                 190

Gly Lys Leu Trp Arg Asp Gly Arg Gly Ala Leu Gln Asn Ile Ile Pro
        195                 200                 205
```

```
Ala Ser Thr Gly Ala Ala Lys Ala Val Gly Lys Val Ile Pro Glu Leu
        210                 215                 220
Asn Gly Lys Leu Thr Gly Met Ala Phe Arg Val Pro Thr Ala Asn Val
225                 230                 235                 240
Ser Val Val Asp Leu Thr Cys Arg Leu Glu Lys Pro Ala Lys Tyr Asp
                245                 250                 255
Asp Ile Lys Lys Val Val Lys Gln Ala Ser Glu Gly Pro Leu Lys Gly
                260                 265                 270
Ile Leu Gly Tyr Thr Glu His Gln Val Val Ser Ser Asp Phe Asn Ser
                275                 280                 285
Asp Thr His Ser Ser Thr Phe Asp Ala Gly Ala Gly Ile Ala Leu Asn
        290                 295                 300
Asp His Phe Val Lys Leu Ile Ser Trp Tyr Asp Asn Glu Phe Gly Tyr
305                 310                 315                 320
Ser Asn Arg Val Val Asp Leu Met Ala His Met Ala Ser Lys Glu
                325                 330                 335

<210> SEQ ID NO 41
<211> LENGTH: 651
<212> TYPE: PRT
<213> ORGANISM: Homo sapiens

<400> SEQUENCE: 41

Met Ala Arg Gly Ser Ala Val Ala Trp Ala Ala Leu Gly Pro Leu Leu
1               5                   10                  15
Trp Gly Cys Ala Leu Gly Leu Gln Gly Gly Met Leu Tyr Pro Gln Glu
                20                  25                  30
Ser Pro Ser Arg Glu Cys Lys Glu Leu Asp Gly Leu Trp Ser Phe Arg
                35                  40                  45
Ala Asp Phe Ser Asp Asn Arg Arg Gly Phe Glu Glu Gln Trp Tyr
        50                  55                  60
Arg Arg Pro Leu Trp Glu Ser Gly Pro Thr Val Asp Met Pro Val Pro
65                  70                  75                  80
Ser Ser Phe Asn Asp Ile Ser Gln Asp Trp Arg Leu Arg His Phe Val
                85                  90                  95
Gly Trp Val Trp Tyr Glu Arg Glu Val Ile Leu Pro Glu Arg Trp Thr
                100                 105                 110
Gln Asp Leu Arg Thr Arg Val Val Leu Arg Ile Gly Ser Ala His Ser
        115                 120                 125
Tyr Ala Ile Val Trp Val Asn Gly Val Asp Thr Leu Glu His Glu Gly
        130                 135                 140
Gly Tyr Leu Pro Phe Glu Ala Asp Ile Ser Asn Leu Val Gln Val Gly
145                 150                 155                 160
Pro Leu Pro Ser Arg Leu Arg Ile Thr Ile Ala Ile Asn Asn Thr Leu
                165                 170                 175
Thr Pro Thr Thr Leu Pro Pro Gly Thr Ile Gln Tyr Leu Thr Asp Thr
                180                 185                 190
Ser Lys Tyr Pro Lys Gly Tyr Phe Val Gln Asn Thr Tyr Phe Asp Phe
        195                 200                 205
Phe Asn Tyr Ala Gly Leu Gln Arg Ser Val Leu Leu Tyr Thr Thr Pro
        210                 215                 220
Thr Thr Tyr Ile Asp Asp Ile Thr Val Thr Thr Ser Val Glu Gln Asp
225                 230                 235                 240
Ser Gly Leu Val Asn Tyr Gln Ile Ser Val Lys Gly Ser Asn Leu Phe
```

-continued

```
                245                 250                 255
Lys Leu Glu Val Arg Leu Leu Asp Ala Glu Asn Lys Val Ala Asn
            260                 265                 270
Gly Thr Gly Thr Gln Gly Gln Leu Lys Val Pro Gly Val Ser Leu Trp
        275                 280                 285
Trp Pro Tyr Leu Met His Glu Arg Pro Ala Tyr Leu Tyr Ser Leu Glu
        290                 295                 300
Val Gln Leu Thr Ala Gln Thr Ser Leu Gly Pro Val Ser Asp Phe Tyr
305                 310                 315                 320
Thr Leu Pro Val Gly Ile Arg Thr Val Ala Val Thr Lys Ser Gln Phe
                325                 330                 335
Leu Ile Asn Gly Lys Pro Phe Tyr Phe His Gly Val Asn Lys His Glu
            340                 345                 350
Asp Ala Asp Ile Arg Gly Lys Gly Phe Asp Trp Pro Leu Leu Val Lys
        355                 360                 365
Asp Phe Asn Leu Leu Arg Trp Leu Gly Ala Asn Ala Phe Arg Thr Ser
    370                 375                 380
His Tyr Pro Tyr Ala Glu Glu Val Met Gln Met Cys Asp Arg Tyr Gly
385                 390                 395                 400
Ile Val Val Ile Asp Glu Cys Pro Gly Val Gly Leu Ala Leu Pro Gln
                405                 410                 415
Phe Phe Asn Asn Val Ser Leu His His Met Gln Val Met Glu Glu
            420                 425                 430
Val Val Arg Arg Asp Lys Asn His Pro Ala Val Met Trp Ser Val
        435                 440                 445
Ala Asn Glu Pro Ala Ser His Leu Glu Ser Ala Gly Tyr Tyr Leu Lys
    450                 455                 460
Met Val Ile Ala His Thr Lys Ser Leu Asp Pro Ser Arg Pro Val Thr
465                 470                 475                 480
Phe Val Ser Asn Ser Asn Tyr Ala Ala Asp Lys Gly Ala Pro Tyr Val
                485                 490                 495
Asp Val Ile Cys Leu Asn Ser Tyr Tyr Ser Trp Tyr His Asp Tyr Gly
            500                 505                 510
His Leu Glu Leu Ile Gln Leu Gln Leu Ala Thr Gln Phe Glu Asn Trp
        515                 520                 525
Tyr Lys Lys Tyr Gln Lys Pro Ile Ile Gln Ser Glu Tyr Gly Ala Glu
    530                 535                 540
Thr Ile Ala Gly Phe His Gln Asp Pro Pro Leu Met Phe Thr Glu Glu
545                 550                 555                 560
Tyr Gln Lys Ser Leu Leu Glu Gln Tyr His Leu Gly Leu Asp Gln Lys
                565                 570                 575
Arg Arg Lys Tyr Val Val Gly Glu Leu Ile Trp Asn Phe Ala Asp Phe
            580                 585                 590
Met Thr Glu Gln Ser Pro Thr Arg Val Leu Gly Asn Lys Lys Gly Ile
        595                 600                 605
Phe Thr Arg Gln Arg Gln Pro Lys Ser Ala Ala Phe Leu Leu Arg Glu
    610                 615                 620
Arg Tyr Trp Lys Ile Ala Asn Glu Thr Arg Tyr Pro His Ser Val Ala
625                 630                 635                 640
Lys Ser Gln Cys Leu Glu Asn Ser Pro Phe Thr
                645                 650

<210> SEQ ID NO 42
```

<211> LENGTH: 317
<212> TYPE: PRT
<213> ORGANISM: Homo sapiens

<400> SEQUENCE: 42

Met Pro Arg Glu Asp Arg Ala Thr Trp Lys Ser Asn Tyr Phe Leu Lys
1               5                   10                  15

Ile Ile Gln Leu Leu Asp Asp Tyr Pro Lys Cys Phe Ile Val Gly Ala
            20                  25                  30

Asp Asn Val Gly Ser Lys Gln Met Gln Gln Ile Arg Met Ser Leu Arg
        35                  40                  45

Gly Lys Ala Val Val Leu Met Gly Lys Asn Thr Met Met Arg Lys Ala
    50                  55                  60

Ile Arg Gly His Leu Glu Asn Asn Pro Ala Leu Glu Lys Leu Leu Pro
65                  70                  75                  80

His Ile Arg Gly Asn Val Gly Phe Val Phe Thr Lys Glu Asp Leu Thr
                85                  90                  95

Glu Ile Arg Asp Met Leu Leu Ala Asn Lys Val Pro Ala Ala Ala Arg
            100                 105                 110

Ala Gly Ala Ile Ala Pro Cys Glu Val Thr Val Pro Ala Gln Asn Thr
        115                 120                 125

Gly Leu Gly Pro Glu Lys Thr Ser Phe Phe Gln Ala Leu Gly Ile Thr
    130                 135                 140

Thr Lys Ile Ser Arg Gly Thr Ile Glu Ile Leu Ser Asp Val Gln Leu
145                 150                 155                 160

Ile Lys Thr Gly Asp Lys Val Gly Ala Ser Glu Ala Thr Leu Leu Asn
                165                 170                 175

Met Leu Asn Ile Ser Pro Phe Ser Phe Gly Leu Val Ile Gln Gln Val
            180                 185                 190

Phe Asp Asn Gly Ser Ile Tyr Asn Pro Glu Val Leu Asp Ile Thr Glu
        195                 200                 205

Glu Thr Leu His Ser Arg Phe Leu Glu Gly Val Arg Asn Val Ala Ser
    210                 215                 220

Val Cys Leu Gln Ile Gly Tyr Pro Thr Val Ala Ser Val Pro His Ser
225                 230                 235                 240

Ile Ile Asn Gly Tyr Lys Arg Val Leu Ala Leu Ser Val Glu Thr Asp
                245                 250                 255

Tyr Thr Phe Pro Leu Ala Glu Lys Val Lys Ala Phe Leu Ala Asp Pro
            260                 265                 270

Ser Ala Phe Val Ala Ala Pro Val Ala Ala Ala Thr Thr Ala Ala
        275                 280                 285

Pro Ala Ala Ala Ala Pro Lys Val Glu Ala Lys Glu Glu Ser
    290                 295                 300

Glu Glu Ser Asp Glu Asp Met Gly Phe Gly Leu Phe Asp
305                 310                 315

<210> SEQ ID NO 43
<211> LENGTH: 760
<212> TYPE: PRT
<213> ORGANISM: Homo sapiens

<400> SEQUENCE: 43

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

```
Asn Ser His Val Glu Met Lys Leu Ala Val Asp Glu Glu Asn Ala
        35                  40                  45
Asp Asn Asn Thr Lys Ala Asn Val Thr Lys Pro Lys Arg Cys Ser Gly
 50                  55                  60
Ser Ile Cys Tyr Gly Thr Ile Ala Val Ile Val Phe Phe Leu Ile Gly
 65                  70                  75                  80
Phe Met Ile Gly Tyr Leu Gly Tyr Cys Lys Gly Val Glu Pro Lys Thr
                     85                  90                  95
Glu Cys Glu Arg Leu Ala Gly Thr Glu Ser Pro Val Arg Glu Glu Pro
                100                 105                 110
Gly Glu Asp Phe Pro Ala Ala Arg Arg Leu Tyr Trp Asp Asp Leu Lys
            115                 120                 125
Arg Lys Leu Ser Glu Lys Leu Asp Ser Thr Asp Phe Thr Ser Thr Ile
        130                 135                 140
Lys Leu Leu Asn Glu Asn Ser Tyr Val Pro Arg Glu Ala Gly Ser Gln
145                 150                 155                 160
Lys Asp Glu Asn Leu Ala Leu Tyr Val Glu Asn Gln Phe Arg Glu Phe
                165                 170                 175
Lys Leu Ser Lys Val Trp Arg Asp Gln His Phe Val Lys Ile Gln Val
                180                 185                 190
Lys Asp Ser Ala Gln Asn Ser Val Ile Ile Val Asp Lys Asn Gly Arg
            195                 200                 205
Leu Val Tyr Leu Val Glu Asn Pro Gly Gly Tyr Val Ala Tyr Ser Lys
        210                 215                 220
Ala Ala Thr Val Thr Gly Lys Leu Val His Ala Asn Phe Gly Thr Lys
225                 230                 235                 240
Lys Asp Phe Glu Asp Leu Tyr Thr Pro Val Asn Gly Ser Ile Val Ile
                245                 250                 255
Val Arg Ala Gly Lys Ile Thr Phe Ala Glu Lys Val Ala Asn Ala Glu
                260                 265                 270
Ser Leu Asn Ala Ile Gly Val Leu Ile Tyr Met Asp Gln Thr Lys Phe
            275                 280                 285
Pro Ile Val Asn Ala Glu Leu Ser Phe Phe Gly His Ala His Leu Gly
        290                 295                 300
Thr Gly Asp Pro Tyr Thr Pro Gly Phe Pro Ser Phe Asn His Thr Gln
305                 310                 315                 320
Phe Pro Pro Ser Arg Ser Ser Gly Leu Pro Asn Ile Pro Val Gln Thr
                325                 330                 335
Ile Ser Arg Ala Ala Ala Glu Lys Leu Phe Gly Asn Met Glu Gly Asp
            340                 345                 350
Cys Pro Ser Asp Trp Lys Thr Asp Ser Thr Cys Arg Met Val Thr Ser
        355                 360                 365
Glu Ser Lys Asn Val Lys Leu Thr Val Ser Asn Val Leu Lys Glu Ile
        370                 375                 380
Lys Ile Leu Asn Ile Phe Gly Val Ile Lys Gly Phe Val Glu Pro Asp
385                 390                 395                 400
His Tyr Val Val Val Gly Ala Gln Arg Asp Ala Trp Gly Pro Gly Ala
                405                 410                 415
Ala Lys Ser Gly Val Gly Thr Ala Leu Leu Leu Lys Leu Ala Gln Met
            420                 425                 430
Phe Ser Asp Met Val Leu Lys Asp Gly Phe Gln Pro Ser Arg Ser Ile
        435                 440                 445
```

```
Ile Phe Ala Ser Trp Ser Ala Gly Asp Phe Gly Ser Val Gly Ala Thr
    450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
        515                 520                 525

Ala Ser Lys Val Glu Lys Leu Thr Leu Asp Asn Ala Ala Phe Pro Phe
    530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
        595                 600                 605

Leu Asp Tyr Glu Arg Tyr Asn Ser Gln Leu Leu Ser Phe Val Arg Asp
    610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
            660                 665                 670

Lys Leu Asn Asp Arg Val Met Arg Val Glu Tyr His Phe Leu Ser Pro
    675                 680                 685

Tyr Val Ser Pro Lys Glu Ser Pro Phe Arg His Val Phe Trp Gly Ser
690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
        755                 760

<210> SEQ ID NO 44
<211> LENGTH: 114
<212> TYPE: PRT
<213> ORGANISM: Homo sapiens

<400> SEQUENCE: 44

Met Thr Cys Lys Met Ser Gln Leu Glu Arg Asn Ile Glu Thr Ile Ile
1               5                   10                  15

Asn Thr Phe His Gln Tyr Ser Val Lys Leu Gly His Pro Asp Thr Leu
                20                  25                  30

Asn Gln Gly Glu Phe Lys Glu Leu Val Arg Lys Asp Leu Gln Asn Phe
            35                  40                  45

Leu Lys Lys Glu Asn Lys Asn Glu Lys Val Ile Glu His Ile Met Glu
    50                  55                  60
```

```
Asp Leu Asp Thr Asn Ala Asp Lys Gln Leu Ser Phe Glu Glu Phe Ile
 65              70                  75                  80

Met Leu Met Ala Arg Leu Thr Trp Ala Ser His Glu Lys Met His Glu
             85                  90                  95

Gly Asp Glu Gly Pro Gly His His His Lys Pro Gly Leu Gly Glu Gly
            100                 105             110

Thr Pro
```